United States Patent
Riesel et al.

(10) Patent No.: US 11,896,719 B2
(45) Date of Patent: Feb. 13, 2024

(54) PHARMACEUTICAL COMPOSITIONS

(71) Applicant: CALLIDITAS THERAPEUTICS AB, Stockholm (SE)

(72) Inventors: Eva Kristina Riesel, Mölndal (SE); Lena Margareta Pereswetoff-Morath, Spånga (SE); Kari Sandvold, Uppsala (SE); Christian Olle Andreas Pedersen, Uppsala (SE)

(73) Assignee: CALLIDITAS THERAPEUTICS AB, Stockholm (SE)

( * ) Notice: Subject to any disclaimer, the term of this patent is extended or adjusted under 35 U.S.C. 154(b) by 0 days.

(21) Appl. No.: 18/100,396

(22) Filed: Jan. 23, 2023

(65) Prior Publication Data
US 2023/0293444 A1 Sep. 21, 2023

Related U.S. Application Data

(60) Provisional application No. 63/302,216, filed on Jan. 24, 2022, provisional application No. 63/302,226, filed on Jan. 24, 2022.

(30) Foreign Application Priority Data

Nov. 16, 2022 (GB) ........................ 2217146
Nov. 16, 2022 (GB) ........................ 2217150

(51) Int. Cl.
*A61K 9/48* (2006.01)
*A61K 9/28* (2006.01)
(Continued)

(52) U.S. Cl.
CPC .......... *A61K 9/4891* (2013.01); *A61K 9/2846* (2013.01); *A61K 9/5047* (2013.01); *A61K 31/58* (2013.01); *A61P 13/12* (2018.01)

(58) Field of Classification Search
None
See application file for complete search history.

(56) References Cited

U.S. PATENT DOCUMENTS 4,123,403 A 10/1978 Warner
4,502,888 A 3/1985 Leng
(Continued)

FOREIGN PATENT DOCUMENTS

CN 101108171 A 1/2008
CN 105663091 A 6/2016
(Continued)

OTHER PUBLICATIONS

Molyneux et al.P0344 Nefecon® (Budesonide) Selectivelyreduces Circulating Levels of BAFF(BLYS) and Soluble BCMA and TACI INIGA Nephropathy. Nephrology Dialysis Transplantation, vol. 35, Issue Supplement_3,Jun. 2020, 3 pages. online publciation (Year: 2020).*

(Continued)

*Primary Examiner* — Lakshmi S Channavajjala
(74) *Attorney, Agent, or Firm* — Troutman Pepper Hamilton Sanders LLP (Rochester)

(57) ABSTRACT

The present invention provides for a method of treatment of IgA nephropathy, which method comprises:
(i) identifying a pharmaceutically acceptable composition intended to treat IgA nephropathy comprising budesonide and one or more pharmaceutically-acceptable excipients that provide for a modified release of said budesonide after administration to the gastrointestinal tract, which composition fulfils the following requirements in a standard in vitro USP<711>/Ph.Eur. 2.9.3 dissolution test using a dissolution apparatus according to Apparatus 2 (Paddle Apparatus) of said test;
(a) the composition fulfils the requirement that no more than about 10% of the budesonide is released into the
(Continued)

dissolution medium within about 120 minutes, when the dissolution medium is aqueous and has a pH of about 1.2;

(b) the composition fulfils the requirement that no more than about 10% of the budesonide is released into a pharmaceutically-relevant dissolution medium within about 30 minutes; and (c) the composition fulfils the requirement that at least about 70% of the budesonide is released into the pharmaceutically-relevant dissolution medium within about 120 minutes;

(ii) wherein the method comprises the step of administering said composition to a patient with IgA nephropathy in need of said treatment.

26 Claims, 24 Drawing Sheets

(51) Int. Cl.
A61K 31/58 (2006.01)
A61P 13/12 (2006.01)
A61K 9/50 (2006.01)

(56) References Cited

U.S. PATENT DOCUMENTS

| | | | |
|---|---|---|---|
| 5,681,584 A | 10/1997 | Savastano et al. | |
| 5,914,122 A | 6/1999 | Otterbeck et al. | |
| 5,932,249 A | 8/1999 | Gruber et al. | |
| 6,200,602 B1 | 3/2001 | Watts et al. | |
| 6,228,396 B1 | 5/2001 | Watts | |
| 6,239,120 B1 | 5/2001 | Hallgren et al. | |
| 6,423,340 B1 | 7/2002 | Ulmius | |
| 6,534,549 B1 | 3/2003 | Newton et al. | |
| 8,491,932 B2 | 7/2013 | Watts et al. | |
| 8,945,616 B2 * | 2/2015 | Murty | A61K 9/2072 427/2.16 |
| 10,286,036 B2 | 5/2019 | Solomons et al. | |
| 2002/0192282 A1 | 12/2002 | Beckert et al. | |
| 2005/0089571 A1 | 4/2005 | Beckert et al. | |
| 2006/0057200 A1 | 3/2006 | Schaeffler | |
| 2009/0004281 A1 | 1/2009 | Nghiem et al. | |
| 2010/0209501 A1 | 8/2010 | Murty et al. | |
| 2011/0189293 A1 | 8/2011 | Padval | |
| 2014/0088052 A1 | 3/2014 | Biswal et al. | |
| 2014/0256644 A1 | 9/2014 | Ward et al. | |
| 2015/0118296 A1 | 4/2015 | Kulkarni et al. | |
| 2017/0071863 A1 | 3/2017 | Thennati et al. | |
| 2017/0100411 A1 | 4/2017 | Bodick et al. | |
| 2017/0319698 A1 | 11/2017 | Vergnault et al. | |
| 2018/0256606 A1 | 9/2018 | Petereit et al. | |
| 2019/0125678 A1 | 5/2019 | Murty et al. | |
| 2019/0125687 A1 | 5/2019 | Bielski et al. | |
| 2021/0085622 A1 | 3/2021 | Vasisht et al. | |
| 2021/0139555 A1 | 5/2021 | Mayer-Bartschmid et al. | |

FOREIGN PATENT DOCUMENTS

| | | | | |
|---|---|---|---|---|
| CN | 110507627 A | | 11/2019 | |
| CN | 112999229 A | | 6/2021 | |
| CN | 115737597 A | | 3/2023 | |
| EP | 673645 A2 * | | 9/1995 | A61K 9/2886 |
| EP | 0754452 A2 | | 1/1997 | |
| EP | 1125629 A2 | | 8/2001 | |
| EP | 1302200 A1 | | 4/2003 | |
| EP | 1325775 A1 | | 7/2003 | |
| EP | 1527772 A1 | | 5/2005 | |
| EP | 1622711 | | 2/2006 | |
| EP | 1631373 | | 3/2006 | |
| EP | 1915135 | | 4/2008 | |
| EP | 1965775 | | 9/2008 | |
| EP | 2278958 B1 | | 1/2012 | |
| EP | 1590144 B1 | | 7/2015 | |
| WO | 1991007172 A1 | | 5/1991 | |
| WO | 1995035100 A1 | | 12/1995 | |
| WO | WO-9947144 A1 * | | 9/1999 | A61K 31/573 |
| WO | 00/76478 A1 | | 6/2000 | |
| WO | 2008113856 A1 | | 9/2008 | |
| WO | 2009138716 A1 | | 11/2009 | |
| WO | WO-2009138716 A1 * | | 11/2009 | A61K 9/4891 |
| WO | 2010035217 A1 | | 4/2010 | |
| WO | 2010035219 A2 | | 4/2010 | |
| WO | 2010035220 A1 | | 4/2010 | |
| WO | 2010035221 A1 | | 4/2010 | |
| WO | 2011056115 A1 | | 11/2010 | |
| WO | 2012150892 A1 | | 11/2012 | |
| WO | 2013068972 A1 | | 5/2013 | |
| WO | 2015049655 A1 | | 4/2015 | |
| WO | 2015071812 A1 | | 5/2015 | |
| WO | 2015072909 A1 | | 5/2015 | |
| WO | 2016098005 A1 | | 6/2016 | |
| WO | 2016189501 A1 | | 12/2016 | |
| WO | 2019086579 A1 | | 5/2019 | |
| WO | 2020011938 A1 | | 1/2020 | |
| WO | 2020065048 A1 | | 4/2020 | |
| WO | 2021127003 A1 | | 6/2021 | |

OTHER PUBLICATIONS

Fellström. Targeted-release budesonide versus placebo in patients with IgA nephropathy (NEFIGAN): a double-blind, randomised, placebo-controlled phase 2b trial. The Lancet, vol. 389, Issue 10084, May 27-Jun. 2, 2017, pp. 2117-2127 (Year: 2017).*

Gharavi et al. IgA nephropathy, the most common cause of glomerulonephritis, is linked to 6q22-23. Nature Genetics, Nov. 2000. vol. 26:354-357 (Year: 2000).*

International Search Report and Written Opinion for PCT/EP2023/051680, dated Mar. 29, 2023.

Press Release, Calliditas Therapeutics, "Pharmalink AB receives patent for Nefecon® principle. Japanese grant supports Asian partnering program," Oct. 26, 2009 (available at https://www.calliditas.se/en/pharmalink-ab-receives-patent-for-nefecon-principle-japanese-grant-supports-asian-partnering-program/).

Press Release, Fierce Biotech, "Pharmalink AB Gains Exclusive Licence to Archimedes Pharma's Targit® Technology for Nefecon® (PL-56) Program," Dec. 13, 2011 (available at https://www.fiercebiotech.com/biotech/pharmalink-ab-gains-exclusive-licence-to-archimedes-pharma-s-targit%C2%AE-technology-for-nefecon).

Press Release, Calliditas Therapeutics, "Pharmalink enters manufacturing agreement for Nefecon®," Oct. 31, 2012 (available at https://www.calliditas.se/en/pharmalink-enters-manufacturing-agreement-for-nefecon/).

Press Release, Calliditas Therapeutics, "Pharmalink's core patents for Nefecon® treatment for renal disease granted in United States, Europe, China and Hong Kong," Jul. 10, 2014 (available at https://www.calliditas.se/en/pharmalinks-core-patents-for-nefecon-treatment-for-renal-disease-granted-in-united-states-europe-china-and-hong-kong/).

Press Release, Pressmeddelande, "Pharmalink AB Receives US Orphan Drug Designation for Nefecon® (PL-56)," Oct. 13, 2010 (available at https://www.mynewsdesk.com/se/pharmalink-ab/pressreleases/pharmalink-ab-receives-us-orphan-drug-designation-for-nefecon-pl-56-495020).

Press Release, Calliditas Therapeutics, "Pharmalink initiates a pivotal Phase IIb trial with Nefecon® in patients with primary IgA nephropathy," Dec. 18, 2012 (available at https://www.calliditas.se/en/pharmalink-initiates-a-pivotal-phase-iib-trial-with-nefecon-in-patients-with-primary-iga-nephropathy/).

Prospectus of Calliditas Therapeutics (without financial statements) (available at https://www.sec.gov/Archives/edgar/data/1795579/000110465920070680/tm2019773-4_424b4.htm), Securities and Exchange Commission, Washington DC (Jun. 2020).

Everest Medicines Announces First Patient Randomized in a Phase 3 Clinical Study of Nefecon for IgA Nephropathy Patients in China, Sep. 8, 2020—https://www.everestmedicines.com/News_detail.aspx?nid=185.

(56) References Cited

OTHER PUBLICATIONS

Ismail et al., "Budesonide Versus Systemic Corticosteroids in IgA Nephropathy: A Retrospective, Propensity-matched Comparison," Medicine 99(26):e21000 (2020).
Raval et al., "Formulation and Evaluation of Sustained Release Enteric-coated Pellets of Budesonide for Intestinal Delivery," Int. J. Pharm. Investig. 3(4):203-211 (2013).
Smerud et al., "New Treatment for IgA Nephropathy: Enteric Budesonide Targeted to the Ileocecal Region Ameliorates Proteinuria," Nephrol. Dial. Transplant 26(10):3237-3242 (2011).
Tsuda et al., "Targeted-release Budesonide Therapy for IgA Nephropathy," Lancet 390(10113):2625 (2017).
Book of Abstracts, IIGANN Argentina, Kidney Dis. (Basel) 4(3):145-194 (2018).
EU Clinical Trials Register—EudraCT No. 2017-004902-16—https://www.clinicaltrialsregister.eu/ctr-search/trial/2017-004902-16/GB; Amsterdam, Netherlands (2018).
Efficacy and Safety of Nefecon in Patients With Primary IgA (Immunoglobulin A) Nephropathy (Nefigard)—https://clinicaltrials.gov/ct2/show/NCT03643965?term=nefecon&draw=2; Bethesda, MD (2018).
Levina et al., Poster Reprint of "The Effect of Hypromellose as a Pore-Former on Drug Release from Aqueous Ethylcellulose Film-Coated Dipyridamole-Loaded Non-Pareil Beads", Controlled Release Society, Modified Release; Colorcon, West Point, PA (Jul. 2007).
Ong et al., Poster Reprint of "Investigation of the Relationship between Formulation Variables and Drug Release in Aqueous Ethylcellulose Coating", Controlled Release Society, Modified Release; Colorcon, West Point, PA (Jul. 2007).
Palmer et al., Poster Reprint of "The Influence of Hydrophilic Pore Formers on Dipyridamole Release from Aqueous Ethylcellulose Film-Coated Pellets", AAPS Annual Meeting, Modified Release; Colorcon, West Point, PA (Nov. 2007).
Ong et al., Poster Reprint of "Hypromellose as a Pore Former in Aqueous Ethylcellulose Dispersion: Stability and Film Properties", AAPS Annual Meeting, Modified Release; Colorcon, West Point, PA (Nov. 2006).
Preliminary Prospectus of Calliditas Therapeutics (without financial statements) (https://www.sec.gov/Archives/edgar/data/1795579/000110465921007672/tm2039250-2_f1.htm), Securities and Exchange Commission, Washington DC (Jan. 2021).
Jerling et al., "Systemic GCS Exposure From Nefecon Administration, Estimated From Suppression of Endogenous Cortisol Production," Abstract of Presentation at American Society of Nephrology 2019, Washington DC (Nov. 7, 2019).
Fellstrom et al., "Targeted-release budesonide versus placebo in patients with IgA nephropathy (NEFIGAN): a double-blind, randomised, placebo-controlled phase 2b trial," Lancet 389(10084):2117-2127 (2017).
Ozturk et al., "Kinetics of Release from Enteric-coated Tablet," Pharm. Research 5(9):550-565 (1988).
Markopoulos et al., "In-vitro Simulation of Luminal Conditions for Evaluation of Performance of Oral Drug Products: Choosing the Appropriate Test Media," Eur. J. Pharm. Biopharm. 93:173-182 (2015).
Mackay et al., "Cracking the BAFF Code," Nat. Rev. Immunol. 9:491-502 (2009).
Schneider et al., "BAFF, a Novel Ligand of the Tumor Necrosis Factor Family, Stimulates B Cell Growth," J. Exp. Med. 189:1747-1756 (1999).
Yu et al., "APRIL and TALL-1 and Receptors BCMA and TACI: System for Regulating Humoral Immunity," Nat. Immunol. 1:252-256 (2000).
Steri et al., "Overexpression of the Cytokine BAFF and Autoimmunity Risk," N. Engl. J. Med. 376:1615-1626 (2017).
Barratt et al., "Treatment of IgA Nephropathy: Evolution Over Half a Century," Semin. Nephrol. 38(5):531-540 (2018).
Seikrit et al., "The Immune Landscape of IgA Induction in the Gut," Semin. Immunopathol. 43:627-637 (2021).

Boyd et al., "An Update on the Pathogenesis and Treatment of IgA Nephropathy," Kidney Int. 81:833-843 (2012).
Klein, "The Use of Biorelevant Dissolution Media to Forecast the In Vivo Performance of a Drug," AAPS J. 12:397-406 (2020).
Molyneux et al., Abstract of Presentation from ERA-EDTA Symposium 2020, "Nefecon® (Budesonide) selectively reduces circulating levels of BAFF (BLyS) and soluble BCMA and TACI in IgA Nephropathy," Nephrology Dialysis Transplantation 35:iii648 (Abstract P0344) (2020).
Barratt et al., Abstract of Presentation from ERA-EDTA Symposium 2020, "The Nefigard Trial: The Effect of Nefecon® (Budesonide) in Patients With Primary IgA Nephropathy at Risk of Developing End-stage Renal Disease," Nephrology Dialysis Transplantation 35:iii532 (Abstract P0228) (2020).
Fellstrom et al., Title of Presentation from the Lancet/ERA-EDTA Symposium 2017, "Effects of a Novel Targeted Release Formulation of Budesonide vs. Placebo in IgA Nephropathy: The Nefigan Randomised Clinical Trial" (Jun. 4, 2017).
Fellstrom et al., Abstract of Presentation at ERA-EDTA Symposium 2017, "Proteinuria Reduction in IgA Nephropathy by Nefecon, a Targeted Release Formulation of Budesonide—Results From the Nefigan Trial," Nephrology Dialysis Transplantation 32:iii82-iii83 (Abstract TO013) (2017).
Selvaskandan et al., "New Strategies and Perspectives on Managing IgA Nephropathy," Clin. Exp. Nephrol. 23(5):577-588 (2019).
Cheung et al., "An Update on the Current State of Management and Clinical Trials for IgA Nephropathy," J. Clin. Med. 10(11):2493 (2021).
Chang et al., "The Role of Immune Modulation in Pathogenesis of IgA Nephropathy," Front. Med. 7:92 (2020).
Novak et al., "New Insights into the Pathogenesis of IgA Nephropathy," Kidney Dis. (Basel) 1(1):8-18 (2015).
Barratt et al., "Why Target the Gut to Treat IgA Nephropathy?," Kidney Int. Rep. 5(10):1620-1624 (2020).
Kiryluk et al., "The Genetics and Immunobiology of IgA Nephropathy," J. Clin. Invest. 124(6):2325-32 (2014).
Wilson et al., "Chapter 3—Gastrointestinal Transit and Drug Absorption" In: "Oral Drug Absorption: Prediction and Assessment", 2nd Edition, Edited by J. Dressman and C. Reppas, Drug and the Pharmaceutical Sciences vol. 193 Marcel Dekker, NY, NY ISBN-13: 978-1-4200-7733-9, pp. 41-65 (2010).
Hammers D. W., "Nox4 Inhibition Promotes the Remodeling of Dystrophic Muscle," JCI Insight 7(20):e158316 (2022) Also published on bioRxiv, doi: https://doi.org/10.1101/2022.01.08.475493.
Hammers D., Abstract of Poster 18, Presentation at MDA Conference 2021, "Nox4 Inhibition Reduces Skeletal Muscle Fibrosis in a Severe Murine Model of Duchenne Muscular Dystrophy," (2021) (available at: https://www.mdaconference.org/abstracts/2021-abstract-library/).
Augsburger et al., "Pharmacological Characterization of the Seven Human NOX Isoforms and Their Inhibitors," Redox Biol. 26:101272 (2019).
Ismail H. M., "Diapocynin, a Dimer of the NADPH Oxidase Inhibitor Apocynin, Reduces ROS Production and Prevents Force Loss in Eccentrically Contracting Dystrophic Muscle," Plos One 9(10):e110708 (2014).
Watts et al., "Targit Technology: Coated Starch Capsules for Site-specific Drug Delivery Into the Lower Gastrointestinal Tract," Expert Opin. Drug. Deliv. 2(1):159-167 (2005).
Inker et al., "Early Change in Urine Protein as a Surrogate End Point in Studies of IgA Nephropathy: An Individual-Patient Meta-analysis," Am. J. Kidney Dis. 68(3):392-401 (2016).
Kobayashi et al., "The Roles of Peyer's Patches and Microfold Cells in the Gut Immune System: Relevance to Autoimmune Diseases," Front. Immunol. 10:2345 (2019).
Miller et al., "Chapter 12—Aqueous Polymeric Film Coating" In: "Pharmaceutical Dosage Forms: Tablets", 3rd Edition, vol. 1: Unit Operations and Mechanical Properties, Edited by L. L. Augsburger and S. W. Hoag; ISBN 9780949390142, pp. 399-437 (2008).
Rekhi et al., "Bioavailability and In-vitro/in-vivo Correlation for Propranolol Hydrochloride Extended-release Bead Products Prepared Using Aqueous Polymeric Dispersions," J. Pharm. Pharmacol. 48:1276-1284 (1996).

(56) References Cited

OTHER PUBLICATIONS

Kosztyu et al., "Glucocorticoids Reduce Aberrant O-Glycosylation of IgA1 in IgA Nephropathy Patients," Kidney Blood Press. Res. 43:350-359 (2018).
Seidegard et al., "Presystemic Elimination of Budesonide in Man When Administered Locally at Different Levels in the Gut, With and Without Local Inhibition by Ketoconazole," Eur. J. Pharm. Sci. 35(4):264-270 (2008).
Raje et al., "Evaluation of Separate Role of Intestine and Liver in First Pass Metabolism of Budesonide in Fat," Xenobiotica 48(12):1206-1214 (2018).
Gesualdo et al., "The Mucosal Immune System and IgA Nephropathy," Semin. Immunopathol. 43:657-668 (2021).
Coppo R., "The Gut-Renal Connection in IgA Nephropathy," Semin. Nephrol. 38:504-512 (2018).
O'Grady et al., "Defining Gastrointestinal Transit Time Using Video Capsule Endoscopy: A Study of Healthy Subjects," Endoscopy Int. Open 08:E396-E400 (2020).
Sager et al., "Low Dose Caffeine as a Salivary Tracer for the Determination of Gastric Water Emptying in Fed and Fasted State: A MRI Validation Study," Eur. J. Pharm. Biopharm. 127:443-452 (2018).
Newton et al., "Plasma and Salivary Pharmacokinetics of Caffeine in Man," Eur. J. Clin. Pharmacol. 21:45-52 (1981).
Molyneux et al., Abstract of Poster Presentation at American Society of Nephrology (ASN) Annual Kidney Week 2021 Conference, "Targeted Release Formulation Budesonide (Nefecon) Selectively Reduces Circulating Levels of Chemokines Critical to Immune Cell Trafficking to Peyer Patches in IgA Nephropathy," J. Am. Soc. Nephrol., 32:4-7 (Abstract PO1453) (Nov. 2021).
Perez-Alos et al., Abstract of Poster Presentation at American Society of Nephrology (ASN) Annual Kidney Week 2021 Conference, "Treatment with Targeted Release Formulation Budesonide (Nefecon) Modulates the Complement System in Patients with IgA Nephropathy," J. Am. Soc. Nephrol., 32:4-7 (Abstract PO1455) (Nov. 2021).
Seikrit et al., Abstract of Poster Presentation from Proceedings of 16th International Symposium on IgA Nephropathy IgA Nephropathy 2021, "Analysis of the Effect of TRF-Budesonide (Nefecon) on Urinary sCD163 in Patients With IgAN From the Phase 2 Nefigan Trial," at p. 58 (Sep. 21, 2021) (published online at https://www.karger.com/Article/Pdf/519532).
Maixnerova et al., Abstract of Poster Presentation from Proceedings of 16th International Symposium on IgA Nephropathy IgA Nephropathy 2021, "TRF-budesonide (Nefecon) Positively Impacts Serum and Urinary Biomarkers Involved in Interstitial Fibrosis in Patients With IgAN: Analysis From the Phase 2 NefiganTrial", at p. 68 (Sep. 21, 2021) (published online at https://www.karger.com/Article/Pdf/519532).
Stone et al., Abstract of Poster Presentation from Proceedings of 16th International Symposium on IgA Nephropathy IgA Nephropathy 2021, "eGFR Slope at 1 Year May Independently Predict Clinical Benefit in Patients With IgA Nephropathy", at pp. 58-59 (Sep. 21, 2021) (published online at https://www.karger.com/Article/Pdf/519532).
Bhachu et al., Abstract of Poster Presentation from Proceedings of 15th International Symposium on IgA Nephropathy IgA Nephropathy 2018, "Targeted Release-Budesonide (Nefecon) Modifies Circulating IGA-IGG Immune Complex Levels and Levels of Poorly O-galactosylated IgA in IgAN," Kidney Dis. 4:121-122 (2018) (published online at https://www.ncbi.nlm.nih.gov/pmc/articles/PMC6173210/).
Muto et al., Abstract of Poster Presentation from Proceedings of 15th International Symposium on IgA Nephropathy IgA Nephropathy 2018, "Targeted Release-Budesonide (Nefecon) Modifies Mucosal IgA Responses and Possibly Gut Permeability in IgA Nephropathy," Kidney Dis. 4:138-139 (2018) (published online at https://www.ncbi.nlm.nih.gov/pmc/articles/PMC6173210/).
Soares et al., Abstract of Poster Presentation from Proceedings of 15th International Symposium on IgA Nephropathy IgA Nephropathy 2018, "Extent of Segmental Glomerulosclerosis in IgA Nephropathy is Associated With the Level of eGFR Response to TRF-budesonide (Nefecon)," Kidney Dis. 4:113 (2018) (published online at https://www.ncbi.nlm.nih.gov/pmc/articles/PMC6173210/).
Fellstrom et al., Abstract of Poster Presentation from Proceedings of 15th International Symposium on IgA Nephropathy IgA Nephropathy 2018, "Treatment of IgA Nephropathy With Nefecon, a Targeted release Formulation of Fudesonide—Extended Posthoc Results From the Nefigan Trial," Kidney Dis. 4:140 (2018) (published online at https://www.ncbi.nlm.nih.gov/pmc/articles/PMC6173210/).
Haggblad et al., Abstract of Poster Presentation from Proceedings of 15th International Symposium on IgA Nephropathy IgA Nephropathy 2018, "Nefecon, an Oral Disease Modifying Treatment for Progressive IgA Nephropathy. The Strategy Behind Developing Proteinuria as Surrogate Endpoint for Accelerated Approval," Kidney Dis. 4:143-144 (2018) (published online at https://www.ncbi.nlm.nih.gov/pmc/articles/PMC6173210/).
Vecchio et al., "Nefecon (targeted-release formulation budesonide) for the treatment of IgA nephropathy," Future Rare Diseases, 1(4) (Dec. 2021).
Tatematsu et al., "Complete remission within 2 years predicts a good prognosis after methylprednisolone pulse therapy in patients with IgA nephropathy," Clinical and Experimental Nephrology, Springer-Verlag, 16(6):883-891 (2021).

\* cited by examiner

PHARMACEUTICAL COMPOSITIONS

This application claims the priority benefit of U.S. Provisional Patent Application Ser. Nos. 63/302,226 and 63/302,216, both filed on Jan. 24, 2022, which are hereby incorporated by reference in their entirety. The application also claims the priority benefit of GB Application Nos. 2217150.8 and 2217146.6, both filed on Nov. 16, 2022.

FIELD OF THE INVENTION

The invention relates to a method of treating IgA nephropathy and a method of determining whether a pharmaceutical composition is capable of safely and efficaciously treating IgA nephropathy. The invention also relates to compositions for use in treating IgA nephropathy and methods for producing those compositions.

PRIOR ART AND BACKGROUND

The listing or discussion of an apparently prior-published document in this specification should not necessarily be taken as an acknowledgement that the document is part of the state of the art or common general knowledge.

IgA nephropathy (IgAN), sometimes referred to as Berger's disease, is a serious progressive autoimmune disease of the kidney in which up to 50% of patients end up at risk of developing end-stage renal disease (ESRD) within ten to twenty years.

IgAN is an orphan disease and it is estimated that approximately 130,000 to 150,000 people are affected by the disease in the United States and approximately 200,000 people are affected in Europe. A significantly higher prevalence has been observed in Asia, including in Greater China, where IgAN has historically been a leading cause of ESRD. It is estimated that IgAN affects approximately two million people in Greater China.

Although IgAN manifests in the kidney, most scientific studies have found that the pathogenesis of IgAN begins in the ileum, which is the final part of the small intestine before the large intestine. Masses of lymphatic tissue, known as Peyer's patches, are predominantly found in the ileum where they produce secretory IgA antibodies. IgA antibodies play a key role in the immune system by protecting the body from foreign substances, such as food-derived factors, bacteria and viruses.

Patients with IgAN have elevated levels of a subclass of IgA antibodies produced in the gut that lack units of galactose at their hinge region. The hinge region is a flexible amino acid stretch in the central part of the heavy chains of the IgA antibody. In IgAN patients, a combination of genetic predisposition and environmental, bacterial or dietary factors are presumed to lead to an increased production of these galactose-deficient IgA antibodies, potentially in combination with increased intestinal permeability, leading to these antibodies appearing in the blood. The galactose-deficient IgA antibodies (also referred to herein as poorly O-galactosylated IgA1) are immunogenic when found in the circulation, which triggers autoantibodies, or antibodies created by the body in response to a constituent of its own tissue. This in turn leads to the formation of pathogenic immune complexes, or clusters of antibodies, which deposit in the membranes of the glomeruli, the kidney's filtration apparatus. These trapped immune complexes initiate an inflammatory cascade that damages the membranes, resulting in protein and blood leaking into the urine. Ultimately the glomeruli are destroyed, reducing the kidney's ability to remove waste products from the blood. As the disease progresses, waste products that are normally removed from the blood accumulate, resulting in potentially life-threatening complications that in many patients will lead to the need for dialysis or kidney transplant.

The standard of care for ESRD is dialysis or kidney transplant, which represents a significant health economic burden as well as a material impact on patients' quality of life.

Despite a need for new therapies, there have been few new drugs developed for chronic kidney diseases during the last decade and, until recently, there has been no approved therapy for the direct treatment of IgAN per se. Patients with IgAN are typically initially given antihypertensive medications. This treatment regimen initially attempts to manage the symptoms of IgAN by decreasing blood pressure and reducing proteinuria but has not been proven to address the underlying cause of IgAN. Over time, physicians attempt to control disease progression with a variety of off-label treatments, such as statins, omega-3-acids and diuretics, but a significant proportion of patients experience continued deterioration of kidney function, and until recently no approved treatment options have been available.

For IgAN patients whose disease has progressed, clinicians may treat patients with systemic immunosuppressive agents, primarily consisting of high doses of systemic corticosteroids, such as prednisone, prednisolone and methylprednisolone. While some published reports indicate that these agents may reduce proteinuria, this high dosing of systemic corticosteroids is also associated with a wide range of adverse events, including high blood pressure, weight gain, diabetes, serious infections and osteoporosis. Also, any potential impact on the underlying disease in terms of kidney function, as measured by estimated Glomerular Filtration Rate (eGFR), has yet to be proven.

Thus, in attempting to meet the present clinical need for an effective treatment of IgAN, there is a clear need for new and/or improved treatments for IgAN in which an effective local treatment with an immunosuppressive agent without such undesired side effects is obtained.

Peyer's patches (aggregated lymphoid nodules) are small masses of lymphatic tissue found throughout the ileum region of the small intestine. They are an important part of the immune system as they monitor intestinal bacteria populations and prevent the growth of pathogenic bacteria in the intestine.

As Peyer's patches are responsible for the synthesis of the bulk of IgA in the body, a targeted dose of locally-acting immunosuppressive agent to the ileum (and particularly the terminal/distal ileum), where Peyer's patches are predominantly found, may serve to reduce the formation of the IgA molecules that ultimately drive immune complex formation in IgAN, by reducing the formation of secretory galactose-deficient IgA antibodies and their appearance in the blood. Such targeted release will also likely limit systemic exposure of locally-acting immunosuppressants, such as certain corticosteroids, in order to avoid undesirable side-effects.

Peyer's Patches are sites of intense activation of B cells in the human body. Therefore, it stands to reason that monitoring survival factors related to B-cell activation would provide an indication as to the efficacy of treatments with locally-acting immunosuppressive agents.

The tumour necrosis factor (TNF) family members, B cell activating factor (BAFF) and its homolog a proliferation-inducing ligand (APRIL) are crucial survival factors for peripheral B-cells, and are expressed by cells including monocytes, dendritic cells, neutrophils, basophils, stromal cells, activated T-cells, cells of bowel mucosa, activated and malignant B-cells, and epithelial cells (Mackay and Schneider, 2009. *Nat. Rev. Immunol.,* 9:491-502; Schneider et al, 1999. 3. Exp. Med., 189:1747-1756; Yu et al, 2000. *Nat. Immunol.,* 1:252-256).

BAFF is a ligand for the receptors Transmembrane activator and CAML interactor (TACI), (also known as tumour necrosis factor receptor superfamily member 13B (TNFRSF13B)); B-cell maturation antigen (BCMA) (also known as tumour necrosis factor receptor superfamily member 17 (TNFRSF17)); and B-cell activating factor receptor (BAFF-R) (also known as tumour necrosis factor receptor superfamily member 13C (TNFRSFI3C)). BAFF-R is specific to BAFF, whereas TACI and BCMA also bind to APRIL (Mackay and Schneider, 2009. *Nat. Rev. Irmmunol.,* 9:491-502).

BAFF is a potent B cell activator and is crucial for B-cell homeostasis and for the regulation of B-cell selection. An excess of BAFF has been shown to be associated with the development of autoimmune disorders, such as IgAN, in animal models, and high levels of BAFF have been detected in the serum of patients with various autoimmune conditions. Increased levels of BAFF have been associated with an upregulation of humoral immunity through increased levels of B-cells and immunoglobulins (Steri et al, 2017. *N. Engl. J. Med.,* 376:1615-1626).

Increased serum levels of BAFF and APRIL are found in patients suffering from IgAN and this has led to the development of drugs that seek to inhibit those molecules. The focus of those drugs has been blocking the interaction between BAFF and/or APRIL and their receptors. For example, but not limited to, the BAFF inhibitor Blisibimod (Anthera Pharmaceuticals, discontinued) is a fusion protein consisting of four BAFF binding domains fused to the N-terminus of the Fc region of a human antibody, which binds to BAFF and inhibits interaction with BAFF receptors. Similarly, the combined BAFF/APRIL antagonist Atacicept (Merck Serono, licensed by Vera Therapeutics) is also a recombinant fusion protein that combines BAFF and APRIL binding domains with an antibody Fc region, and blocks interaction with TACI. The APRIL antagonist VIS649 (Visterra, a subsidiary of Otsuka) and the BAFF inhibitor Belimumab (GlaxoSmithKline) are monoclonal antibodies that bind directly to APRIL and BAFF respectively and block interaction with their receptors. Thus, drugs targeting BAFF and APRIL seek to block the activity of endogenous BAFF/APRIL molecules in order to reduce activation and proliferation of B-cells, and the associated immunological effects.

The current understanding of the pathogenesis and current treatments of IgAN are summarised in J. Barratt et al., Treatment of IgA Nephropathy: Evolution Over Half a Century, *Seminars in Nephrology,* 2018, 38(5), 531-540, see also Boyd et al., Kidney International, 2012, 81, 833-843. The current understanding of the pathogenesis of IgAN is also outlined in Seikrit et al., The Immune Landscape of IgA Induction in the Gut, *Seminars in Immunopathology,* 2021, 43, 627-637.

Surprisingly, we found that oral administration of a budesonide formulation with a distinct in vitro release profile leads to a pronounced decrease in the serum level of BAFF in those subjects relative to the level observed prior to administration of budesonide. Furthermore, the observed decrease in serum BAFF level may occur concomitantly with decreases in the levels of biomarkers associated with B-cell activation and proliferation. Accordingly, the in vitro release profile is indicative of successful targeted release in the intestine (i.e., successful targeted release to the distal ileum) of subjects.

In addition, what is particularly interesting is that it has been shown that treatment of IgAN with systemic glucocorticoids lowers both total serum IgA and poorly O-galactosylated IgA1 (Kosztyu P et al.: Glucocorticoids Reduce Aberrant O-Glycosylation of IgA1 in IgA Nephropathy Patients. Kidney Blood Press Res 2018; 43:350-359. However, with the present treatment of oral administration of a budesonide formulation as defined herein there were no differences observed in levels of total level of functional IgA antibodies, including IgA1 and IgG with budesonide capsule treatment, but serum levels of galactose-deficient IgA (poorly O-galactosylated IgA) did drop. This finding led to the conclusion that the effect of local ileal treatment with budesonide capsules was selective for the pathogenic antibodies but not effective on the general pool of IgA, IgA1 and IgG.

These results show that treatment with the budesonide formulation as defined herein is supportive of a direct effect on the underlying pathogenic pathways in IgAN and that the budesonide payload has a predominantly topical effect rather than a systemic effect, leading to reduced side effects for patients when treated with Nefecon budesonide.

To support this, in silico modelling of the budesonide formulation with the distinct in vitro release profile shows that the payload is released predominantly to the ileum, in particular the distal ileum. With budesonide having a high first pass rate, primarily through gut wall metabolism in the small intestine, (Seidegård J et. al., *Presystemic elimination of budesonide in man when administered locally at different levels in the gut,* with and without local inhibition by ketoconazole. Eur J Pharm Sci. 2008 Nov. 15; 35(4):264-70; Raje et al. *Evaluation of separate role of intestine and liver in first pass metabolism of budesonide in rat* Xenobiotica. 2018 December; 48(12):1206-1214)), these results are further indicative of the budesonide formulation having a topical rather than systemic effect.

Taken together, the results described herein show that budesonide formulations exhibiting the distinct in vitro release profile as defined herein are an effective treatment of IgAN. Due to their targeted local release and effect of the topical corticosteroid, a lower level of undesired side effects is obtained.

Formulations of the corticosteroid budesonide have previously been described in international patent application WO 2009/138716 A1.

DISCLOSURE OF THE INVENTION

Figure 1:
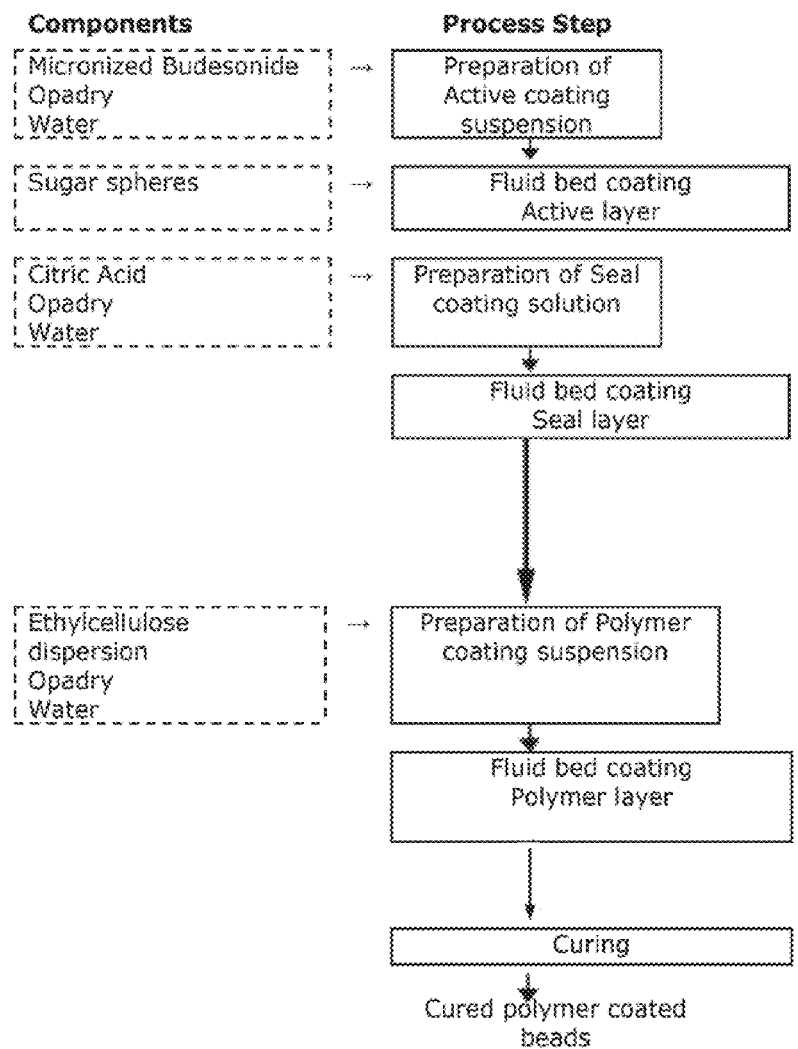
FIG. 1 is a flow diagram detailing the preparation of cured polymer coated beads.

According to a first aspect of the invention, there is provided a method of treatment of IgA nephropathy, which method comprises:
  (i) identifying a pharmaceutically acceptable composition intended to treat IgA nephropathy comprising budesonide and one or more pharmaceutically-acceptable excipients that provide for a modified release of said budesonide after administration to the gastrointestinal tract, which composition fulfils the following requirements in a standard in vitro USP<711>/Ph.Eur. 2.9.3 dissolution test using a dissolution apparatus according to Apparatus 2 (Paddle Apparatus) of said test (as described hereinafter);
    (a) the composition fulfils the requirement that no more than about 10% of the budesonide is released into the dissolution medium within about 120 minutes, when the dissolution medium is aqueous and has a pH of about 1.2;
    (b) the composition fulfils the requirement that no more than about 10% of the budesonide is released into a pharmaceutically-relevant dissolution medium within about 30 minutes; and
(c) the composition fulfils the requirement that at least about 70% of the budesonide is released into the pharmaceutically-relevant dissolution medium within about 120 minutes, then
(ii) administering said composition to a patient with IgA nephropathy in need of said treatment,
which method is referred to hereinafter as "the method of the invention".

By the term "pharmaceutically-relevant dissolution medium" we include media which is suitable for use in an in vitro dissolution assay the results of which are indicative of in vivo release at the relevant part of the intestinal tract. For example, the pharmaceutically-relevant dissolution medium may, in the alternative, be termed "enterically pharmaceutically-relevant dissolution medium" or "pharmaceutically-relevant enteric dissolution medium" may be any such medium that simulates dissolution and release in the small intestine or a relevant part thereof.

The pharmaceutically-relevant dissolution medium is preferably aqueous.

The pharmaceutically-relevant dissolution medium may have a pH of from about 6.2 to about 7.5, such as from about 6.5 to about 6.8.

The pharmaceutically-relevant dissolution medium may be a phosphate buffer medium at a pH of about 6.2, a Level 1 Fasted State Simulated Intestinal Fluid (FaSSIF) at a pH of about 6.5 (for example a FaSSIF buffer as defined below under the heading "Release in Level 1 Fasted State Simulated Intestinal Fluid at a pH of about 6.5"), a phosphate buffer medium at a pH of about 6.8 (for example the phosphate buffer defined below under the heading "Release in medium at pH 6.8"), or a phosphate buffer medium at a pH of about 7.2 or about 7.5.

The method of the invention may comprise (I) combining budesonide with one or more pharmaceutically-acceptable excipients that provide for a modified release of said budesonide after administration to the gastrointestinal tract to make a pharmaceutically-acceptable composition intended to treat IgA nephropathy, and then (II) testing the composition in the standard in vitro USP<711>/Ph.Eur. 2.9.3 dissolution test as set out above and, if the composition fulfils the requirements (a) to (c) as set out above, administering said composition to a patient with IgA nephropathy in need of said treatment.

As an alternative embodiment of the invention, there is provided a composition comprising a combination of budesonide with one or more pharmaceutically-acceptable excipients that provide for a modified release of said budesonide after administration to the gastrointestinal tract, wherein said composition fulfils the dissolution profile of step (i) outlined above for use in the treatment of IgA nephropathy.

As a further alternative embodiment of the invention, there is provided the use of a composition comprising a combination of budesonide with one or more pharmaceutically-acceptable excipients that provide for a modified release of said budesonide after administration to the gastrointestinal tract, wherein said composition fulfils the dissolution profile of step (i) outlined above for the manufacture of a medicament for the treatment of IgA nephropathy.

As referred to herein, the term "treatment" of IgA nephropathy, we further include the prophylaxis, or the diagnosis of the relevant condition in addition to therapeutic, symptomatic and/or palliative treatment.

For the avoidance of doubt, when referencing USP<711> we are referring to the test as published on 1 May 2016 and when referencing Ph.Eur. 2.9.3 we are referring to chapter 2.9.3 of the European Pharmacopoeia 10.0.

For the avoidance of doubt, step (ii) of administering the composition to a patient will only take place if the average (mean) of the tested compositions fulfils each and all of criteria (a), (b) and (c) of step (i).

As used herein, the term "budesonide" refers to a compound according to formula I:

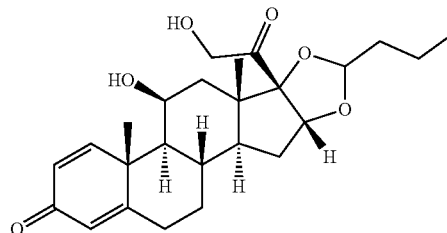

Formula I

Budesonide is also commonly referred to under its IUPAC name (16α,17-[(1RS)-butylidenebis(oxy)]-11β,21-dihydroxypregna-1,4-diene-3,20-dione).

Although the composition of the invention comprises budesonide, it is understood that the composition may alternatively comprise a different corticosteroid that is capable of having topical action in a similar fashion to budesonide. Such suitable alternative corticosteroids include, but are not limited to, aclometasone, beclomethasone, betamethasone, clobetasol, hydrocortisone, dexamethasone, flunisolide, methylprednisolone, mometasone, prednisolone, triamcinolone, fluticasone, ciclesonide, fludrocortisone and mixtures thereof, including mixtures comprising budesonide.

The Paddle Apparatus of Apparatus 2 may be operated at about 50 revolutions per minute (rpm), about 75 rpm or about 100 rpm. Preferably, the Paddle Apparatus of Apparatus 2 is operated at about 100 rpm, or at about 50 rpm.

The pharmaceutically-relevant dissolution medium of criterion b) and criterion c) may comprise a surfactant in an amount of about 0.5 mg/mL (0.05% w/v). The surfactant may be a polysorbate, preferably wherein the surfactant is polysorbate 80 (e.g., Tween 80).

In criterion a) of step (i) of the method the amount of budesonide released may be no more than about 5%, such as no more than about 2.5%, within about 120 minutes.

In criterion a) of step (i) of the method, the amount of budesonide released may be from about 0% to about 10%, such as from about 0% to about 5%, for example from about 0% to about 2.5%, within about 120 minutes.

In criterion b) of step (i) of the method the amount of budesonide released may be no more than about 5%, such as no more than about 2.5%, within about 30 minutes.

In criterion b) of step (i) of the method, the amount of budesonide released may be from about 0% to about 10%, such as from about 0% to about 5%, for example from about 0% to about 2.5%, within about 30 minutes.

In criterion c) of step (i) of the method the amount of budesonide released may be at least about 75%, for example about 80%, such as about 84% or about 85%, within about 120 minutes.

In criterion c) of step (i) of the method, the amount of budesonide released may be from about 70% to about 100%, such as from about 75% to about 100%, for example from about 84% to about 100%, such as from about 85% to 100%, within about 120 minutes.

In criterion b) of step (i) of the method, the composition may further fulfil the requirement that no more than about 10% of the budesonide is released into the pharmaceutically-relevant dissolution medium within about 37.5 minutes, such as no more than about 5%, for example no more than about 2.5% of the budesonide is released into the pharmaceutically-relevant dissolution medium within about 37.5 minutes. For example, the amount of budesonide released into the pharmaceutically-relevant dissolution medium may be from about 0% to about 10%, such as from about 0% to about 5%, for example from about 0% to about 2.5%, within about 37.5 minutes. Optionally, the release within about 37.5 minutes is in the absence of surfactant in the dissolution medium and at a paddle rotation speed of the Paddle Apparatus 2 of 50 rpm.

In criterion b) of step (i) of the method, the composition may further fulfil the requirement that at least about 20% of the budesonide is released into the pharmaceutically-relevant dissolution medium within about 75 minutes, such at least about 21%, for example at least about 22% or 23% of the budesonide is released into the pharmaceutically-relevant dissolution medium within about 75 minutes. For example, the amount of budesonide released into the pharmaceutically-relevant dissolution medium may be from about 23% to about 74% within about 75 minutes. Optionally, the release within about 75 minutes is in the absence of surfactant in the dissolution medium and at a paddle rotation speed of the Paddle Apparatus 2 of 50 rpm.

In criterion c) of the method, the composition may further fulfil the requirement that at least about 75% of the budesonide is released into the pharmaceutically-relevant dissolution medium within about 150 minutes, such at least about 76%, for example at least about 77% of the budesonide is released into the pharmaceutically-relevant dissolution medium within about 150 minutes. For example, the amount of budesonide released into the pharmaceutically-relevant dissolution medium may be from about 77% to about 100% within about 150 minutes. Optionally, the release within about 150 minutes is in the absence of surfactant in the dissolution medium and at a paddle rotation speed of the Paddle Apparatus 2 of 50 rpm.

In criterion b) of the method, the composition may further fulfil the requirement that no more than about 10% of the budesonide is released into the into the pharmaceutically-relevant dissolution medium within about 45 minutes, such as no more than about 5%, such as no more than about 2.5% of the budesonide is released into the pharmaceutically-relevant dissolution medium within about 45 minutes. For example, the amount of budesonide released into the pharmaceutically-relevant dissolution medium may be from about 0% to about 10%, such as from about 0% to about 5%, for example from about 0% to about 2.5% within about 45 minutes. Optionally, the release within about 45 minutes is in the absence of surfactant in the pharmaceutically-relevant dissolution medium and at a paddle rotation speed of the Paddle Apparatus 2 of 50, 75 or 100 rpm.

In criterion b) of the method, the composition may further fulfil the requirement that no more than about 10% of the budesonide is released into the pharmaceutically-relevant dissolution medium within about 60 minutes, such as no more than about 5%, such as no more than about 2.5% of the budesonide is released into the pharmaceutically-relevant dissolution medium within about 60 minutes. For example, the amount of budesonide released into the pharmaceutically-relevant dissolution medium may be from about 0% to about 10%, such as from about 0% to about 5%, for example from about 0% to about 2.5% within about 60 minutes. Optionally, the release within about 60 minutes is in the absence of surfactant in the pharmaceutically-relevant dissolution medium and at a paddle rotation speed of the Paddle Apparatus 2 of 50, 75 or 100 rpm.

In criterion b) of the method, the composition may further fulfil the requirement that from 50 to 90% of the budesonide is released into the pharmaceutically-relevant dissolution medium within about 90 minutes. Optionally, the release within about 90 minutes is in the absence of surfactant in the pharmaceutically-relevant dissolution medium and at a paddle rotation speed of the Paddle Apparatus 2 of 50, 75 or 100 rpm.

In criterion c) of the method, the composition may further fulfil the requirement that at least about 80% of the budesonide is released into the pharmaceutically-relevant dissolution medium within about 180 minutes, such at least about 85%, for example about 80% to about 100%, or about 85% to about 100% of the budesonide is released into the pharmaceutically-relevant dissolution medium within about 180 minutes. Optionally, the release within about 180 minutes is in the absence of surfactant in the pharmaceutically-relevant dissolution medium and at a paddle rotation speed of the Paddle Apparatus 2 of 50, 75 or 100 rpm.

In criterion c) of the method, the composition may further fulfil the requirement that at least about 85% of the budesonide is released into the pharmaceutically-relevant dissolution medium within about 240 minutes, such at least about 90%, for example about 90% to about 100% of the budesonide is released into the pharmaceutically-relevant dissolution medium within about 240 minutes. Optionally, the release within about 240 minutes is in the absence of surfactant in the pharmaceutically-relevant dissolution medium and at a paddle rotation speed of the Paddle Apparatus 2 of 50, 75 or 100 rpm.

In criterion c) of the method, the composition may further fulfil the requirement that at least about 90% of the budesonide is released into the pharmaceutically-relevant dissolution medium within about 360 minutes, such at least about 95%, for example about 95% to about 100% of the budesonide is released into the pharmaceutically-relevant dissolution medium within about 360 minutes. Optionally, the release within about 360 minutes is in the absence of surfactant in the pharmaceutically-relevant dissolution medium and at a paddle rotation speed of the Paddle Apparatus 2 of 50, 75 or 100 rpm.

In criterion c) of the method, the composition may further fulfil the requirement that at least about 90% of the budesonide is released into the pharmaceutically-relevant dissolution medium within about 480 minutes, such at least about 95%, for example about 95% to about 100% of the budesonide is released into the pharmaceutically-relevant dissolution medium within about 480 minutes. Optionally, the release within about 480 minutes is in the absence of surfactant in the pharmaceutically-relevant dissolution medium and at a paddle rotation speed of the Paddle Apparatus 2 of 50, 75 or 100 rpm.

In criterion c) of the method, the composition may further fulfil the requirement that at least about 90% of the budesonide is released into the pharmaceutically-relevant dissolution medium within about 600 minutes, such at least about 95%, for example about 95% to about 100% of the budesonide is released into the pharmaceutically-relevant dissolution medium within about 600 minutes. Optionally, the release within about 600 minutes is in the absence of surfactant in the pharmaceutically-relevant dissolution medium and at a paddle rotation speed of the Paddle Apparatus 2 of 50, 75 or 100 rpm.

In an embodiment, in criterion a) of step (i) of the method the dissolution in the acid resistance medium may be assessed according to the acceptance criteria in Acceptance Table 2 and/or Acceptance Table 3 of USP<711>/Table 2.9.3-2 and/or Table 2.9.3.-3 of Ph.Eur. 2.9.3.

In an embodiment, in criterion b) of step (i) of the method the dissolution in the pharmaceutically-relevant dissolution medium may be assessed according to the acceptance criteria in Acceptance Table 2 and/or Acceptance Table 3 of USP<711>/Table 2.9.3-2 and/or Table 2.9.3.-3 of Ph.Eur. 2.9.3.

In an embodiment, in criterion c) of step (i) of the method the dissolution in the pharmaceutically-relevant dissolution medium may be assessed according to the acceptance criteria in Acceptance Table 2 and/or Acceptance Table 4 of USP<711>/Table 2.9.3-2 and/or Table 2.9.3.-4 of Ph.Eur. 2.9.3.

For the avoidance of doubt, the amount of budesonide released in criterion b) at 30 minutes and criterion c) at 120 minutes is achieved in the presence and in the absence of added surfactant, such as added polysorbate 80 (e.g. Tween 80) at a concentration of about 0.5 mg/mL in the pharmaceutically-relevant dissolution medium. In addition, the amount of budesonide released at 37.5 minutes, 60 minutes, 75 minutes, 90 minutes and 150 minutes is achieved in the presence and in the absence of added surfactant, such as added polysorbate 80 (e.g. Tween 80) at a concentration of about 0.5 mg/mL in the pharmaceutically-relevant dissolution medium.

In an embodiment the method comprises:
(i) identifying a pharmaceutically acceptable composition intended to treat IgA nephropathy comprising budesonide and one or more pharmaceutically-acceptable excipients that provide for a modified release of said budesonide after administration to the gastrointestinal tract, which composition fulfils the following requirements in a standard in vitro USP<711>/Ph.Eur. 2.9.3 dissolution test using a dissolution apparatus according to Apparatus 2 (Paddle Apparatus) of said test (as described hereinafter) operated at 50 rpm;
  (a) the composition fulfils the requirement that no more than about 10% of the budesonide is released into the dissolution medium within about 120 minutes, when the dissolution medium is aqueous and has a pH of about 1.2;
  (b) the composition fulfils the requirement that no more than about 10% of the budesonide is released into a pharmaceutically-relevant dissolution medium within about 30 minutes, when the pharmaceutically-relevant dissolution medium is without surfactant;
  (c) the composition fulfils the requirement that no more than about 10% of the budesonide is released into the pharmaceutically-relevant dissolution medium within about 37.5 minutes, when the pharmaceutically-relevant dissolution medium is without surfactant;
  (d) the composition fulfils the requirement that from about 23% to about 74% of the budesonide is released into the pharmaceutically-relevant dissolution medium within about 75 minutes, when the pharmaceutically-relevant dissolution medium is without surfactant;
  (e) the composition fulfils the requirement that at least about 77% of the budesonide is released into the pharmaceutically-relevant dissolution medium within about 150 minutes, when the pharmaceutically-relevant dissolution medium is without surfactant; optionally
  (f) wherein the composition fulfils the requirement that at least about 70% of the budesonide is released into the pharmaceutically-relevant dissolution medium within about 120 minutes, when the pharmaceutically-relevant dissolution medium is without surfactant.

In another embodiment the method comprises:
(i) identifying a pharmaceutically acceptable composition intended to treat IgA nephropathy comprising budesonide and one or more pharmaceutically-acceptable excipients that provide for a modified release of said budesonide after administration to the gastrointestinal tract, which composition fulfils the following requirements in a standard in vitro USP<711>/Ph.Eur. 2.9.3 dissolution test using a dissolution apparatus according to Apparatus 2 (Paddle Apparatus) of said test (as described hereinafter) operated at 100 rpm;
  (a) the composition fulfils the requirement that no more than about 10% of the budesonide is released into the dissolution medium within about 120 minutes, when the dissolution medium is aqueous and has a pH of about 1.2;
  (b) the composition fulfils the requirement that no more than about 10% of the budesonide is released into a pharmaceutically-relevant dissolution medium within about 30 minutes, when the pharmaceutically-relevant dissolution medium is without surfactant;
  (c) the composition fulfils the requirement that no more than about 10% of the budesonide is released into the pharmaceutically-relevant dissolution medium within about 60 minutes, when the pharmaceutically-relevant dissolution medium is without surfactant;
  (d) the composition fulfils the requirement that from about 50% to about 90% of the budesonide is released into the pharmaceutically-relevant dissolution medium within about 90 minutes, when the pharmaceutically-relevant dissolution medium is without surfactant; and
  (e) the composition fulfils the requirement that at least about 70%, for example at least 75%, of the budesonide is released into the pharmaceutically-relevant dissolution medium within about 120 minutes, when the pharmaceutically-relevant t dissolution medium is without surfactant.

It is known from pharmacokinetic studies of drug absorption in the fasted state, that ingesting 200 to 250 mL of water along with a dosage form, a maximum total volume of about 300 to 500 mL will be available in the proximal small intestine (see Klein, *AAPS J.*, 12, 397, (2010)). Therefore, the dissolution tests that are employed in the method of the invention should employ volumes of dissolution media that is at least about 500 mL (e.g. about 900 mL). The initial volume of dissolution media used in criteria a), b) and c) may be about 900 mL.

The procedure used for testing the composition may be essentially in accordance with delayed-release solid dosage forms Method B of USP<711>/Ph.Eur. 2.9.3.

The temperature of the dissolution media in criteria a), b) and c) may be held at about 37° C.±0.5° C.

The number of compositions tested may be 6, or greater than 6, such as 12 or 24.

At each time point in criteria (a), (b) and (c) the amount of volume withdrawn from the dissolution medium may be 10 mL or 15 mL, optionally the volume withdrawn is not replaced. The withdrawal of dissolution medium does not affect the overall dissolution profile of the composition. That is to say, preferably the dissolution test is operated under sink conditions and that the amount of solvent outweighs that of the solute meaning that the withdrawal of a small amount for analysis purposes does not affect the dissolution.

Release in Medium at pH 6.8

According to an alternative aspect of the invention, there is provided a method of treatment of IgA nephropathy, which method comprises:

(i) identifying a pharmaceutically acceptable composition intended to treat IgA nephropathy comprising budesonide and one or more pharmaceutically-acceptable excipients that provide for a modified release of said budesonide after administration to the gastrointestinal tract, which composition fulfils the following requirements in a standard in vitro USP<711>/Ph.Eur. 2.9.3 dissolution test using a dissolution apparatus according to Apparatus 2 (Paddle Apparatus) of said test (as described hereinafter);
   (a) the composition fulfils the requirement that no more than about 10% of the budesonide is released into the dissolution medium within about 120 minutes, when the dissolution medium is aqueous and has a pH of about 1.2;
   (b) the composition fulfils the requirement that no more than about 10% of the budesonide is released into the dissolution medium within about 30 minutes, when the dissolution medium is aqueous and has a pH of about 6.8; and
   (c) the composition fulfils the requirement that at least about 70% of the budesonide is released into the dissolution medium within about 120 minutes, when the dissolution medium is aqueous and has a pH of about 6.8, then
(ii) administering said composition to a patient with IgA nephropathy in need of said treatment, and which method is referred to hereinafter as "the method of the invention".

The method of the invention may comprise (I) combining budesonide with one or more pharmaceutically-acceptable excipients that provide for a modified release of said budesonide after administration to the gastrointestinal tract to make a pharmaceutically-acceptable composition intended to treat IgA nephropathy, and then (II) testing the composition in the standard in vitro USP<711>/Ph.Eur. 2.9.3 dissolution test as set out above and, if the composition fulfils the requirements (a) to (c) as set out above (i.e. in relation to release in medium at pH 6.8), administering said composition to a patient with IgA nephropathy in need of said treatment.

As an alternative embodiment, there is provided a composition comprising a combination of budesonide with one or more pharmaceutically-acceptable excipients that provide for a modified release of said budesonide after administration to the gastrointestinal tract, wherein said composition fulfils the dissolution profile of step (i) outlined above (i.e. in relation to release in the above pharmaceutically-relevant medium at pH 6.8) for use in the treatment of IgA nephropathy.

As a further alternative embodiment, there is provided the use of a composition comprising a combination of budesonide with one or more pharmaceutically-acceptable excipients that provide for a modified release of said budesonide after administration to the gastrointestinal tract, wherein said composition fulfils the dissolution profile of step (i) outlined above (i.e. in relation to release in the pharmaceutically-relevant medium at pH 6.8) for the manufacture of a medicament for the treatment of IgA nephropathy.

For the avoidance of doubt, step (ii) of administering the composition to a patient will only take place if the average (mean) of the tested compositions fulfils all of criteria (a), (b) and (c) of step (i).

The Paddle Apparatus of Apparatus 2 may be operated at about 50 revolutions per minute (rpm), about 75 rpm or about 100 rpm. Preferably, the Paddle Apparatus of Apparatus 2 is operated at about 100 rpm, or at about 50 rpm.

The aqueous dissolution medium of criterion b) and criterion c) may comprise a surfactant in an amount of about 0.5 mg/mL (0.05% w/v). The surfactant may be a polysorbate, preferably wherein the surfactant is polysorbate 80 (e.g., Tween 80).

The aqueous dissolution medium of criterion b) and criterion c) may be a phosphate buffer medium, such as a sodium phosphate buffer solution at a concentration of about 50 mM.

The phosphate buffer medium at a pH of about 6.8 may be prepared by first preparing a 0.2 M sodium phosphate tribasic solution, then adding one part of the 0.2 M sodium phosphate tribasic solution to three parts of a 0.1 N hydrochloric acid solution. After mixing the two solutions together, the pH may be checked and adjusted if necessary to a pH of about 6.8 by adding either hydrochloric acid or sodium hydroxide.

In criterion a) of step (i) of the method the amount of budesonide released may be no more than about 5%, such as no more than about 2.5%, within about 120 minutes.

In criterion a) of step (i) of the method, the amount of budesonide released may be from about 0% to about 10%, such as from about 0% to about 5%, for example from about 0% to about 2.5%, within about 120 minutes.

In criterion b) of step (i) of the method the amount of budesonide released may be no more than about 5%, such as no more than about 2.5%, within about 30 minutes.

In criterion b) of step (i) of the method, the amount of budesonide released may be from about 0% to about 10%, such as from about 0% to about 5%, for example from about 0% to about 2.5%, within about 30 minutes.

In criterion c) of step (i) of the method the amount of budesonide released may be at least about 75%, for example about 80%, such as about 84% or about 85%, within about 120 minutes.

In criterion c) of step (i) of the method, the amount of budesonide released may from about 70% to about 100%, such as from about 75% to about 100%, for example from about 84% to about 100%, such as from about 85% to 100%, within about 120 minutes.

In criterion b) of step (i) of the method, the composition may further fulfil the requirement that no more than about 10% of the budesonide is released into the dissolution medium within about 37.5 minutes when the dissolution medium is aqueous and has a pH of about 6.8, such as no more than about 5%, for example no more than about 2.5% of the budesonide is released within about 37.5 minutes when the dissolution medium is aqueous and has a pH of about 6.8. For example, the amount of budesonide released may be from about 0% to about 10%, such as from about 0% to about 5%, for example from about 0% to about 2.5%, within about 37.5 minutes when the dissolution medium is aqueous and has a pH of about 6.8. Optionally, the release within about 37.5 minutes is in the absence of surfactant in the dissolution medium and at a paddle rotation speed of the Paddle Apparatus 2 of 50 rpm.

In criterion b) of step (i) of the method, the composition may further fulfil the requirement that at least about 20% of the budesonide is released into the dissolution medium within about 75 minutes when the dissolution medium is aqueous and has a pH of about 6.8, such at least about 21%, for example at least about 22% or 23% of the budesonide is released within about 75 minutes when the dissolution medium is aqueous and has a pH of about 6.8. For example, the amount of budesonide released may be from about 23% to about 74% within about 75 minutes when the dissolution medium is aqueous and has a pH of about 6.8. Optionally, the release within about 75 minutes is in the absence of surfactant in the dissolution medium and at a paddle rotation speed of the Paddle Apparatus 2 of 50 rpm.

In criterion c) of the method, the composition may further fulfil the requirement that at least about 75% of the budesonide is released into the dissolution medium within about 150 minutes when the dissolution medium is aqueous and has a pH of about 6.8, such at least about 76%, for example at least about 77% of the budesonide is released within about 150 minutes when the dissolution medium is aqueous and has a pH of about 6.8. For example, the amount of budesonide released may be from about 77% to about 100% within about 150 minutes when the dissolution medium is aqueous and has a pH of about 6.8. Optionally, the release within about 150 minutes is in the absence of surfactant in the dissolution medium and at a paddle rotation speed of the Paddle Apparatus 2 of 50 rpm.

In criterion b) of the method, the composition may further fulfil the requirement that no more than about 10% of the budesonide is released into the dissolution medium within about 60 minutes when the dissolution medium is aqueous and has a pH of about 6.8, such as no more than about 5%, such as no more than about 2.5% of the budesonide is released within about 60 minutes when the dissolution medium is aqueous and has a pH of about 6.8. For example, the amount of budesonide released may be from about 0% to about 10%, such as from about 0% to about 5%, for example from about 0% to about 2.5% within about 60 minutes when the dissolution medium is aqueous and has a pH of about 6.8. Optionally, the release within about 60 minutes is in the absence of surfactant in the dissolution medium and at a paddle rotation speed of the Paddle Apparatus 2 of 100 rpm.

In criterion b) of the method, the composition may further fulfil the requirement that from 50 to 90% of the budesonide is released within about 90 minutes when the dissolution medium is aqueous and has a pH of about 6.8. Optionally, the release within about 90 minutes is in the absence of surfactant in the dissolution medium and at a paddle rotation speed of the Paddle Apparatus 2 of 100 rpm.

In an embodiment, in criterion a) of step (i) of the method the dissolution in the acid resistance medium may be assessed according to the acceptance criteria in Acceptance Table 2 and/or Acceptance Table 3 of USP<711>/Table 2.9.3-2 and/or Table 2.9.3.-3 of Ph.Eur. 2.9.3.

In an embodiment, in criterion b) of step (i) of the method the dissolution in the buffer stage medium may be assessed according to the acceptance criteria in Acceptance Table 2 and/or Acceptance Table 3 of USP<711>/Table 2.9.3-2 and/or Table 2.9.3.-3 of Ph.Eur. 2.9.3.

In an embodiment, in criterion c) of step (i) of the method the dissolution in the buffer stage medium may be assessed according to the acceptance criteria in Acceptance Table 2 and/or Acceptance Table 4 of USP<711>/Table 2.9.3-2 and/or Table 2.9.3.-4 of Ph.Eur. 2.9.3.

For the avoidance of doubt, the amount of budesonide released in criterion b) at 30 minutes and criterion c) at 120 minutes is achieved in the presence and in the absence of added surfactant, such as added polysorbate 80 (e.g. Tween 80) at a concentration of about 0.5 mg/mL in the dissolution medium. In addition, the amount of budesonide released at 37.5 minutes, 60 minutes, 75 minutes, 90 minutes and 150 minutes is achieved in the presence and in the absence of added surfactant, such as added polysorbate 80 (e.g. Tween 80) at a concentration of about 0.5 mg/mL in the dissolution medium.

In an embodiment the method comprises:
(i) identifying a pharmaceutically acceptable composition intended to treat IgA nephropathy comprising budesonide and one or more pharmaceutically-acceptable excipients that provide for a modified release of said budesonide after administration to the gastrointestinal tract, which composition fulfils the following requirements in a standard in vitro USP<711>/Ph.Eur. 2.9.3 dissolution test using a dissolution apparatus according to Apparatus 2 (Paddle Apparatus) of said test (as described hereinafter) operated at 50 rpm;
  (a) the composition fulfils the requirement that no more than about 10% of the budesonide is released into the dissolution medium within about 120 minutes, when the dissolution medium is aqueous and has a pH of about 1.2;
  (b) the composition fulfils the requirement that no more than about 10% of the budesonide is released into the dissolution medium within about 30 minutes, when the dissolution medium is aqueous, without surfactant and has a pH of about 6.8;
  (c) the composition fulfils the requirement that no more than about 10% of the budesonide is released into the dissolution medium within about 37.5 minutes, when the dissolution medium is aqueous, without surfactant and has a pH of about 6.8
  (d) the composition fulfils the requirement that from about 23% to about 74% of the budesonide is released into the dissolution medium within about 75 minutes, when the dissolution medium is aqueous, without surfactant and has a pH of about 6.8;
  (e) the composition fulfils the requirement that at least about 77% of the budesonide is released into the dissolution medium within about 150 minutes, when the dissolution medium is aqueous, without surfactant and has a pH of about 6.8; optionally
  (f) wherein the composition fulfils the requirement that at least about 70% of the budesonide is released into the dissolution medium within about 120 minutes, when the dissolution medium is aqueous, without surfactant and has a pH of about 6.8.

In another embodiment the method comprises:
(i) identifying a pharmaceutically acceptable composition intended to treat IgA nephropathy comprising budesonide and one or more pharmaceutically-acceptable excipients that provide for a modified release of said budesonide after administration to the gastrointestinal tract, which composition fulfils the following requirements in a standard in vitro USP<711>/Ph.Eur. 2.9.3 dissolution test using a dissolution apparatus according to Apparatus 2 (Paddle Apparatus) of said test (as described hereinafter) operated at 100 rpm;
  (a) the composition fulfils the requirement that no more than about 10% of the budesonide is released into the dissolution medium within about 120 minutes, when the dissolution medium is aqueous and has a pH of about 1.2;

(b) the composition fulfils the requirement that no more than about 10% of the budesonide is released into the dissolution medium within about 30 minutes, when the dissolution medium is aqueous, without surfactant and has a pH of about 6.8;

(c) the composition fulfils the requirement that no more than about 10% of the budesonide is released into the dissolution medium within about 60 minutes, when the dissolution medium is aqueous, without surfactant and has a pH of about 6.8;

(d) the composition fulfils the requirement that from about 50% to about 90% of the budesonide is released into the dissolution medium within about 90 minutes, when the dissolution medium is aqueous, without surfactant and has a pH of about 6.8; and (e) the composition fulfils the requirement that at least about 70%, for example at least 75%, of the budesonide is released into the dissolution medium within about 120 minutes, when the dissolution medium is aqueous, without surfactant and has a pH of about 6.8.

It is known from pharmacokinetic studies of drug absorption in the fasted state, that ingesting 200 to 250 mL of water along with a dosage form, a maximum total volume of about 300 to 500 mL will be available in the proximal small intestine (see Klein, *AAPS J.*, 12, 397, (2010)). Therefore, the dissolution tests that are employed in the method of the invention should employ volumes of dissolution media that is at least about 500 mL (e.g. about 900 mL). The initial volume of dissolution media used in criteria a), b) and c) may be about 900 mL.

The procedure used for testing the composition may be essentially in accordance with prolonged-release and/or delayed-release solid dosage forms Method B of USP<711>/Ph.Eur. 2.9.3.

The temperature of the dissolution media in criteria a), b) and c) may be held at about 37° C.±0.5° C.

The number of compositions tested may be 6, or greater than 6, such as 12 or 24.

At each time point in criteria (a), (b) and (c) the amount of volume withdrawn from the dissolution medium may be 10 mL or 15 mL, optionally the volume withdrawn is not replaced. The withdrawal of dissolution medium does not affect the overall dissolution profile of the composition. That is to say, preferably the dissolution test is operated under sink conditions and that the amount of solvent outweighs that of the solute meaning that the withdrawal of a small amount for analysis purposes does not affect the dissolution.

Release in Level 1 Fasted State Simulated Intestinal Fluid at a pH of about 6.5

According to a further alternative aspect of the invention, there is provided a method of treatment of IgA nephropathy, which method comprises:

(i) identifying a pharmaceutically acceptable composition intended to treat IgA nephropathy comprising budesonide and one or more pharmaceutically-acceptable excipients that provide for a modified release of said budesonide after administration to the gastrointestinal tract, which composition fulfils the following requirements in a standard in vitro USP<711>/Ph.Eur. 2.9.3 dissolution test using a dissolution apparatus according to Apparatus 2 (Paddle Apparatus) of said test;

(a) the composition fulfils the requirement that no more than about 10% of the budesonide is released into the dissolution medium within about 120 minutes, when the dissolution medium is aqueous and has a pH of about 1.2; and (b) the composition fulfils the requirement that no more than about 10% of the budesonide is released into a dissolution medium comprising Level 1 fasted state simulated intestinal fluid at a pH of about 6.5 within about 30 minutes; and (c) the composition fulfils the requirement that at least about 70% of the budesonide is released into a dissolution medium comprising Level 1 fasted state simulated intestinal fluid at a pH of about 6.5 within about 120 minutes; then (ii) administering said composition to a patient with IgA nephropathy in need of said treatment, and which method is referred to hereinafter as "the method of the invention".

The method of the invention may comprise (I) combining budesonide with one or more pharmaceutically acceptable excipients that provide for a modified release of said budesonide after administration to the gastrointestinal tract to make a pharmaceutically acceptable composition intended to treat IgA nephropathy, and then (II) testing the composition in the standard in vitro USP<711>/Ph.Eur. 2.9.3 dissolution test as set out above and, if the composition fulfils the requirements (a) to (c) as set out above (i.e. in relation to release in Level 1 fasted state simulated intestinal fluid at a pH of about 6.5), administering said composition to a patient with IgA nephropathy in need of said treatment.

As an alternative embodiment, there is provided a composition comprising a combination of budesonide with one or more pharmaceutically-acceptable excipients that provide for a modified release of said budesonide after administration to the gastrointestinal tract, wherein said composition fulfils the dissolution profile of step (i) outlined above (i.e. in relation to release in Level 1 fasted state simulated intestinal fluid at a pH of about 6.5) for use in the treatment of IgA nephropathy.

As a further alternative embodiment, there is provided the use of a composition comprising a combination of budesonide with one or more pharmaceutically-acceptable excipients that provide for a modified release of said budesonide after administration to the gastrointestinal tract, wherein said composition fulfils the dissolution profile of step (i) outlined above (i.e. in relation to release in Level 1 fasted state simulated intestinal fluid at a pH of about 6.5) for the manufacture of a medicament for the treatment of IgA nephropathy.

As referred to herein, the term "treatment" of IgA nephropathy, we further include the prophylaxis, or the diagnosis of the relevant condition in addition to therapeutic, symptomatic and/or palliative treatment.

The term 'Level 1 fasted state simulated intestinal fluid' (Level 1 FaSSIF-V1) will be understood by those skilled in the art to include a biorelevant dissolution medium that has a lower pH and buffering capacity than standard simulated intestinal fluid (the medium that is typically employed in standard USP/Ph.Eur. tests; pH 6.8), and which has been developed specifically to simulate fasting conditions in the proximal small intestine (see, for example, Markopoulous et al, In-vitro simulation of luminal conditions for evaluation of performance of oral drug products: Choosing the appropriate test media, *European Journal of Pharmaceutics and Biopharmaceutics*, 93, 2015, 173-182).

Level 1 FaSSIF-V1 comprises a phosphate buffer system, such as one comprising $NaH_2PO_4$ (at a concentration of about 28.5 mM), NaOH (at a concentration of about 13.8 mM), HCl (qs) and deionized water (qs), which produces a medium with an osmolality of about 270 mOsmol/kg and a buffer capacity of about 12 mEq/pH/L.

Surfactant may be added to the FaSSIF medium in the present method of the invention. The surfactant may be a polysorbate, such as polysorbate 80 (e.g. Tween 80). The surfactant may be present at a concentration of about 0.05% w/v (0.5 mg/mL) to facilitate the analysis.

Thus, there is further provided:

the method of the invention as hereinbefore defined;

a composition that fulfils the dissolution profile of step (i) outlined above for use in the treatment of IgA nephropathy; and the use of a composition that fulfils the dissolution profile of step (i) outlined above for the manufacture of a medicament for the treatment of IgA nephropathy, provided that, in each case, the FaSSIF medium employed in step (i) comprises a surfactant, such as a polysorbate, including polysorbate 80 (e.g. Tween 80), optionally present at a concentration of about 0.05% w/v (0.5 mg/mL) to facilitate the analysis.

For the avoidance of doubt, step (ii) of administering the composition to a patient will only take place if the average (mean) of the tested compositions fulfils all of criteria (a), (b) and (c) of step (i).

In criterion a) of step (i) of the method, the amount of budesonide released may be no more than about 5%, such as no more than about 2.5%, within about 120 minutes.

In criterion a) of step (i) of the method, the amount of budesonide released may be from about 0% to about 10%, such as from about 0% to about 5%, for example from about 0% to about 2.5%, within about 120 minutes.

In criterion b) of step (i) of the method, the amount of budesonide released may be no more than about 5%, such as no more than about 2.5%, within about 30 minutes.

In criterion b) of step (i) of the method, the amount of budesonide released may be from about 0% to about 10%, such as from about 0% to about 5%, for example from about 0% to about 2.5%, within about 30 minutes.

In criterion c) of step (i) of the method, the amount of budesonide released may be at least about 75%, for example about 80%, such as about 84% or about 85%, within about 120 minutes.

In criterion c) of step (i) of the method, the amount of budesonide released may be from about 70% to about 99%, such as from about 70% to about 90%, within about 120 minutes.

For the avoidance of doubt, the amount of budesonide released in criterion b) at 30 minutes and criterion c) at 120 minutes is achieved in the presence and in the absence of added polysorbate 80 (e.g. Tween 80) at a concentration of about 0.05% w/v (about 0.5 mg/mL) in the FaSSIF medium.

In criterion b) of step (i) of the method, the composition may further fulfil the requirement that no more than about 10% of the budesonide is released into the dissolution medium within about 60 minutes, such as no more than about 5%, for example no more than about 2.5% of the budesonide is released within about 60 minutes. For example, the amount of budesonide released may be from about 0% to about 10%, such as from about 0% to about 5%, for example from about 0% to about 2.5%, within about 60 minutes. The amount of budesonide released within about 60 minutes is achieved in the presence and absence of added polysorbate 80 (e.g. Tween 80) at a concentration of about 0.05% w/v (about 0.5 mg/mL) in the FaSSIF medium.

In criterion c) of step (i) of the method, in the presence of added polysorbate 80 (e.g. Tween 80) at a concentration of about 0.05% w/v (about 0.5 mg/mL) in the FaSSIF medium, the composition may further fulfil the requirement that at least about 20%, for example 25%, or 30%, such as 35% of the budesonide is released into the dissolution medium, for example at least about 40% of the budesonide is released, such as from about 30 to about 65% of the budesonide is released, such as about 35% to about 65% of the budesonide is released, including from about 40% to about 60% of the budesonide is released, for example from about 45% to about 55% of the budesonide is released into the dissolution medium, within about 90 minutes.

In criterion c) of step (i) of the method, in the absence of added polysorbate 80 (e.g. Tween 80) at a concentration of about 0.05% (about 0.5 mg/mL) w/v in the FaSSIF medium, the composition may further fulfil the requirement that at least about 10%, for example at least about 15% of the budesonide is released, such as from about 10 to about 50% of the budesonide is released, such as about 10% to about 40% of the budesonide is released, including from about 10% to about 30% of the budesonide is released, for example from about 15% to about 30% of the budesonide is released into the dissolution medium, within about 90 minutes.

In criterion c) of step (i) of the method, the composition may further fulfil the requirement that at least about 90% of the budesonide is released into the dissolution medium within about 180 minutes, for example at least about 95% of the budesonide is released within about 180 minutes. The amount of budesonide released within about 180 minutes is achieved in the presence and in the absence of added polysorbate 80 (e.g. Tween 80) at a concentration of about 0.05% w/v (about 0.5 mg/mL) in the FaSSIF medium.

The Paddle Apparatus of Apparatus 2 may be operated at about 50 rpm, about 75 rpm or about 100 rpm. Preferably, the Paddle Apparatus of Apparatus 2 is operated at about 100 rpm.

It is known from pharmacokinetic studies of drug absorption in the fasted state, that ingesting 200 to 250 mL of water along with a dosage form, a maximum total volume of about 300 to 500 mL will be available in the proximal small intestine (see Klein, *AAPS J.*, 12, 397, (2010)). Therefore, the dissolution tests that are employed in the method of the invention should employ volumes of dissolution media (including FaSSIF) that is at least about 500 mL (e.g. about 900 mL). Preferably, the initial volume of dissolution media used in criteria a), b) and c) is about 900 mL.

The procedure used for testing the composition may be essentially in accordance with delayed-release solid dosage forms Method B of USP<711>/Ph.Eur. 2.9.3.

The temperature of the dissolution media in criteria a), b) and c) may be held at about 37° C.±0.5° C.

The number of compositions tested may be at least 3, such as 6, or greater than 6, such as 12 or 24.

At each time point in criteria (a), (b) and (c) the amount of volume withdrawn from the dissolution medium may be 10 mL or 15 mL, optionally the volume withdrawn is not replaced. The withdrawal of dissolution medium does not affect the overall dissolution profile of the composition. That is to say, preferably the dissolution test is operated under sink conditions and that the amount of solvent outweighs that of the solute meaning that the withdrawal of a small amount for analysis purposes does not affect the dissolution.

Particularly, but not exclusively, when the composition of the invention is a core-shell composition as defined below, the method of the invention as defined herein may comprise the additional steps of:

(1) providing budesonide with the same extended release excipients, but in the absence of the delayed release excipients, as described herein; and (2) identifying that the composition in a standard in vitro USP<711>/Ph.Eur. 2.9.3 dissolution test using a dissolution apparatus according to Apparatus 2 (Paddle Apparatus) of said test, fulfils the requirement that from about 20 to about 60%, such as from about 25 to about 50%, of the budesonide is released into a dissolution medium comprising Level 1 fasted state simulated intestinal fluid at a pH of about 6.5 within about 15 minutes.

In an embodiment, from about 70 to about 90% of the budesonide is released into the Level 1 FaSSIF-V1 dissolution medium defined herein within about 30 minutes in the absence of the delayed release coating (e.g., without an enteric coating) and, more preferably, from about 75 and about 85% of the budesonide is released into that dissolution medium within about 45 minutes.

In the absence of the delayed release (e.g., enteric) coating, from about 80% to about 90% of the budesonide may be released into the Level 1 FaSSIF-V1 dissolution medium as defined herein within about 60 minutes, more especially, from about 90% (such as about 95% (including about 97% and about 100%) of the budesonide may be released into that dissolution medium within about 90 minutes, such as within about 120 minutes, including within about 180 minutes.

The budesonide composition in the absence of the delayed release excipients having the dissolution profile as described above is further confirmation that the bulk of the budesonide will be released in vivo to the ileum.

Effect on Biomarkers

The method of the invention, in all aspects outlined above, may lead to a statistically significant reduction in the level of serum B-cell activating factor (BAFF) (also known as tumour necrosis factor ligand superfamily member 13B (TNFSF13B)) in a subject relative to the baseline level of serum BAFF in the subject prior to treatment.

By "statistically significant reduction" we include the meaning of a reduction that is statistically significant to a p value<0.05 following use of a one-way Analysis of Variance (ANOVA) when comparing the change seen in the treated patient group with the change seen in patients who received a placebo.

By "relative to the baseline level" we include the meaning that the measured level of a molecule (e.g. BAFF) is lower than the level measured at the beginning of the study (i.e. prior to administration of a drug). The baseline level is the level immediately prior to the start of the treatment and is used as a comparator for subsequently measured levels (e.g. immediately following a course of treatment, or at a timepoint following conclusion of a course of treatment). Thus, such a reduction is specific for the subject or group of subjects in question and is not an absolute value.

The reduction in the serum level of BAFF in the subject may be at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, 96%, 97%, 98%, or 99% relative to the baseline serum level of BAFF in the subject prior to treatment. For example, the reduction in the serum level of BAFF in the subject may be at least about 5%. In particular the reduction in the level of serum BAFF in the subject may be at least about 10%, such as the reduction in the serum level of BAFF in the subject may be at least about 14%.

The reduction in the serum level of BAFF in the subject may be from about 1% to about 70%. For example, the reduction in the serum level of BAFF in the subject may be from about 5% to about 50%. In particular, the reduction in the serum level of BAFF in the subject may be from about 5% to about 25%, such as the reduction in the serum level of BAFF in the subject may be from about 10% to about 25%. For example, the reduction in the serum level of BAFF in the subject may be from about 14% to about 23%.

The statistically significant reduction in the level of serum BAFF observed following the method of the invention may be associated with a statistically significant reduction in the serum level of one or more biomarkers associated with B-cell activation and/or proliferation, relative to the serum baseline level of the one or more biomarkers in the subject prior to treatment. Reduction in the serum levels of one or more biomarkers associated with B-cell activation and/or proliferation would indicate a beneficial effect in the treatment of diseases in which overactivity, overabundance, and/or over-proliferation of B-cells is linked to pathogenicity. For example, a reduction in the serum level of a biomarker produced by an active and/or proliferating B-cell may indicate that the activity/proliferation of B-cells is reduced and may be an indicator of a beneficial effect in the treatment of diseases, such as IgAN, in which overactivity, overabundance, and/or over-proliferation of B-cells is linked to pathogenicity.

The one or more biomarkers may include: transmembrane activator and CAML interactor (TACI) (also known as tumour necrosis factor receptor superfamily member 13B (TNFRSF13B)); B-cell maturation antigen (BCMA) (also known as tumour necrosis factor receptor superfamily member 17 (TNFRSF17)); BAFF-R (also known as tumour necrosis factor receptor superfamily member 13C (TNFRSF13C)); CD27; CD30; C-X-C motif chemokine 12 (CXCL12); C-X-C motif chemokine 13 (CXCL13); Chemokine (C-C motif) ligand 19 (CCL19); Interleukin 2 (IL-2); Interleukin 6 (IL-6); Chemokine (C-C motif) ligand 3 (CCL3); Chemokine (C-C motif) ligand 4 (CCL4); soluble CD23 (sCD23); secretory IgA; IgA-IgG immune complexes; poorly O-galactosylated IgA1; or combinations thereof.

By "biomarker" (also known as "biological marker") we include the meaning of a measurable indicator of some biological state or condition. Often biomarkers are naturally occurring biological molecules, e.g. proteins, amino acids, antibodies, nucleic acids (e.g. RNA or DNA), nucleotides, lipids, carbohydrates/sugar, primary metabolites, or secondary metabolites. Such biomarkers can be associated with a particular pathological or physiological process, a disease, a pharmacological response to a drug, and may be used to predict disease incidence and prevalence, or to predict outcomes of disease and therapeutic intervention, etc.

The reduction in the serum level of the biomarker in the subject may be at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, 96%, 97%, 98%, or 99% relative to the baseline serum level of the biomarker in the subject prior to treatment. For example, the reduction in the serum level of the biomarker may be from about 1% to about 90%, or from about 5 to about 70%, or from about 10 to about 50%.

The reduction in the serum level of TACI in the subject may be at least about 1%, 2%, 3%, 4%, %, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 60%, 65%, 70%, or 75%, relative to the baseline serum level of TACI in the subject prior to treatment. For example, the reduction in the serum level of TACI in the subject may be at least about 5%. In particular, the reduction in the serum level of TACI in the subject may be at least about 11%.

The reduction in the serum level of TACI in the subject may be from about 1% to about 70%. For example, the reduction in the serum level of TACI in the subject may be from about 5% to about 50%. In particular, the reduction in the serum level of TACI in the subject may be from about 5% to about 20%, such as the reduction in the serum level of TACI in the subject may be from about 10% to about 20%. For example, the reduction in the serum level of TACI in the subject may be from about 11% to about 17%.

The reduction in the serum level of BCMA in the subject may be at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, or 60%, relative to the baseline serum level of BCMA in the subject prior to treatment. For example, the reduction in the serum level of BCMA in the subject may be at least about 1%. In particular, the reduction in the serum level of BCMA in the subject may be at least about 6%.

Furthermore, the reduction in the serum level of BCMA in the subject may be between about 1% and about 60%. For example, the reduction in the serum level of BCMA in the subject may be from about 1% to about 20%. In particular, the reduction in the serum level of BCMA in the subject may be from about 1% to about 10%, such as the reduction in the serum level of BCMA in the subject may be from about 5% to about 10%. For example, the reduction in the serum level of BCMA in the subject may be from about 6% to about 7%.

The reduction in the serum level of BAFF-R in the subject may be at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, 96%, 97%, 98%, or 99%, relative to the baseline serum level of BAFF-R in the subject prior to treatment.

The reduction in the serum level of CD27 in the subject may be at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, or 65%, relative to the baseline serum level of CD27 in the subject prior to treatment. For example, the reduction in the serum level of CD27 in the subject may be at least about 5%. In particular, the reduction in the serum level of CD27 in the subject may be at least about 10%, such as the reduction in the serum level of CD27 in the subject may be at least about 15%.

The reduction in the serum level of CD27 in the subject may be from about 1% to about 60%. For example, the reduction in the serum level of CD27 in the subject may be from about 1% to about 25%. In particular, the reduction in the serum level of CD27 in the subject may be from about 5% to about 25%, such as the reduction in the serum level of CD27 in the subject may be from about 10% to about 20%. For example, the reduction in the serum level of CD27 in the subject may be from about 15% to about 19%.

The reduction in the serum level of CD30 in the subject may be at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 40%, 45%, 50%, 55%, 60%, 65%, 70%, or 75%, relative to the baseline serum level of CD30 in the subject prior to treatment. For example, the reduction in the level of serum CD30 in the subject may be at least about 1%. In particular the reduction in the serum level of CD30 in the subject may be at least about 3%, such as the reduction in the serum level of CD30 in the subject may be at least about 5%.

The reduction in the serum level of CD30 in the subject may be from about 1% to about 75%. For example, the reduction in the serum level of CD30 in the subject may be from about 1% to about 25%. In particular, the reduction in the level of serum CD30 in the subject may be from about 1% to about 10%, such as the reduction in the serum level of CD30 in the subject may be from about 5% to about 10%. For example, the reduction in the serum level of CD30 in the subject may be from about 5% to about 8%.

The reduction in the serum level of secretory IgA in the subject may be at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 40%, 45%, 50%, 55%, 60%, 65%, 70%, or 75%, relative to the baseline serum level of secretory IgA in the subject prior to treatment. For example, the reduction in the serum level of secretory IgA in the subject may be at least about 1%. In particular the reduction in the serum level of secretory IgA in the subject may be at least about 2%, such as the reduction in the serum level of secretory IgA in the subject may be at least about 3%.

The reduction in the serum level of secretory IgA in the subject may be from about 1% to about 75%. For example, the reduction in the serum level of secretory IgA in the subject may be from about 1% to about 25%. In particular, the reduction in the level of serum secretory IgA in the subject may be from about 1% to about 10%, such as the reduction in the serum level of secretory IgA in the subject may be from about 1% to about 5%. For example, the reduction in the serum level of secretory IgA in the subject may be from about 1% to about 3%.

The reduction in the serum level of IgA-IgG immune complexes in the subject may be at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 40%, 45%, 50%, 55%, 60%, 65%, 70%, or 75%, relative to the baseline serum level of IgA-IgG immune complexes in the subject prior to treatment. For example, the reduction in the serum level of IgA-IgG immune complexes in the subject may be at least about 1%. In particular the reduction in the serum level of IgA-IgG immune complexes in the subject may be at least about 5%, such as the reduction in the serum level of IgA-IgG immune complexes in the subject may be at least about 8%.

The reduction in the serum level of IgA-IgG immune complexes in the subject may be from about 1% to about 75%. For example, the reduction in the serum level of IgA-IgG immune complexes in the subject may be from about 1% to about 25%. In particular, the reduction in the level of serum IgA-IgG immune complexes in the subject may be from about 1% to about 20%, such as the reduction in the serum level of IgA-IgG immune complexes in the subject may be from about 2% to about 20%. For example, the reduction in the serum level of IgA-IgG immune complexes in the subject may be from about 2% to about 15%.

The reduction in the serum level of poorly O-galactosylated IgA1 in the subject may be at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 40%, 45%, 50%, 55%, 60%, 65%, 70%, or 75%, relative to the baseline serum level of poorly O-galactosylated IgA1 in the subject prior to treatment. For example, the reduction in the serum level of poorly O-galactosylated IgA1 in the subject may be at least about 1%. In particular the reduction in the serum level of poorly O-galactosylated IgA1 in the subject may be at least about 5%, such as the reduction in the serum level of poorly O-galactosylated IgA1 in the subject may be at least about 8%.

The reduction in the serum level poorly O-galactosylated IgA1 in the subject may be from about 1% to about 75%. For example, the reduction in the serum level of poorly O-galactosylated IgA1 in the subject may be from about 1% to about 25%. In particular, the reduction in the level of serum poorly O-galactosylated IgA1 in the subject may be from about 1% to about 20%, such as the reduction in the serum level of poorly O-galactosylated IgA1 in the subject may be from about 2% to about 20%. For example, the reduction in the serum level of poorly O-galactosylated IgA1 in the subject may be from about 2% to about 15%.

The above-mentioned reduction in biomarkers is associated with the method of the invention, which requires that the budesonide-containing composition both exhibits a specified in vitro release profile and is intended for the treatment of, and/or capable of treating, IgAN.

As we have found that compositions exhibiting that in vitro release profile also exhibit appropriate reductions in the relevant biomarkers, this indicates that:
 budesonide is being released to the region of the gastrointestinal tract within which the Peyer's Patches are predominantly located (e.g. the ileum); and
 such compositions are accordingly capable of treating IgAN safely and efficaciously at an appropriate dose of budesonide.

Budesonide Containing Compositions

Compositions that may be employed in the method of the invention may comprise any combination of budesonide and one or more excipients that gives rise to the desired in vitro release profile in all aspects as described herein. This may be a combination of extended and/or delayed release coatings, which may be applied by a variety of formulative principles as described hereinafter.

In any event we prefer that compositions comprise at least one delayed release coating that is preferably located at the exterior of the composition to ensure that the active ingredient is not released within the stomach and/or until the small intestine is reached.

Such a delayed release coating may thus comprise a so-called "enteric coating", which refers to a material having gastroresistant properties, that is to say the material prevents dissolution or disintegration in a gastric environment, thus allowing the composition to pass through the stomach towards the ileum region of the small intestine.

The enteric coating may comprise azopolymers, disulphide polymers, cellulose acetate, cellulose acetate succinate, cellulose acetate phthalate, cellulose acetate tetrahydrophthalate, polyvinyl acetate phthalate, hydroxyethyl ethyl cellulose phthalate, methacrylic acid copolymers, polymethacrylic acid/acrylic acid copolymers, styrol maleic acid copolymers, hydroxypropyl methyl cellulose phthalate, acrylic resins, cellulose acetate trimellitate, hydroxypropyl methylcellulose trimellitate, shellac, hydroxyethyl ethyl cellulose phthalate, carboxymethylcellulose and hydroxypropyl methyl cellulose acetate succinate.

Particular enteric coating substances include cellulose acetate, cellulose acetate succinate, cellulose acetate phthalate, cellulose acetate tetrahydrophthalate, polyvinyl acetate phthalate, hydroxyethyl ethyl cellulose phthalate, methacrylic acid copolymers, polymethacrylic acid/acrylic acid copolymers, styrol maleic acid copolymers, hydroxypropyl methyl cellulose phthalate, acrylic resins, cellulose acetate trimellitate, hydroxypropyl methylcellulose trimellitate, shellac, hydroxyethyl ethyl cellulose phthalate, carboxymethylcellulose and hydroxypropyl methyl cellulose acetate succinate.

Preferred enteric coating substances include polyvinyl acetate phthalate and, particularly, methacrylic acid copolymers.

The skilled person will understand that the enteric coating can comprise other commonly used materials, such as talc (as plasticiser), dibutyl sebacate (as plasticiser), and a blend of HMPC and PEG as a sub-coating agent.

The composition may comprise one or more cores comprising budesonide that are encapsulated by a combination of delayed and extended release excipients, in order to substantially prevent release of the contents of said composition until the distal region of the small intestine (e.g., the ileum, such as the distal ileum) is reached. Such compositions are referred to hereinafter as "core-shell compositions of the invention", which encompasses "beads" and "encapsulated cores".

The cores comprising budesonide may be loaded into a capsule. When using a capsule, the delayed release coating (e.g., the enteric coating) may be on the capsule and not directly on the cores.

When the enteric coating is on the capsule, such as a size 1 capsule, the enteric coating may be present in an amount of from about 34 to about 46 mg per capsule, such as about 34 to about 42 mg per capsule, for example about 36 to about 40 mg per capsule.

In order to ensure in such core-shell compositions of the invention that the bulk of the budesonide is substantially released to the distal region of the small intestine (e.g., the ileum, such as the distal ileum), they may be (or may further be) individually coated with an extended release polymer coating.

For the avoidance of doubt, the extended release polymer coating is different to the delayed release coating.

Such an extended release coating may ensure that the bulk of the budesonide is released extensively throughout the ileum, and in combination with a delayed release coating (e.g. the enteric coating) may further ensure that such release is obtained substantially, and/or primarily, to the ileum region of the small intestine.

By "substantially released to the ileum region", we include that at least about 51%, such as at least about 60%, including at least about 70% or at least about 75%, such as at least about 80%, including at least about 90% of the initial content of active ingredient within a composition is released to that region.

The skilled person will understand that any pharmaceutical composition should be taken according to the prescription guidance and that if taken in such a manner that differs from the prescribing information then the desired effect may not be achieved. In the context of the present invention, it is preferable that the composition is taken orally at least one hour before a meal, and more preferably that the composition is taken orally in the morning at least one hour before the first meal of the day.

The extended release coating may comprise a pharmaceutically-acceptable polymeric blend comprising a water-insoluble polymer and a pore-forming polymer that is applied directly on the budesonide-containing cores. The resultant cores, or a composition comprising a plurality of cores, may then be encapsulated within a delayed release coating, which combination of excipients substantially prevents release of the contents of said composition until the ileum region of the small intestine is reached.

As used herein, the term "water-insoluble polymer" refers to a polymer having a solubility in aqueous solvents, such as water at about 25° C. of less than about 0.1 mgmL$^{-1}$. The presence of the water-insoluble polymer allows for the rate of release of budesonide in the composition to be controlled.

The water-insoluble polymer may be an alkyl cellulose or a derivative thereof, for example the water-insoluble polymer may be ethylcellulose (or a derivative thereof).

By the term, "alkyl cellulose or derivative thereof" we refer to chemical compounds derived from cellulose wherein a proton on at least some of the cellulose hydroxy groups has been replaced with an alkyl group.

As used herein, the term "pore-forming polymer" refers to polymers which have a higher water solubility than the water-insoluble polymer and are, therefore, capable of dissolving first leaving pores in the coating, thus allowing a certain amount of water to penetrate towards the core.

Therefore, the pore-forming polymer may be defined as being "water-soluble". That is to say, the pore-forming polymer has a solubility in aqueous solvents, such as water at 25° C. of at least about 10 mgmL$^{-1}$.

The pore-forming polymer may have a nominal viscosity of from about 1 to about 300 mPa*s, for example from about 1 to about 50 mPa*s, such as from about 1 to about 30 mPa*s, for example from about 1 to about 20 mPa*s, such as from about 2 to about 9 mPa*s, for example from about 2 to about 7 mPa*s, preferably from about 2 to about 6 mPa*s. The nominal viscosity of the pore-forming polymer may be measured at 20° C. as a 2 wt. % solution of the polymer in water by the standard Ph.Eur. 2.2.9 capillary viscometer method.

Furthermore, the pore-forming polymer may have a gelling temperature of from about 35 to about 65° C., for example from about 55 to about 65° C., such as from about 58 to about 64° C.

The pore-forming polymer may comprise a polymer selected from the list consisting of polyethylene glycol (PEG), hydroxypropylmethyl cellulose (HPMC) and hydroxypropyl cellulose (HPC). Preferably, the pore-forming polymer is hydroxypropylmethyl cellulose.

The degree of substitution of the HPMC with methoxy groups may be from about 15 to about 35 wt. %, for example from about 25 to about 35 wt. %, or about 27 to about 31 wt. %, such as from about 27 to about 30 wt. %. Furthermore, the degree of substitution of the HPMC with hydroxypropyl groups may be from about 4 to about 32 wt. %, for example from about 4 to about 20 wt. %, or from about 5 to about 15 wt. %, such as from about 7 to about 12 wt. %.

By the term "degree of substitution of the HPMC" this refers to the average level of substitution of the hydroxy groups on the cellulose chain and is expressed herein in percentage terms, i.e. the percentage of hydroxy groups that have been substituted with the moiety in question.

The water-insoluble polymer may present in an amount of from about 45 wt. % to about 90 wt. % of the total extended release coating and the pore-forming polymer may present in an amount of from about 35 wt. % to about 5 wt. % of the total extended release coating. Such as, the water-insoluble polymer may present in an amount of from about 45 wt. % to about 65 wt. % of the total extended release coating and the pore-forming polymer may present in an amount of from about 35 wt. % to about 15 wt. % of the total extended release coating. For example, the water-insoluble polymer may present in an amount of from about 47 wt. % to about 56 wt. % of the total extended release coating and the pore-forming polymer may present in an amount of from about 32 wt. % to about 22 wt. % of the total extended release coating.

The pharmaceutically-acceptable polymeric blend of the extended release coating may comprise a fatty acid in an amount of from about 2 wt. % to about 8 wt. %, such as from about 3 wt. % to about 7 wt. % of the total extended release coating.

The fatty acid may be an unsaturated fatty acid, for example a $C_4$ to $C_{28}$ unsaturated fatty acid, such as a $C_{13}$ to $C_{22}$ unsaturated fatty acid. For example, the unsaturated fatty acid may be selected from the group consisting of myristoleic acid, palmitoleic acid, sapienic acid, oleic acid, elaidic acid, vaccenic acid, and erucic acid. Preferably, the unsaturated fatty acid is oleic acid.

The pharmaceutically-acceptable polymeric blend of the extended release coating may comprise a medium-chain triglyceride in an amount of from about 3 wt. % to about 12 wt. %, such as from about 5 wt. % to about 12 wt. %, for example from about 5 to 8 about wt. % of the total extended release coating.

By the term "medium-chain triglyceride" this refers to triglycerides having an aliphatic tail of from 6 to 12 carbons. For example, the medium-chain triglyceride may be selected from the list consisting of caproic acid, caprylic acid, capric acid and lauric acid.

The pharmaceutically-acceptable polymeric blend of the extended release coating may comprise a further water-soluble polymer in an amount of from about 1 wt. % to about 5 wt. %, such as from about 2 wt. % to about 3 wt. % of the total extended release coating. For the avoidance of doubt, the further water-soluble polymer is different to the pore-forming polymer. Preferably, the further water-soluble polymer is poly(ethylene glycol) having a molecular weight in the range of from about 200 to about 1000 g/mol.

The polymeric blend that coats the one or more cores may be coalescable. By the term "coalescable" when referring to the extended release polymeric blend, this refers to the polymers of the extended release blend being capable of blending to form a single polymeric phase coating.

Therefore, the extended release polymeric blend that coats the one or more cores may comprise one or more coalescable polymers. The one or more coalescable polymers may comprise the water-insoluble polymer.

The extended release polymer blend may be present in an amount of from about 5 to about 18 wt. % of the total bead/core, for example from about 6 to about 16 wt. % of the total bead/core, for example from about 6 to about 13 wt. %, such as about 6 to about 12 wt. % of the total bead/core.

It has been found that in the polymer blend of the extended release coating that the pore-forming polymer dissolves first, before the water-insoluble polymer, in an aqueous solution leaving pores in the coating, thus allowing a certain amount of water to penetrate towards the core in a controlled fashion.

The cores may have an average size in the range of from about 0.5 to about 3 mm, for example about 0.5 to about 2 mm, such as about 0.8 to about 1.5 mm.

The core-shell compositions of the invention may be prepared by a process which comprises:
  (a) providing one or more cores comprising budesonide;
  (b) which one or more cores are individually coated with by an extended release pharmaceutically-acceptable polymeric blend comprising a water-insoluble polymer in an amount of from about 45 wt. % to about 90 wt. % and a pore-forming polymer in an amount of from about 35 wt. % to about 5 wt. %; and wherein the composition is encapsulated within a delayed release coating, such as to substantially prevent release of the contents of said composition until the ileum region of the small intestine is reached.

The core-shell compositions of the above-described process may comprise any of the features as outlined above with respect to the method of the invention.

The cores may be prepared by providing inert (e.g., sugar) beads and coating them with an aqueous budesonide suspension. The inert beads may have a size of from about 1 to about 2 mm, such as about 1 to about 1.5 mm, for example about 1 to about 1.2 mm.

As referred to herein, the term "inert bead" includes a single pharmaceutically inert bead that provides the starting material for the preparation of the core-shell compositions of the invention.

The inert bead is preferably a commercially-available sugar sphere (often termed non-pareil). Sugar spheres predominantly comprise sucrose with smaller amounts of other materials added, such as starch. Suppliers of sugar spheres include Paulaur Corporation (USA), Chr. Hansen (Denmark), NP Pharm (France), Emilio Castelli (Italy) and JRS Pharma (Germany).

Prior to adding the extended release polymeric blend, the cores may be coated with a seal coating comprising a stabilised and a water-soluble polymer. The stabiliser may be an acid, wherein the acid is preferably citric acid and the soluble polymer is the same polymer as that used as the pore-forming polymer in the polymeric blend. Alternative stabilisers for inclusion in the seal coating include poly(vinyl pyrrolidone) (PVP) with the soluble polymer being the same polymer as that used as the pore-forming polymer in the polymeric blend.

The extended release polymeric blend may be applied to the cores as an aqueous polymer suspension and spraying the suspension onto the cores. The aqueous polymeric blend may be sprayed onto the cores at a temperature of from about 30° C. to about 65° C., such as from about 30° C. to about 50° C.

Spraying at a temperature towards the upper end of this region, such as about 50 to about 65° C. may avoid the requirement of a separate curing/coalescing step as outlined below.

The core-shell compositions of the invention may be obtainable by the process of coating the cores in a fluidized bed apparatus as defined above. That is to say, the coating with the extended release polymer blend may be carried out in a fluidized bed apparatus. Suitably fluidized bed apparatus are readily available from suppliers such as Glatt GmbH.

Following coating with the polymeric blend, the polymers may be coalesced, wherein the coalescing may be carried out by curing.

Curing may be carried out at a temperature of from about 55° C. to about 75° C., such as from about 60° C. to about 70° C., for example from about 63° C. to about 66° C. Furthermore, curing may be carried out for from about 1 hour to about 10 hours, for example from about 1 to about 5 hours, such as from about 2 to about 4 hours.

It was found that the extended release polymer coating blend allowed for the budesonide cores to be prepared in an economical fashion using a fluidized bed apparatus while arrive at compositions with the desired release profiles.

Therefore, in addition, the curing of the core-shell compositions of the invention may be carried out in a fluidized bed apparatus.

According to a further aspect of the invention there is provided a composition that gives rise to the desired in vitro release profile in all aspects as described herein, which comprises a plurality of beads comprising:

(a) budesonide-containing cores, in which cores budesonide is presented as a coating upon one of more inert core substrates (e.g., sugar beads) as described herein;

(b) an extended release coating presented upon said budesonide-containing cores, in an amount of between about 6 to about 12 wt. % of the total bead weight and which coating comprises a coalesced blend of at least two polymers (i) and (ii):

(i) any one of the water-insoluble polymers described herein (e.g., ethylcellulose), and (ii) any one of the pore-forming polymers that described herein (e.g., hydroxypropylmethyl cellulose, with a degree of substitution with methoxy groups from about 27 to about 30 wt. % and/or a degree of substitution of with hydroxypropyl groups from about 7 to about 12 wt. %), which blend of polymers (i) and (ii) is in any one of the proportions mentioned hereinbefore (e.g., the water-insoluble polymer (i) in an amount of from about 47 wt. % to about 56 wt. %, and the pore-forming polymer (ii) in an amount of from about 32 wt. % to about 22 wt. %, each of the total extended release coating), which beads are then loaded into a capsule that is coated with a delayed release coating (e.g., any one of the enteric coatings described herein, such as polyvinyl acetate phthalate or, particularly, methacrylic acid copolymers).

The above composition may comprise one of more of the other preferred features disclosed in respect of core-shell compositions and/or beads as described herein, such as:

any one of the fatty acids described herein, e.g., in an amount of from about 3 wt. % to about 7 wt. % of the total extended release coating;

any one of the medium-chain triglycerides described herein, e.g., in an amount of from about 5 to 8 about wt. % of the total extended release coating;

one or more further water-soluble polymers, such as poly(ethylene glycol) having a molecular weight in the range of from about 200 to about 1000 g/mol, in an amount of from about 2 wt. % to about 3 wt. % of the total extended release coating.

The above composition may also comprise a seal coating solution of an appropriate acid (e.g., a citric acid), located between the budesonide-containing cores and the extended release coating.

Each capsule may comprise about 4 mg of budesonide and when administered to the patient a total of about 16 mg may be delivered orally by way of the patient taking four capsules.

The coalesced blend of at least two polymers (i) and (ii), which is obtained prior to loading the coated beads into the capsule is preferably obtained by coating the budesonide-containing cores in a fluidized bed apparatus by way of the application of an aqueous dispersion comprising polymers (i) and (ii) as defined above at a temperature that is between about 30° C. to about 65° C., such as from about 30° C. to about 50° C., particularly about 50 to about 65° C. and then, if necessary, further coalescing the so coated polymeric extended release coating within the fluidized bed apparatus by application of a temperature of from about 60° C. to about 70° C. (e.g., from about 63° C. to about 66° C.) for an appropriate time (e.g., from about 2 to about 4 hours) in order to cure it.

Alternatively, a polymeric blend may be sprayed as an organic solution. In this embodiment it is not necessary to carry out a further curing step.

As alluded to above, the core(s) that is/are coated by the aforementioned extended release polymeric blend may be loaded into a capsule, and the capsule may be coated with said delayed release coating.

However they are made, compositions that may be employed in the methods of the invention may be useful in the treatment of IgAN because they meet the in vitro release characteristics defined above.

Accordingly, there is further provided:
- any one of the compositions as defined herein for use in the treatment of IgAN;
- the use of any one of the compositions as defined herein for manufacture of a medicament for the treatment of IgAN; and
- a method of treatment of IgAN, which method comprises the administration of any one of the compositions as defined herein to a patient in need of such treatment.

According to a further aspect of the invention, there is provided a core-shell composition of the invention, as described hereinbefore.

As an alternative to the core-shell composition, the composition may comprise a tablet comprising budesonide, which tablet is encapsulated within one or more excipients that substantially prevent release of the contents of said composition until the ileum region of the small intestine is reached. Such compositions are referred to hereinafter as "encapsulated tablet compositions of the invention"

The one or more excipients that encapsulate the tablet to substantially prevent release of the contents of said composition until the ileum region of the small intestine is reached may be an enteric coating as defined above.

The enteric coating in the tablet composition may be present in an amount of from about 5 wt. % to about 15 wt. %, such as from about 7 wt. % to about 13 wt. %, for example from about 8 wt. % to about 12. wt. % of the total tablet.

Tablet compositions of the invention may comprise a wet granulate of budesonide along with a filler. Optionally, the filler comprises dicalcium phosphate, microcrystalline cellulose, mannitol, or a mixture thereof.

The filler may be present in an amount of from about 50 wt. % to about 80 wt. %, such as about 60 wt. % to about 75 wt. %, for example about 65 wt. % to about 75 wt. % of the total tablet.

Tablet compositions of the invention may be a compressed tablet that further comprises a lubricant, optionally wherein the lubricant is magnesium stearate, aluminium stearate, calcium stearate, sodium stearate, zinc stearate, stearic acid, decanoic acid, dodecanoic acid, sodium stearyl fumarate or a mixture thereof.

The lubricant may be present in an amount of from about 0.1 wt. % to about 2 wt. %, such as from about 0.1 wt. % to about 1 wt. % of the total tablet.

Tablet compositions of the invention may further comprise a disintegrant, optionally wherein the disintegrant is selected from crospovidone, croscarmellose sodium or sodium starch glycolate. Alternatively, the tablet may not comprise a disintegrant.

The disintegrant may be present in an amount of from about 0.5 wt. % to about 5 wt. %, such as from about 0.5 wt. % to about 4 wt. %, for example from about 0.8 wt. % to about 3.5 wt. % of the total tablet.

Tablet compositions of the invention may further comprise a binder, optionally wherein the binder is selected from hydroxyethyl cellulose, hydroxypropyl cellulose, copovidone, or mixtures thereof.

The binder may be present in an amount of from about 5 wt. % to about 10 wt. %, such as from about 6 wt. % to about 9 wt. %, for example from about 7 wt. % to about 9 wt. % of the total tablet.

Such tablet compositions of the invention may be gelling matrix tablets that further comprise a gelling matrix material, such as a low molecular weight HPMC (e.g., Hypromellose).

The gelling matrix material may be present in an amount of about 10 to about 25 wt. %, such as about 10 to about 20 wt. %, for example about 15 to about 20 wt. % of the total tablet.

The gelling matrix material may be diluted with a water-soluble filler, which water-soluble filler may comprise lactose, dextrose, mannitol, and combinations thereof.

The tablet may comprise an enteric coating comprising any of the materials as outlined above. The enteric coating may be present in an amount of from about 5 to about 15 wt. % of the total tablet, such as about 8 to about 12 wt. % of the total tablet.

Each tablet may comprise from about 2 to about 20 mg of budesonide, such as from about 4 to about 16 mg of budesonide. Preferably, each tablet comprises about 4 mg of budesonide.

Compositions when characterised by the method of the invention (in all aspects) are useful because they are more effective treatments of IgAN. Such compositions, pharmaceutical formulations, uses and methods described herein may also have the advantage that, in the treatment of IgAN, they may be more convenient for the physician and/or patient than, be more efficacious than, be less toxic than, have a broader range of activity than, be more potent than, produce fewer side effects than, have a lower inter-patient variability, or may have other useful pharmacological properties over, similar formulations or methods (treatments) known in the prior art, whether for use in the treatment of IgAN or otherwise.

Wherever the word 'about' is employed herein in the context of amounts, for example absolute amounts, such as weights, volumes, sizes, diameters, etc., or relative amounts (e.g. percentages) of individual constituents in a composition or a component of a composition (including concentrations and ratios), timeframes, and parameters such as temperatures, etc., it will be appreciated that such variables are approximate and as such may vary by ±10%, for example ±5% and preferably ±2% (e.g. ±1%) from the actual numbers specified herein. This is the case even if such numbers are presented as percentages in the first place (for example 'about 10%' may mean ±10% about the number 10, which is anything between 9% and 11%).

EXAMPLES

Example 1: Manufacturing of Core-Shell Composition

Opadry OY-7240 as referred to below is a dry powder polymer blend having the following components:

| % w/w | Ingredients/Compendial Reference | Grade/Dye Strength | E Number | CFR Reference |
|---|---|---|---|---|
| 90.910 | HPMC 2910/Hypromellose (USP, Ph. Eur., JP, FCC) | 5 mPas | E464 | 172.874 |
| 9.090 | Macrogol/PEG (NF, FCC, Ph. Eur., JECFA, JP) | MW 400 | E1521 | 172.820 |

Surelease is a polymer dispersion having the following components:

| Test | Minimum | maximum |
|---|---|---|
| Oleic Acid, % | 1.6 | 2.2 |
| Ethylcellulose, % | 17.0 | 20.0 |
| Oleic Acid to Ethylcellulose Ratio | 0.00 | 0.14 |
| Medium Chain Triglycerides, % | 0.80 | 4.00 |
| MCT to Ethylcellulose Ratio | 0.00 | 0.24 |
| Glycerin, % | 0.0 | 0.6 |
| Solids, % | 23.0 | 26.0 |
| Ph | 9.5 | 11.5 |
| Viscosity Brookfield, cps | 400.00 | 1500.00 |

For the avoidance of doubt, the minimum and maximum values in the table above refer to the minimum and maximum amounts of these components in different batches of Surelease.

A flow diagram detailing the preparation of budesonide beads according to the core-shell composition of the invention is provided in FIG. 1 and explained in further detail below.

A budesonide coating suspension was prepared by dissolving the Opadry OY-7240 Clear (2.29 kg) in purified water (26.5 kg) and then adding micronized budesonide (0.640 kg) to the solution while mixing continuously.

Sugar spheres (40.3 kg) having a mesh size of 16 to 18 were loaded into a pre-heated product bowl of a fluidized bed. When the product temperature reached the target of 45° C. the active coating suspension was sprayed onto the sugar spheres/inert core. The operation was monitored and controlled by a process computer. After the completion of spraying the required amount of active coating suspension, the active coated beads were dried and cooled.

A seal coating solution was prepared by dissolving citric acid monohydrate (0.093 kg) and Opadry OY-7240 Clear (2.26 kg) in purified water (21.8 kg) while mixing continuously.

The seal coating solution was applied onto the pre-warmed active coated beads. The operation was monitored and controlled by a process computer. The coating was stopped when the required amount of solution has been sprayed, and the seal coated beads were dried and cooled.

The fluid bed was emptied, and the beads were screened using 1.4 mm (14 Mesh) and 0.5 mm (35 Mesh) screens to remove any oversize and undersize particles. The beads were weighed, and the yield of the accepted fraction was calculated.

An extended release coating solution was prepared by adding Opadry OY-7240 (1.37 kg) to purified water (16.3 kg) while mixing continuously. An ethylcellulose suspension dispersion Type B (Surelease, 12.8 kg) was added to the Opadry solution during continued mixing.

The accepted fraction of the seal coated beads was loaded into the pre-heated product bowl of the fluidized bed with Wurster columns. When the product temperature reached the target temperature the extended release polymer coating suspension was applied onto the beads. The operation was monitored and controlled by a process computer. The amount sprayed was calculated from the amount of the accepted fraction of seal coated beads from the previous step.

The resulting polymer blend of the extended release coating on the beads comprised about 27.3 wt. % HPMC of the total blend and about 51.8 wt. % ethylcellulose of the total blend. The ethylcellulose is a water-insoluble polymer as defined above and the HPMC acts as the pore forming polymer.

After completion of the spraying, the beads were dried and cooled. The fluid bed was emptied, and the beads were screened using 1.4 mm (14 Mesh) and 0.5 mm (35 Mesh) screens to remove any oversize and undersize particles. The beads were weighed, and the yield of the accepted fraction was calculated.

The accepted fraction of the polymer coated beads was loaded into a pre-heated drying bowl of the fluid bed equipment. The beads were cured at target temperature of 65° C. for 3 hours. The operation was monitored and controlled by a process computer. The fluid bed was emptied, and a sample of the cured beads was taken for assay and dissolution testing. The cured beads were weighed, and the yield was calculated. The beads were filled into a stainless steel in-bin hopper.

The cured beads were then filled into capsules of size 1 using an automated encapsulator and the capsules were then coated with an enteric coating. The enteric coating of the capsules used was a blend of methacrylic acid and methyl methacrylate copolymers 1:1, and 1:2. The amount of enteric coating applied to each capsule was in the range of from about 34 to about 42 mg per capsule. The total amount of budesonide in each capsule was about 4 mg.

Example 2: General Process for Standard In Vitro Dissolution Test According to USP<711>/pH.Eur. 2.9.3 in the Presence of Surfactant in the Buffer Stage and at a Paddle Rotation Speed of 100 rpm The in vitro dissolution of the encapsulated budesonide core-shell beads of Example 1 were analysed as described in Ph.Eur. 2.9.3 Dissolution test for solid dosage forms (using Apparatus 2) and as described in USP <711> Dissolution (using Apparatus 2). The measurement was carried out as described below.

| Dissolution Apparatus Setup | |
|---|---|
| Apparatus: | USP <711>/Ph. Eur. 2.9.3 Apparatus 2 |
| Vessel Size/Type: | 1000 mL/clear glass, round-bottom |
| Rotation Speed: | 100 rpm |

-continued

| Dissolution Apparatus Setup | |
|---|---|
| Media Volume: | 900 mL - Acid Resistance |
| | 900 mL - Buffer Dissolution |
| Test Temperature: | 37.0 ± 0.5° C. |
| Pull Volume: | 15 mL |
| Replacement: | No |
| Volume Discard: | 5 mL |
| Sampling Time Point: | Acid Resistance Stage: |
| | 2 hours |
| | Buffer Stage: |
| | Specified time points 0.5 and 2 hours |

Budesonide release was measured using Ultra Performance Liquid Chromatography (UPLC).

Reagents and Standards

Standards and Reference Materials:

Budesonide, Ph. Eur. CSR or suitable secondary standard.

Other Reagents:

Tween 80, (Polyoxyethylene (20), Polysorbate (80), Fisher Scientific or equivalent.

Dissolution Media and Diluents

Acid Resistance Media 0.1 N HCl Solution. To prepare 6 L of acid resistance media, 50 mL of concentrated HCl was combined with 6000 mL of water and the resulting solution was mixed well.

0.2 M Sodium Phosphate Tribasic Buffer Solution

To prepare 1 L of 0.2 M sodium phosphate tribasic buffer solution, about 76.02 g of sodium phosphate tribasic was added and dissolved into 1000 mL of water, followed by mixing.

Buffer Dissolution Media: 50 mM Sodium Phosphate Buffer, pH 6.8, with Tween 80.

To make 6 L of buffer dissolution media, 4500 mL Acid Resistance Media was combined with 1500 mL 0.2 M Sodium Phosphate Tribasic Buffer Solution and 3 g of Tween 80, followed by mixing. The pH was checked and, if necessary, adjusted pH to 6.8±0.05 using either Hydrochloric Acid or Sodium Hydroxide.

Analytical Procedure

Acid Resistance Procedure

Note: Care should be taken not to scrape or damage the capsules when placing into sinkers.

900 mL of preheated degassed Acid Resistance media was placed into each of 6 dissolution vessels. The media was held at a temperature of 37° C.±0.5° C.

The apparatus was operated as per the USP<711>/Pharmacopeia test no. 2.9.3 Rotating Paddle Apparatus method at 100 rpm.

6 capsules were then placed each into separate coil sinkers and then into individual vessels.

At 2 hours, a 15-mL aliquot of the Acid Resistance Solution was withdrawn using a syringe.

The test solution was filtered with a Whatman GF/F with GMF filter, with the first 5 mL being discarded and the remaining solution being collected in a test tube.

The two steps below were completed after the Buffer Stage Dissolution has been initiated.

5.0 mL of the filtered Acid Resistance Sample solution was pipetted into a 10 mL volumetric flask and diluted to volume with Acetonitrile.

The solution was mixed well and an aliquot was transferred to a HPPLC vial and analysed.

The budesonide release in the acid resistance stage was assessed based on the acceptance criteria in USP<711>/Ph.Eur. 2.9.3.

Buffer Stage Dissolution Procedure

After Acid Resistance samples were pulled, forceps were used to transfer each coil sinker containing a budesonide capsule to a different set of dissolution vessels containing 900 mL of buffer dissolution media at temperature 37° C.±0.5° C.

The apparatus was operated as per the USP<711>/Pharmacopeia test no. 2.9.3 Rotating Paddle Apparatus method at 100 rpm.

Specified timepoint sampling: At 0.5 and 2 hours, a 15-mL aliquot of the dissolution solution was withdrawn using a syringe. The fluid withdrawn was not replaced.

The test solution was filtered with a Whatman GF/F with GMF filter, with the first 5 mL being discarded and the remaining solution being collected in a test tube.

5.0 mL of the filtered Dissolution Sample Solution was pipetted into a 10 mL volumetric flask and diluted to volume with acetonitrile.

The solution was mixed well and an aliquot was transferred to a HPLC vial.

Budesonide release in the buffer stage was assessed based on the acceptance criteria in USP<711>/Ph.Eur. 2.9.3.

Example 3: Dissolution Profile Analysis According to In Vitro USP<711>/Pharmacopeia Test No. 2.9.3 in the Presence of Surfactant in the Buffer Stage and at a Paddle Rotation Speed of 100 rpm The capsules prepared in Example 1 ("budesonide capsules" or "nefecon budesonide") were tested under the dissolution conditions outlined in Example 2.

Figure 2:
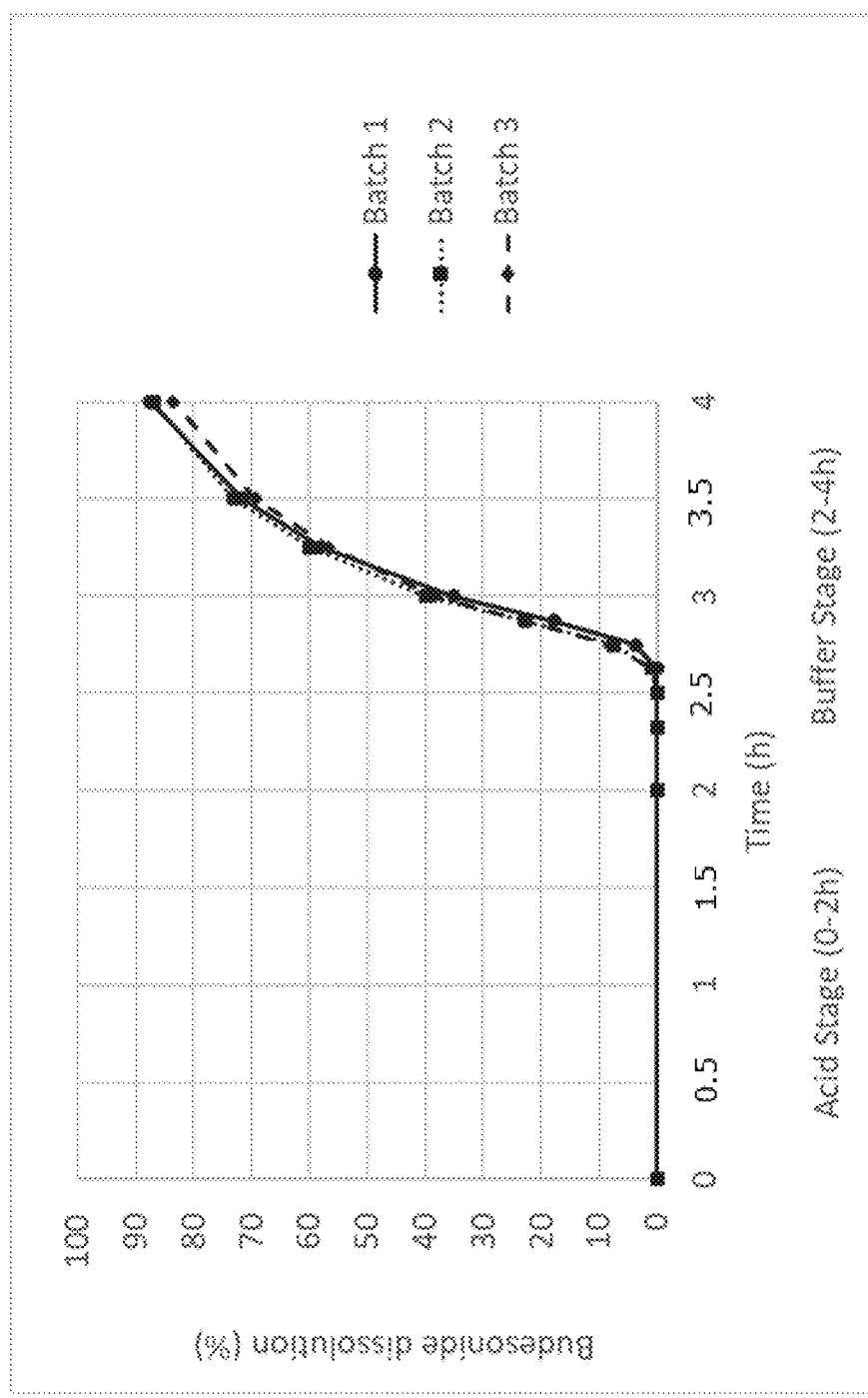
FIG. 2 shows the in vitro dissolution profiles of budesonide modified release capsules in the presence of added surfactant in the pH 6.8 buffer medium at a paddle rotation speed of 100 rpm; data shown for different capsule batches prepared according to the invention.
Figure 3:
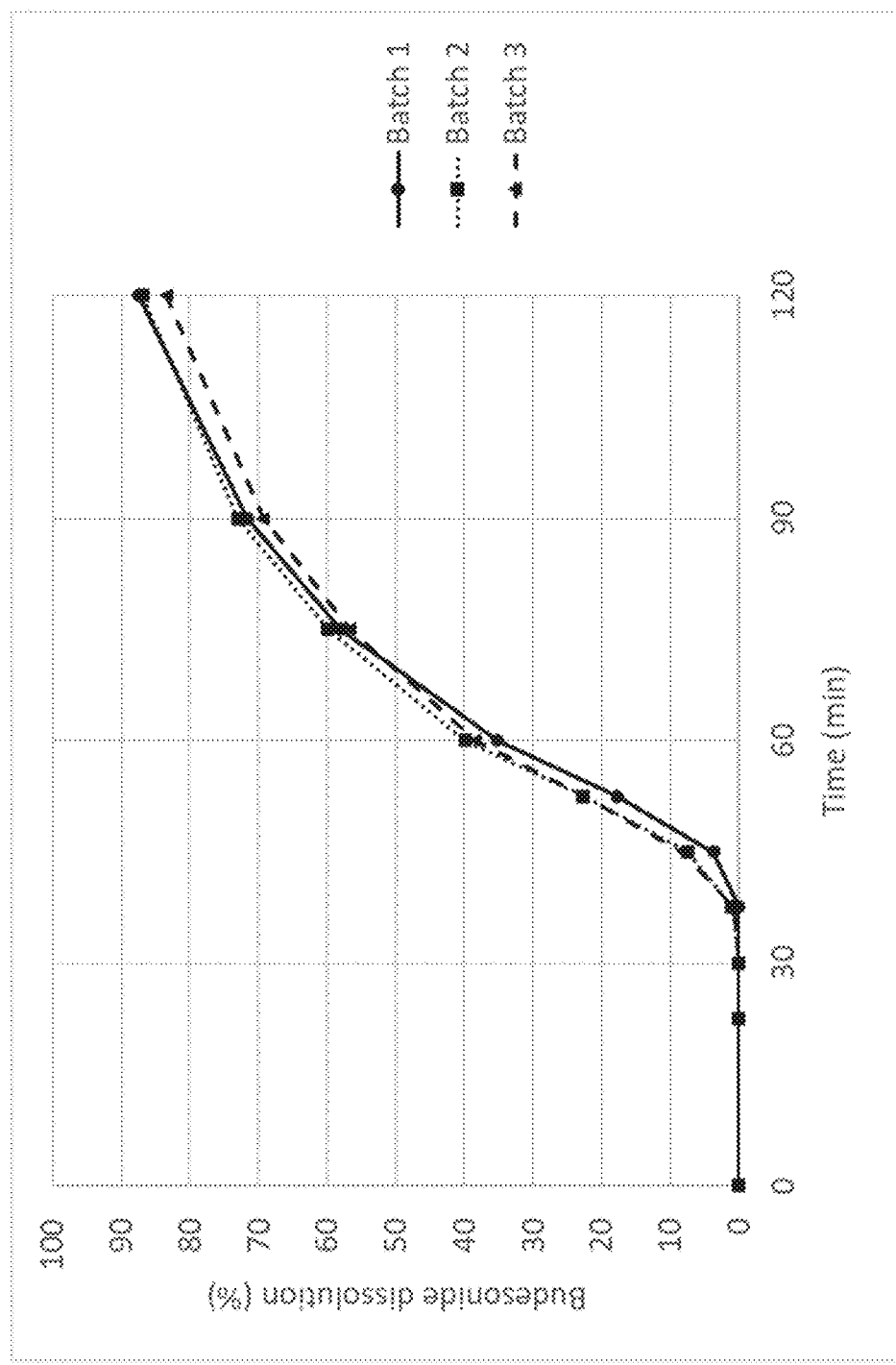
FIG. 3 is a repeat of the in vitro dissolution profile shown in FIG. 2 focusing only on the dissolution at pH 6.8.

The overall dissolution profile for three separate batches can be seen in FIG. 2, with the time from 0 to 2 hours being at acid pH (pH 1.2) and the time from 2 to 4 hours being at buffered pH 6.8. FIG. 3 is a repeat of FIG. 2, showing only the dissolution at buffered pH 6.8 with time 0 to 120 minutes in FIG. 3 corresponding to time 2 to 4 hours in FIG. 2. Twelve capsules were tested per batch.

The quantitative results of the dissolution of budesonide in the various media at time points 2 hours at pH 1.2, 0.5 hours at pH 6.8 and 2 hours at pH 6.8 are provided in Table 1 below.

TABLE 1

| | | | Batch 1 | Batch 2 | Batch 3 |
|---|---|---|---|---|---|
| Dissolution (%) | pH 1.2, 2.0 h | Average | 0 | 0 | 0 |
| | | SD | 0 | 0 | 0 |
| | pH 6.8, 0.5 h | Average | 0 | 0 | 0 |
| | | SD | 0 | 0 | 0 |
| | pH 6.8, 2.0 h | Average | 88 | 87 | 84 |
| | | SD | 2.2 | 2.6 | 3.5 |

*SD = standard deviation

The budesonide release in the acid resistance stage and the buffer stage was assessed based on the acceptance criteria in <711>/Ph.Eur. 2.9.3.

Example 4: General Process for Standard In Vitro Dissolution Test According to USP<711>/pH.Eur. 2.9.3 in the Absence of Surfactant in the Buffer Stage and at a Paddle Rotation Speed of 50 rpm The in vitro dissolution of the encapsulated budesonide core-shell beads of Example 1 were analysed as described in Ph.Eur. 2.9.3 Dissolution test for solid dosage forms (using Apparatus 2) and as described in USP <711> Dissolution (using Apparatus 2). The measurement was carried out as described below.

| Dissolution Apparatus Setup | |
|---|---|
| Apparatus: | USP <711>/Ph. Eur. 2.9.3 Apparatus 2 |
| Vessel Size/Type: | 1000 mL/clear glass, round-bottom |
| Rotation Speed: | 50 rpm |
| Media Volume: | 900 mL - Acid Resistance |
| | 900 mL - Buffer Dissolution |
| Test Temperature: | 37.0 ± 0.5° C. |
| Pull Volume: | 15 mL |
| Replacement: | No |
| Volume Discard: | 5 mL |
| Sampling Time Point: | Acid Resistance Stage: |
| | 2 hours |
| | Buffer Stage: |
| | Specified time points 0.625, 1.25 and 2.5 hours. |

Budesonide release was measured using Ultra Performance Liquid Chromatography (UPLC).

Reagents and Standards

Standards and Reference Materials:

Budesonide, Ph. Eur. CSR or suitable secondary standard.

Dissolution Media and Diluents

Acid Resistance Media 0.1 N HCl Solution. To prepare 6 L of acid resistance media, 50 mL of concentrated HCl was combined with 6000 mL of water and the resulting solution was mixed well.

0.2 M Sodium Phosphate Tribasic Buffer Solution

To prepare 1 L of 0.2 M sodium phosphate tribasic buffer solution, about 76.02 g of sodium phosphate tribasic was added and dissolved into 1000 mL of water, followed by mixing.

Buffer Dissolution Media: 50 mM Sodium Phosphate Buffer, pH 6.8, with Tween 80.

To make 6 L of buffer dissolution media, 4500 mL Acid Resistance Media was combined with 1500 mL 0.2 M Sodium Phosphate Tribasic Buffer Solution. The pH was checked and, if necessary, adjusted pH to 6.8±0.05 using either Hydrochloric Acid or Sodium Hydroxide.

Analytical Procedure

Acid Resistance Procedure

Note: Care should be taken not to scrape or damage the capsules when placing into sinkers.

900 mL of preheated degassed Acid Resistance media was placed into each of 6 dissolution vessels. The media was held at a temperature of 37° C.±0.5° C.

The apparatus was operated as per the USP<711>/Pharmacopeia test no. 2.9.3 Rotating Paddle Apparatus method at 50 rpm.

6 capsules were then placed each into separate coil sinkers and then into individual vessels.

At 2 hours, a 15-mL aliquot of the Acid Resistance Solution was withdrawn using a syringe.

The test solution was filtered with a Whatman GF/F with GMF filter, with the first 5 mL being discarded and the remaining solution being collected in a test tube.

The two steps below were completed after the Buffer Stage Dissolution has been initiated.

5.0 mL of the filtered Acid Resistance Sample solution was pipetted into a 10 mL volumetric flask and diluted to volume with Acetonitrile.

The solution was mixed well and an aliquot was transferred to a HPPLC vial and analysed.

The budesonide release in the acid resistance stage was assessed based on the acceptance criteria in USP<711>/Ph.Eur. 2.9.3.

The capsules prepared in Example 1 ("budesonide capsules" or "nefecon budesonide") were tested under the dissolution conditions outlined in this example.

Figure 4:
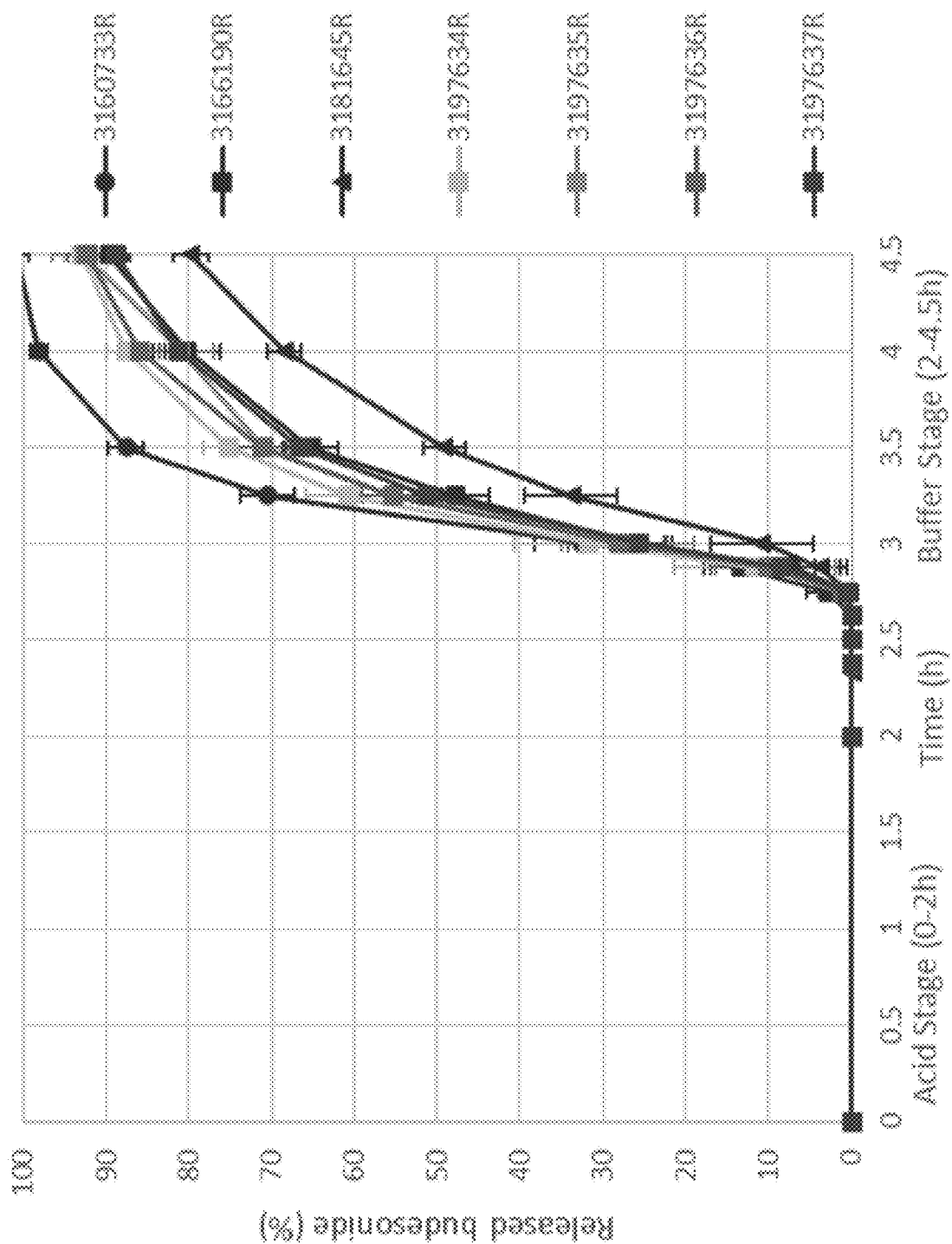
FIG. 4: relatively shows the in vitro dissolution profile for seven separate batches of budesonide modified release capsules according to the present invention with the dissolution in the buffered pH 6.8 medium being in the absence of surfactant and with a paddle rotation speed of 50 rpm.

The overall dissolution profile for seven separate batches can be seen in FIG. 4, with the time from 0 to 2 hours being at acid pH (pH 1.2) and the time from 2 to 4.5 hours being at buffered pH 6.8.

For all samples no more than 10% of the budesonide was released at time point 0.625 hours.

The quantitative results of the dissolution of budesonide at time point 1.25 hours (75 minutes) at pH 6.8 are provided in the table below.

| Capsule batch no. | Average (%) | Min (%) | Max (%) | SD |
|---|---|---|---|---|
| 3160733R | 71 | 66 | 74 | 3.2 |
| 3166190R | 48 | 43 | 53 | 4.1 |
| 3181645R | 34 | 23 | 39 | 5.6 |
| 3197634R | 61 | 57 | 71 | 5.1 |
| 3197635R | 56 | 46 | 63 | 5.7 |
| 3197636R | 55 | 49 | 60 | 3.9 |
| 3197637R | 51 | 48 | 53 | 1.7 |

*SD = standard deviation

At 1.25 h (75 minutes) from 23 to 740/of the budesonide is released.

The quantitative results of the dissolution of budesonide at time point 2.5 hours (150 minutes) at pH 6.8 are provided in the table below.

| Capsule batch no. | Average (%) | Min (%) | Max (%) | SD |
|---|---|---|---|---|
| 3160733R | 101 | 99 | 103 | 1.5 |
| 3166190R | 90 | 87 | 93 | 2.2 |
| 3181645R | 80 | 77 | 83 | 2.1 |
| 3197634R | 93 | 90 | 95 | 2.1 |
| 3197635R | 93 | 88 | 98 | 3.9 |
| 3197636R | 92 | 88 | 95 | 2.4 |
| 3197637R | 89 | 87 | 92 | 1.7 |

The lowest amount of release observed at 2.5 hours was 77%.

Example 5: Comparative Test According to USP<711>/pH.Eur. 2.9.3 in the Presence of Surfactant in the Buffer Stage and at a Paddle Rotation Speed of 100 rpm Outlined below is a variation of the in vitro test of Example 2. In this test the budesonide modified release capsules according to the present invention were analysed along with three other marketed budesonide containing formulations. The three formulations being Entocort® (Tillotts Pharma), Budenofalk® (Dr Falk Pharma GmbH) and Cortiment® (Ferring Pharmaceuticals, CH).

| Dissolution Apparatus | |
|---|---|
| Apparatus: | USP <711>/Ph. Eur. 2.9.3 |
| | Apparatus 2 |
| Vessel Size/Type: | 1000 mL/clear glass, round-bottom |
| Rotation Speed: | 100 rpm |
| Media Volume: | 900 mL - Acid Resistance |
| | 900 mL - Buffer Dissolution Profile |

| | |
|---|---|
| Test Temperature: | 37.0 ± 0.5° C. |
| Pull Volume: | 10 mL |
| Replacement: | No |
| Sampling Time Points | Acid Resistance Stage: |
| | 2 hours |
| | Buffer Stage: |
| | 15, 30, 45, 60, 90, 120, 180 minutes |
| pH check | Check the pH of the dissolution medium after preparation, and again in each vessel after each test and record the result (Buffer Dissolution Medium only). |

Figure 5:
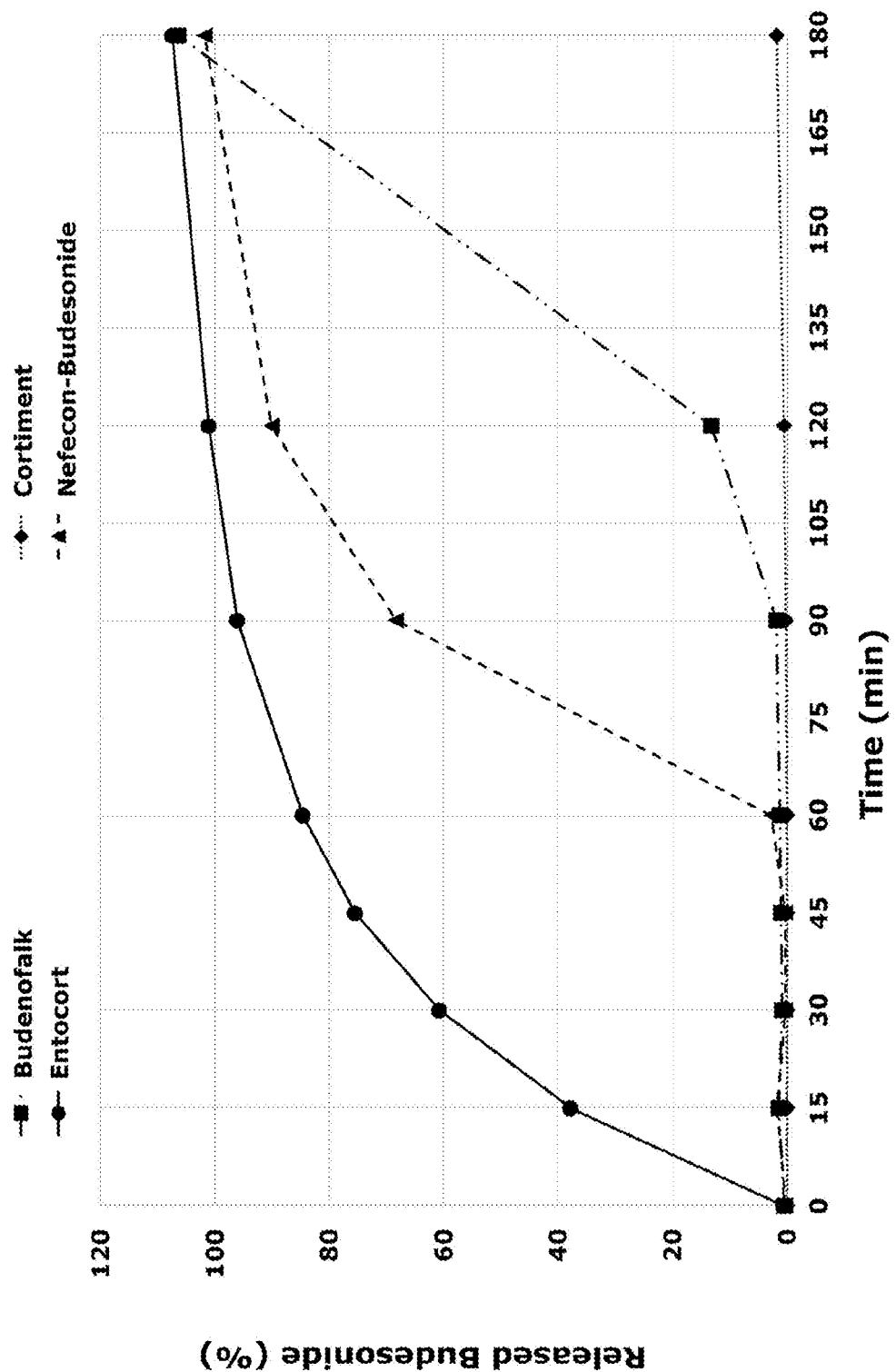
FIG. 5: shows the in vitro dissolution profiles of budesonide modified release capsules according to the present invention along with three other marketed budesonide-containing formulations in the pH 6.8 buffer medium in the presence of added surfactant and at a paddle rotation speed of 100 rpm.

Standards and Reference Materials
  Budesonide, Ph. Eur. CSR.
Other Reagents:
  Tween 80, (Polysorbate (80)), Fisher Scientific or equivalent.
Dissolution Media, Mobile Phase and Diluents
  Acid Resistance Media
  0.1N HCl Solution. For example, to prepare 10 L, combine 82 mL of concentrated HCl and 10000 mL of water, mix well.
Buffer Dissolution Media
  Sodium Phosphate pH 6.80 dissolution media was prepared by diluting one bottle (961.5 mL) of Reagecon DBC09-960 concentrate to a total volume of 25 L. See Sodium Phosphate pH 6.80 Dissolution Media 6×961.5 ml (reagecon.com) for more details.
  The pH of the buffer solution was checked after preparation.
  After Acid Resistance samples were pulled, the capsules were taken out of the solution with pincers and placed aside while the vessels were emptied, cleaned and filled with preheated buffer medium. 0.05% Tween 80 (or equivalent) was added to each dissolution vessel; for example 450 mg of Tween 80 was added to the dissolution vessels after they had been filled with 900 mL of pre-heated buffer, to arrive at a surfactant concentration of 0.05% w/v.
  After all vessels reached the target temperature, the experiment was started by adding a capsule to each vessel.
Modification of Procedure for Budenofalk
  A different procedure was used when the capsule broke during the acid stage. Most of the acid phase was carefully decanted and then the remaining acid was carefully removed with a pipette in order to remove as few pellets from the vessel as possible. The buffer stage was started by adding 900 mL of pre-heated buffer medium, followed by addition of Tween.
Sampling for Both Stages
  10 mL aspirated, 8 mL discarded (through Whatman filter (0.7 μm)), 1 mL sampled into HPLC vial.
  The variations in this test compared to Example 2 do not have an effect on the overall dissolution profiles of the products tested and the comparative dissolution profiles of the three other marketed budesonide containing formulations can be seen in FIG. 5.

Example 6: Comparative Test According to USP<711>/pH.Eur. 2.9.3 in the Absence of Surfactant in the Buffer Stage and at a Paddle Rotation Speed of 100 Rpm Outlined below is a variation of the in vitro test of Example 2 and Example 5. In this test the enteric coated capsules filled with the core-shell beads of Example 1 were analysed along with the three other marketed budesonide containing formulations in a buffer stage solution at pH 6.8 and a paddle rotation speed of 100 rpm. The three formulations being Entocort® (Tillotts Pharma), Budenofalk® (Dr Falk Pharma GmbH) and Cortiment® (Ferring Pharmaceuticals, CH).

| | |
|---|---|
| Dissolution Apparatus | USP <711>/Ph. Eur. 2.9.3 |
| Apparatus: | Apparatus 2 |
| Vessel Size/Type: | 1000 mL/clear glass, round-bottom |
| Rotation Speed: | 100 rpm |
| Media Volume: | 900 mL - Acid Resistance |
| | 900 mL - Buffer Dissolution Profile |
| Test Temperature: | 37.0 ± 0.5° C. |
| Pull Volume: | 10 mL |
| Replacement: | No |
| Sampling Time Points | Acid Resistance Stage: |
| | 2 hours |
| | Buffer Stage: |
| | 15, 30, 45, 60, 90, 120, 180 minutes |
| pH check | Check the pH of the dissolution medium after preparation, and again in each vessel after each test and record the result (Buffer Dissolution Medium only). |

Figure 6:
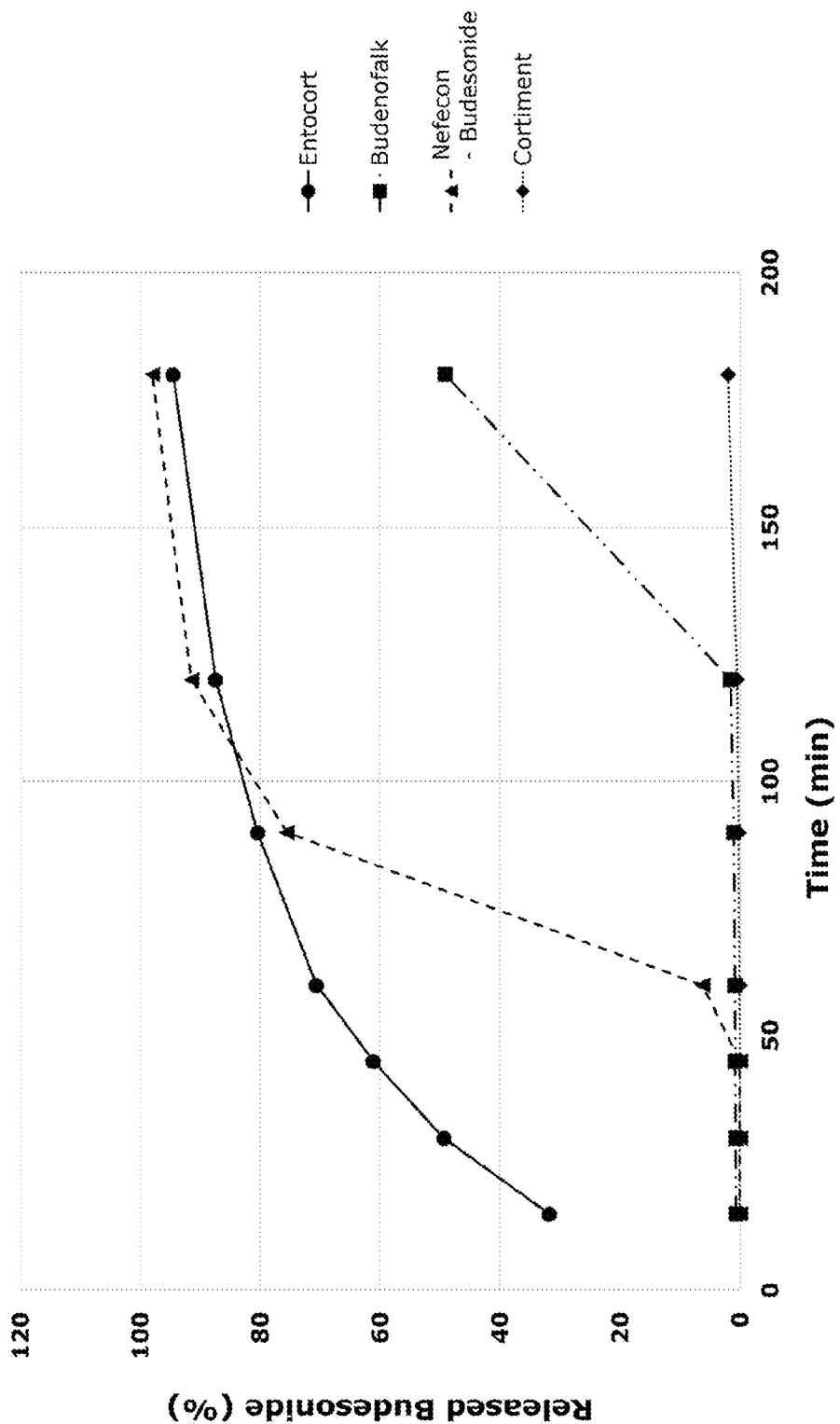
FIG. 6: shows the in vitro dissolution profiles of budesonide modified release capsules according to the present invention and three other marketed budesonide-containing formulations in the pH 6.8 buffer medium in the absence of added surfactant and at a paddle rotation speed of 100 rpm.

Standards and Reference Materials
  Budesonide, Ph. Eur. CSR.
Dissolution Media, Mobile Phase and Diluents
  Acid Resistance Media
  N HCl Solution. For example, to prepare 10 L, combine 82 mL of concentrated HCl and 10000 mL of water, mix well.
Buffer Dissolution Media
  Sodium Phosphate pH 6.80 dissolution media was prepared by diluting one bottle (961.5 mL) of Reagecon DBC09-960 concentrate to a total volume of 25 L.
  See Sodium Phosphate pH 6.80 Dissolution Media 6×961.5 ml (reagecon.com) for more details.
  The pH of the buffer solution was checked after preparation.
  After Acid Resistance samples were pulled, the capsules were taken out of the solution with pincers and placed aside while the vessels were emptied, cleaned and filled with 900 mL preheated buffer medium.
  After all vessels reached the target temperature, the experiment was started by adding a capsule to each vessel.
Modification of Procedure for Budenofalk
  A different procedure was used when the capsule broke during the acid stage. Most of the acid phase was carefully decanted and then the remaining acid carefully removed with a pipette in order to remove as few pellets from the vessel as possible. The buffer stage was started by adding 900 mL of pre-heated buffer medium.
Sampling for Both Stages
  10 mL aspirated, 8 mL discarded (through Whatman filter (0.7 μm)), 1 mL sampled into HPLC vial.
  The dissolution profiles of the products tested and the comparative dissolution profiles of the budesonide core-shell beads of Example 1 and the three other marketed budesonide containing formulations can be seen in FIG. 6.
  The table below shows the f2 values for comparison of the budesonide capsules according to the invention tested under this method with each of the other commercially available products. An f2 value of 50 or greater is required to demonstrate similarity of the profiles (FDA SUPAC Guidances 1995, 1997).

| Nefecon | Entocort EC | Budenofalk | Cortiment |
|---|---|---|---|
| F2 value (USP) | 18.1 | 16.0 | 15.8 |

It is clear that the release profiles of budesonide differ widely among the four commercial products. None of the f2 comparisons between Nefecon and the other products demonstrated similarity, which would require an f2 value of 50 or greater. In fact, based on the f2 evaluation as well as visual inspection of the graphical profiles, their release profiles must be considered strongly dissimilar.

Example 7: Administration of Bead Filled Capsules and Measurement of Biomarkers For the study detailed in Example 7 to 16 the enteric coated capsules filled with cured beads as described in Example 1 were used. The capsules are referred to below, interchangeably, as "budesonide capsules" or "nefecon budesonide".

Study Design

A randomised, double-blind, placebo-controlled experiment was carried out in which subjects with biopsy-confirmed primary IgA nephropathy and overt proteinuria were administered the budesonide capsules and the levels of various biomarkers were measured in blood taken from those patients: before the commencement of treatment; at the completion of treatment; and, at a timepoint following the completion of treatment.

Patients

Men or women aged at least 18 years with biopsy-confirmed primary IgA nephropathy and overt proteinuria were recruited for the run-in phase. All patients provided written informed consent before enrolment. Inclusion criteria for randomisation to treatment included estimated GFR (eGFR) of at least 45 mL/min per 1.73 m$^2$ and a urine protein creatinine ratio (UPCR) of more than 0.5 g/g or urinary total protein of at least 0.75 g/day—levels that would be considered to increase the risk of progression to end-stage renal disease. Either 24-h protein excretion or UPCR on the 24-h collection of urine were used to determine eligibility to overcome possible collection errors and deviations from normal creatinine excretion (e.g. physically active and muscular men), thus minimising the risk of unintentionally excluding patients.

Procedures

Medication was an oral capsule formulation as described in Example 1 (the budesonide capsule) or placebo, designed with the in vitro dissolution profile as outlined above to provide sustained release of active compound that was delayed until the capsule reached the ileum, particularly the distal ileum, targeting the site with a high density of Peyer's Patches.

After screening, eligible patients were enrolled into a 6-month run-in phase, a 9-month treatment phase, and a 3-month follow-up phase; patient eligibility was assessed before run-in and treatment phases. During run-in, RAS blockade was optimised by up-titrating ACE inhibitors (ACEIs) and angiotensin II receptor blockers (ARBs) to a maximum recommended dose or maximum tolerated dose (in keeping with established clinical practice), to a target blood pressure of less than 130/80 mm Hg, UPCR of less than 0.5 g/g, and urine protein of less than 0.75 g/day. At the end of run-in, patients with persistent proteinuria (UPCR≥0.5 g/g or proteinuria 0.75 g/day) despite optimised RAS blockade, eGFR (estimated by the Chronic Kidney Disease Epidemiology Collaboration [CKD-EPI] serum creatinine equation 45 mL/min) or measured GFR 45 mL/min per 1.73 m$^2$, and blood pressure 160/100 mm Hg or less were eligible for randomisation to treatment.

An independent Data and Safety Monitoring Board (DSMB) monitored all safety issues and reviewed data at the interim analysis.

Randomisation and Masking

Patients were stratified according to their baseline UPCR (0.9 g/g and >0.9 g/g) at month 0 (baseline). Patients were randomly allocated to treatment groups using a computer algorithm method of permuted blocks. Within each block, patients were allocated in a 1:1:1 ratio to 16 mg/day budesonide capsules, 8 mg/day budesonide capsules, or placebo. All patients continued optimised RAS blockade treatment throughout the treatment phase.

In total, 50 patients were given placebo, 51 patients were given 8 mg/day budesonide capsules, and 48 patients were given 16 mg/day budesonide capsules. Randomisation was done by Pharma Consulting Group AB (Uppsala, Sweden). Demographics and baseline characteristics of the recruited patients recruited are shown in Table 2.

The experiment was double-blind. Therefore, throughout the experiment and the analyses, allocation to treatment groups was unknown to each patient, all experimental staff (including the investigators and other staff who performed the randomisation and analyses), the sponsor, and the DSMB (the DSMB reviewed masked safety data and unmasked data were available should there be concerns).

To ensure masking, placebo capsules provided by the sponsor had the same appearance and route of administration as the active capsules. Patients self-administered masked capsules, once daily, 1 h before breakfast during the treatment phase. During follow-up (months 9-12), patients who received 16 mg/day budesonide capsules during months 0-9 were tapered to 8 mg/day for 2 weeks while all other patients (i.e. those who received budesonide capsules 8 mg/day or placebo during months 0-9) received placebo to maintain masking. No further experiment medication was administered after tapering.

TABLE 2

| Patient demographics and baseline characteristics. | | | | |
|---|---|---|---|---|
| Parameter | Placebo (n = 50) | Budesonide Capsules 8 mg/day (n = 51) | Budesonide Capsules 16 mg/day (n = 48) | Total (n = 149) |
| Age | 38.9 (12.0) | 40.6 (13.0) | 37.5 (11.9) | 39.0 (12.3) |
| Sex | | | | |
| Male | 35 (70%) | 37 (73%) | 33 (69%) | 105 (71%) |
| Female | 15 (30%) | 14 (27%) | 15 (31%) | 44 (29%) |
| BMI (kg/m$^2$) | 27.5 (5.4) | 26.5 (4.4) | 27.8 (5.2) | 27.3 (5.0) |
| Weight | 85.2 (18.9) | 80.9 (14.5) | 86.7 (16.9) | 84.2 (16.9) |
| Race | | | | |
| Asian | 1 (2%) | 0 (0%) | 1 (2%) | 2 (1%) |
| Caucasian | 48 (96%) | 49 (96%) | 47 (98%) | 144 (97%) |
| Other | 1 (2%) | 2 (4%) | 0 (0%) | 3 (2%) |

TABLE 2-continued

Patient demographics and baseline characteristics.

| Parameter | Placebo (n = 50) | Budesonide Capsules 8 mg/day (n = 51) | Budesonide Capsules 16 mg/day (n = 48) | Total (n = 149) |
|---|---|---|---|---|
| Ethnicity | | | | |
| Hispanic/Latino | 3 (6%) | 11 (22%) | 7 (15%) | 21 (14%) |
| No-hispanic/Non-Latino | 47 (94%) | 40 (78.4%) | 41 (85.4%) | 128 (85.9%) |
| Blood Pressure (mm Hg) | | | | |
| Systolic | 128.1 (11.9) | 127.7 (13.6) | 126.7 (11.6) | 127.5 (12.3) |
| Diastolic | 80.2 (10.1) | 80.3 (9.7) | 78.1 (9.6) | 79.6 (9.8) |
| UPCR (g/g) | 0.8 (0.5-1.6) | 0.8 (0.5-1.2) | 0.8 (0.5-1.3) | 0.8 (0.5-1.3) |
| 24 h protein excretion (g) | 1.2 (1.0-3.2) | 1.1 (0.9-1.8) | 1.3 (0.9-2.1) | 1.2 (0.9-2.01) |
| UACR (g/g) | 0.7 (0.4-1.3) | 0.7 (0.5-1.0) | 0.7 (0.4-1.2) | 0.7 (0.4-1.1) |
| 24 h albumin excretion (g) | 1.1 (0.8-2.2) | 1.0 (0.7-1.6) | 1.1 (0.8-1.8) | 1.0 (0.8-1.8) |
| eGFR CKD-EPI (creatinine formula; mL/min per 1.73 m$^2$) | 76.5 (23.2) | 74.1 (25.8) | 83.8 (25.9) | 78.3 (25.1) |
| Time from diagnosis to start of treatment (days) | 1101 (294-2870) | 1972 (623-4188) | 1219 (498-2573) | 1499 (496-3162) |

Data are n (%), mean (SD), or median (IQR).
Acronyms:
BMI = body-mass index;
CKD-EPI = Chronic Kidney Disease Epidemiology Collaboration Equation;
eGFR = estimated glomerular filtration rate;
UACR = urine albumin creatinine ratio;
UPCR = urine protein creatinine ratio.

Blood samples were taken from patients at the start of the treatment phase (month 0, before any treatment given), at the conclusion of the treatment phase (month 9), and at the conclusion of the follow-up phase (month 12). The samples obtained were tested for the levels of a number of biomarkers including: BAFF; APRIL; TACI; BCMA; CD27, CD30; secretory IgA; IgA-IgG Immune Complex; and poorly O-galactosylated IgA1.

Treatment code envelopes were provided for each randomised patient. In case of emergency, the code envelope could be opened. Any unmasked patient had to be withdrawn from the experiment.

Example 8: Treatment of Patients with the Budesonide Capsules Leads to a Reduction in Serum Levels of BAFF Materials and Methods Biomarkers were measured using a custom-designed bead-based multiplex Luminex® Assay (R & D Systems) as per the manufacturer's instructions.

The concept of the Luminex® Assay is based on fluorescent tagged microspheres selectively binding to the molecules of interest, thus allowing detection and quantification of multiple biomarkers simultaneously in a very small volume of serum.

In this study, biomarkers were selected and divided into panels (Panel 1: BAFF; APRIL; Panel 2: TACI; BCMA; CD27; CD30) according to the assay dynamic range.

A panel 1-specific tagged microparticle cocktail, or a panel 2-specific tagged microparticle cocktail was diluted 1:10 with the reagent diluent (provided with the microparticles by R & D Systems), serum samples were diluted 1:2 in reagent diluent and serial dilutions of a standard solution (provided with the microparticles by R & D Systems) were used to create a standard curve.

50 μl of microparticle cocktail was applied to the Luminex® Assay plate followed by 50 μl of standard or sample. The plate was incubated on a microplate shaker at 800 rpm at room temperature for 2 hours. Proteins not bound to the microbeads were removed by washing with washing buffer (provided with the microparticles by R & D Systems).

A biotinylated antibody cocktail (provided with the microparticles by R & D Systems) was added to each well and incubated at room temperature for 1 hour. The plate was washed with washing buffer (provided with the microparticles by R & D Systems) and then incubated with 50 μl per well of streptavidin-Phycoerythrin (provided with the microparticles by R & D Systems) for 30-min, followed by a final wash step.

The microparticles were resuspended in 100 μl of wash buffer and the fluorescence in each well was read within 90 mins on the MAGPIX® Luminex machine.

Comparisons of differences in biomarker levels were conducted using a one-way Analysis of variance (ANOVA) statistical test with a p value<0.05.

Results

Figure 7:
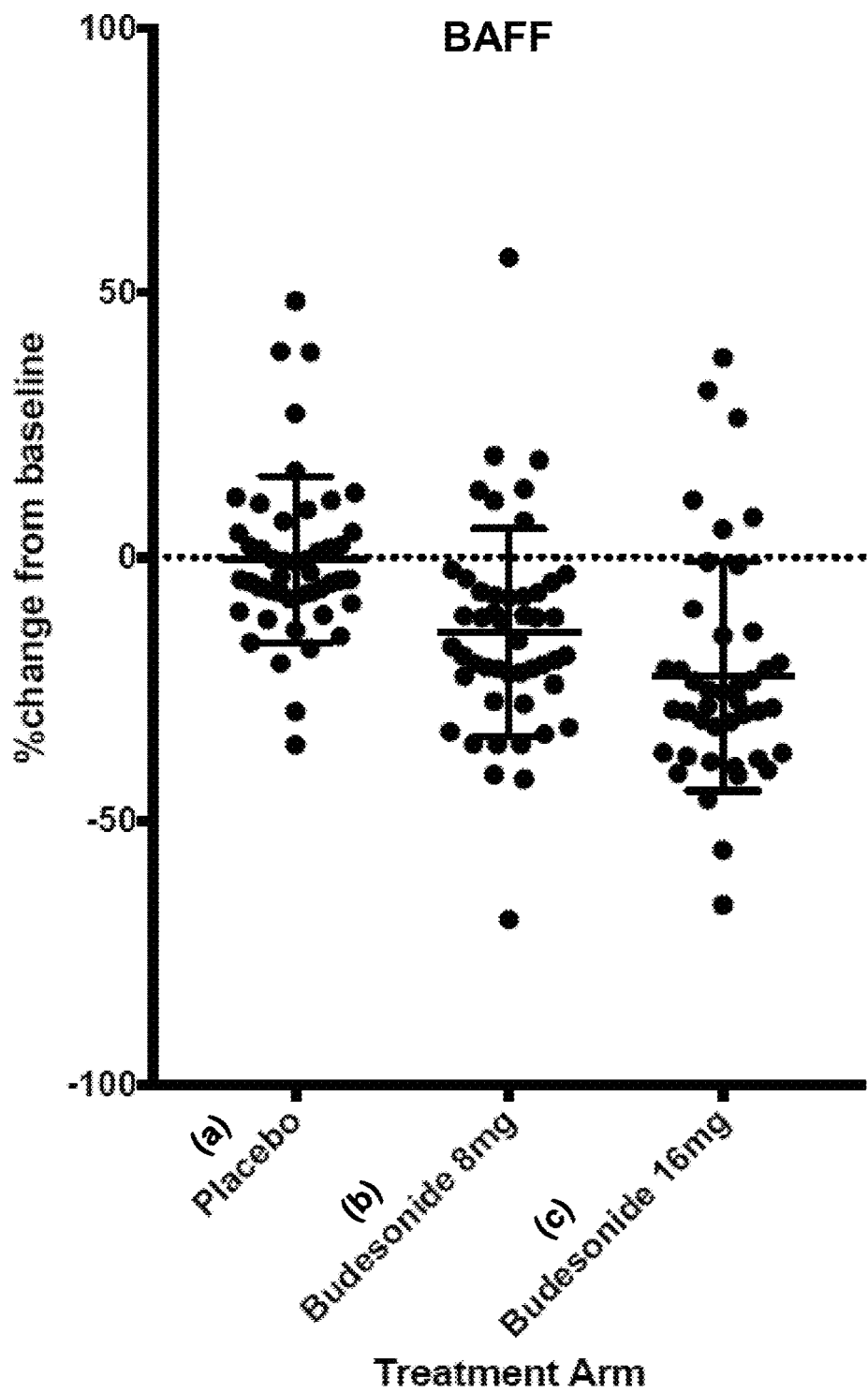
FIG. 7: Percentage change in BAFF level relative to baseline level following treatment. Percentage changes in BAFF relative to baseline levels were measured in patients following 9 months of treatment with: (a) placebo; (b) Nefecon-budesonide (8 mg/day); and (c) Nefecon-budesonide (16 mg/day). The dotted line indicates no percentage change following intervention with placebo or Nefecon-budesonide.

As can be seen in FIG. 7 and Table 3, treatment of patients with the budesonide capsules at 8 mg/day and 16 mg/day led to statistically significant decreases in the serum level of BAFF compared with placebo treated patients in samples taken at the end of the 9-month treatment phase.

TABLE 3

Percentage change in serum levels of BAFF from start to end of treatment.

| Biomarker measured | Placebo | Budesonide Capsules (8 mg/day) | Budesonide Capsules (16 mg/day) | Combined budesonide results |
|---|---|---|---|---|
| BAFF | +0% (+48% to −36%) | −14% (+57% to −69%) | −23% (+38% to −66%) | −18% (+57% to −69%) |

Mean values (Placebo, n = 50; budesonide capsules 8 mg/day n = 51; budesonide capsules 16 mg/day, n = 48; budesonide capsules 8 mg/day and 16 mg/day, n = 99) and range of values shown.

Figure 8:
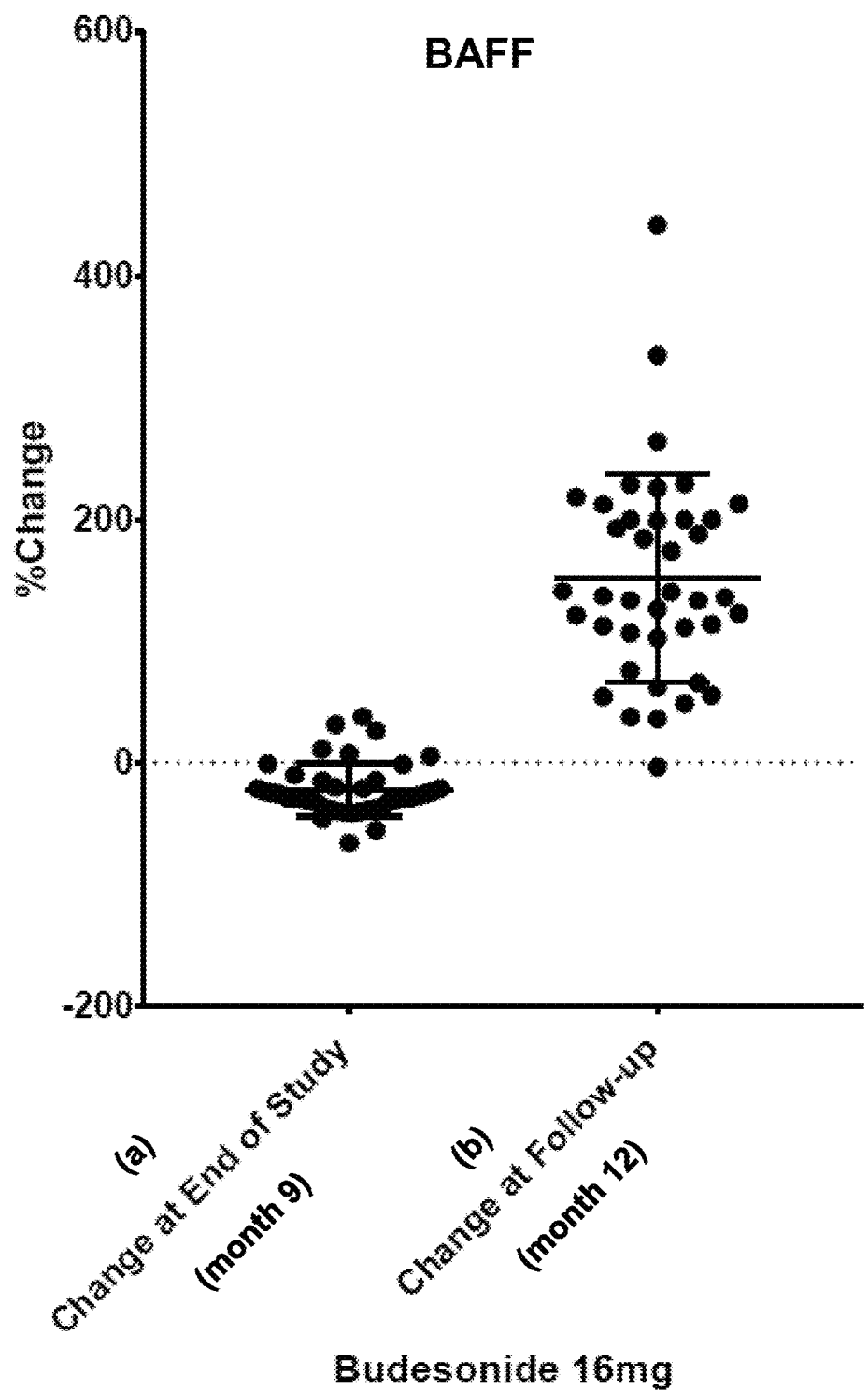
FIG. 8: Percentage change in BAFF level relative to end of treatment level after the follow-up phase. Percentage changes in BAFF were measured in patients given Nefecon-budesonide (16 mg/day) for 9 months at: (a) month 9 at the end of the treatment phase compared to baseline; and (b) at month 12 after the follow-up phase compared to end of treatment. The dotted line indicates no percentage change following intervention with placebo or Nefecon-budesonide.

Furthermore, FIG. 8 and Table 4 show that in serum samples taken after completion of the follow-on phase (i.e. 3 months after the end of the treatment phase), the serum level of BAFF in patients previously treated with 16 mg/day budesonide capsules increases again indicating that the observed reduction was dependent on exposure to budesonide capsules.

TABLE 4

Percentage change in serum levels of BAFF from end of treatment to end of the follow-on phase.

| Biomarker measured | Placebo | Budesonide Capsules (8 mg/day) | Budesonide Capsules (16 mg/day) | Combined budesonide results |
|---|---|---|---|---|
| BAFF | +70% (−4% to −129%) | +29% (−9% to +82%) | +152% (−4% to +442%) | +87% (−9% to +442%) |

Mean values (Placebo, n = 50; budesonide capsules 8 mg/day n = 51; budesonide capsules 16 mg/day, n = 48; budesonide capsules 8 mg/day and 16 mg/day, n = 99) and range of values shown.

The reduction in serum levels of BAFF following treatment with Nefecon budesonide is consistent with a disease-modifying action in IgAN.

Example 9: Treatment of Patients with Budesonide Capsules does not Lead to a Reduction in Serum Levels of APRIL Materials and Methods The same materials and methods were used as described in Example 8 above.

Comparisons of differences in APRIL levels were conducted using a one-way Analysis of variance (ANOVA) statistical test with a p value<0.05.

Results

Figure 9:
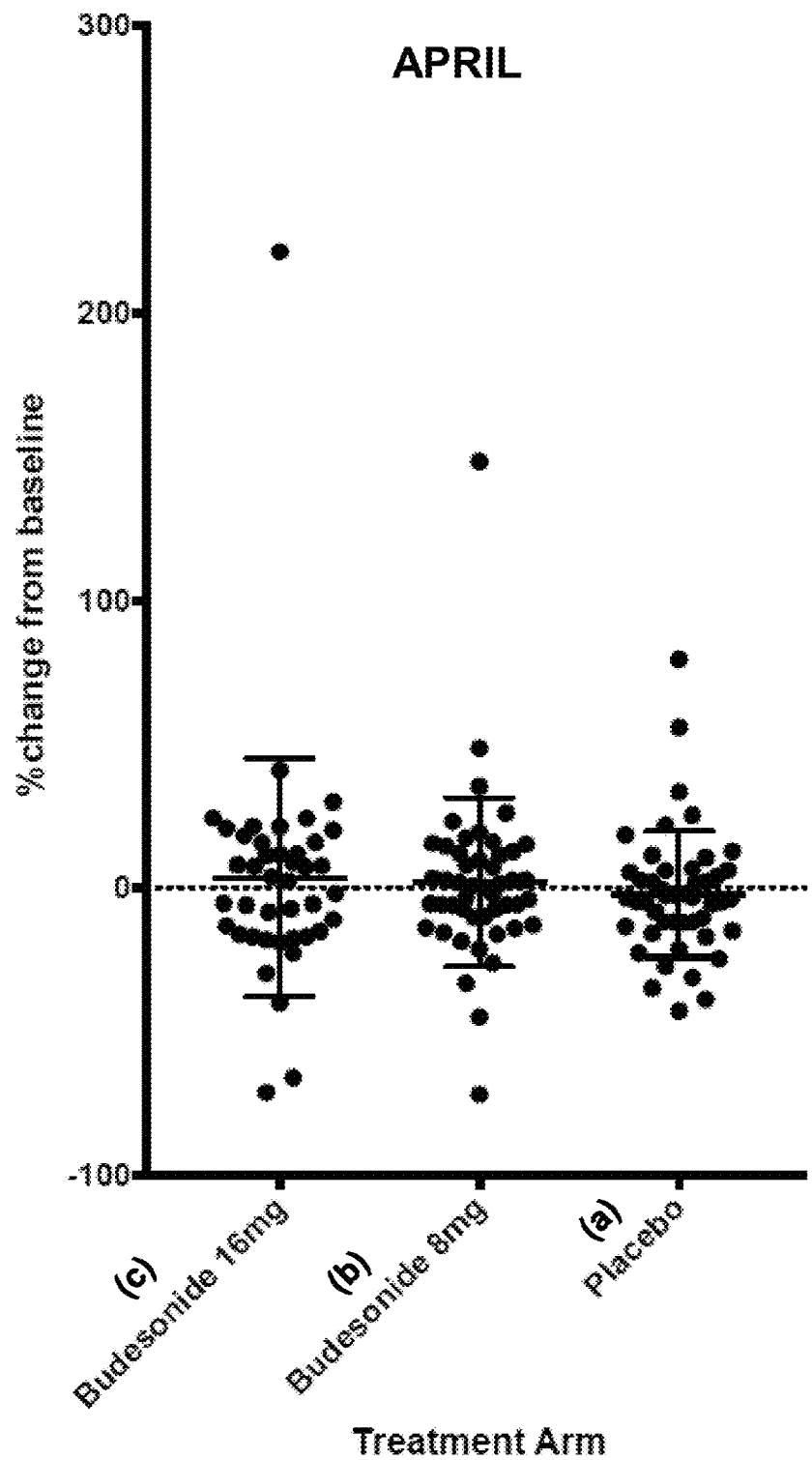
FIG. 9: Percentage change in APRIL level relative to baseline level following treatment. Percentage changes in APRIL levels relative to baseline levels were measured in patients following 9 months of treatment with: (a) placebo; (b) Nefecon-budesonide (8 mg/day); and (c) Nefecon-budesonide (16 mg/day). The dotted line indicates no percentage change following intervention with placebo or Nefecon-budesonide.

As can be seen in FIG. 9 and Table 5, treatment of patients with budesonide capsules at 8 mg/day and 16 mg/day did not lead to an observable change in the serum level of APRIL in samples taken at the end of the 9-month treatment phase, suggesting that the effect produced by treatment with the budesonide capsules is specific to BAFF. Similarly, no change was observed in the placebo group.

TABLE 5

Percentage change in serum levels of APRIL from start to end of treatment.

| Biomarker measured | Placebo | Budesonide capsules (8 mg/day) | Budesonide capsules (16 mg/day) | Combined budesonide results |
|---|---|---|---|---|
| APRIL | −2% (+79% to −43%) | +2% (+148% to −72%) | +3% (+41% to −66%) | +3% (+148% to −72%) |

Mean values (Placebo, n = 50; budesonide capsules 8 mg/day n = 51; budesonide capsules 16 mg/day, n = 48; budesonide capsules 8 mg/day and 16 mg/day, n = 99) and range of values shown.

Example 10: Decrease in Serum Levels of BAFF Following Budesonide Capsule Treatment is Associated with a Reduction in Serum Levels of TACI Materials and Methods The same materials and methods were used as described in Example 8 above.

Comparisons of differences in TACI levels were conducted using a one-way Analysis of variance (ANOVA) statistical test with a p value<0.05.

Results

Figure 10:
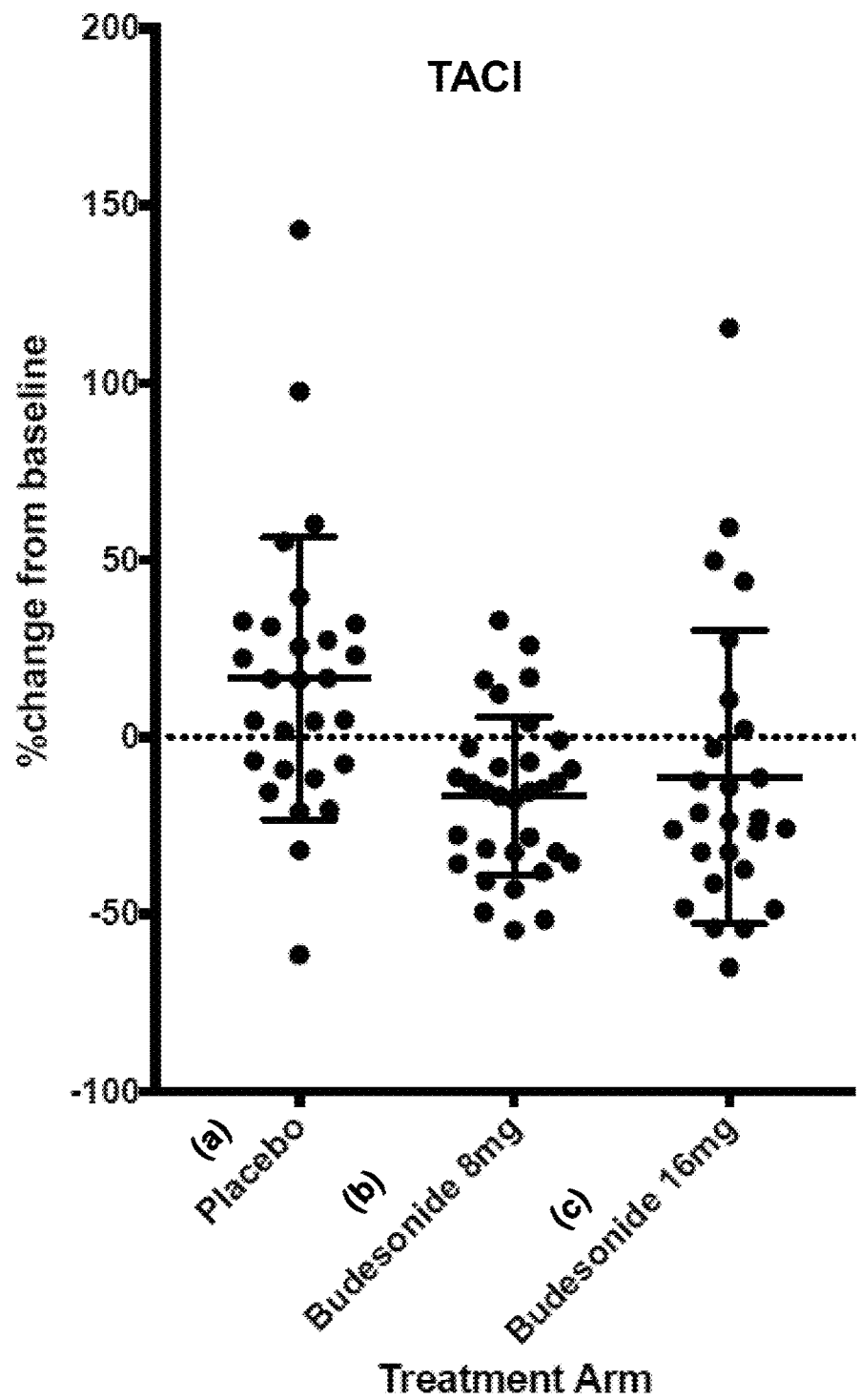
FIG. 10: Percentage change in TACI level relative to baseline level following treatment. Percentage changes in TACI levels relative to baseline levels were measured in patients following 9 months of treatment with: (a) placebo; (b) Nefecon-budesonide (8 mg/day); and (c) Nefecon-budesonide (16 mg/day). The dotted line indicates no percentage change following intervention with placebo or Nefecon-budesonide.

As can be seen in FIG. 10 and Table 6, treatment of patients with budesonide capsules at 8 mg/day and 16 mg/day led to statistically significant decreases in the serum level of TACI compared with placebo treated patients in samples taken at the end of the 9-month treatment phase. In the placebo group, the level of TACI was actually seen to increase slightly, relative to the baseline level.

TABLE 6

Percentage change in serum levels of TACI from start to end of treatment.

| Biomarker measured | Placebo | Budesonide capsules (8 mg/day) | Budesonide capsules (16 mg/day) | Combined budesonide results |
|---|---|---|---|---|
| TACI | +16% (+143% to −61%) | −17% (+26% to −54%) | −11% (+60% to −65%) | −14% (+60% to −65%) |

Mean values (Placebo, n = 50; budesonide capsules 8 mg/day n = 51; budesonide capsules 16 mg/day, n = 48; budesonide capsules 8 mg/day and 16 mg/day, n = 99) and range of values shown.

Example 11: Decrease in Serum Levels of BAFF Following the Budesonide Capsule Treatment is Associated with a Reduction in Serum Levels of BCMA Materials and Methods The same materials and methods were used as described in Example 6 above.

Comparisons of differences in BCMA levels were conducted using a one-way Analysis of variance (ANOVA) statistical test with a p value<0.05.

Results

Figure 11:
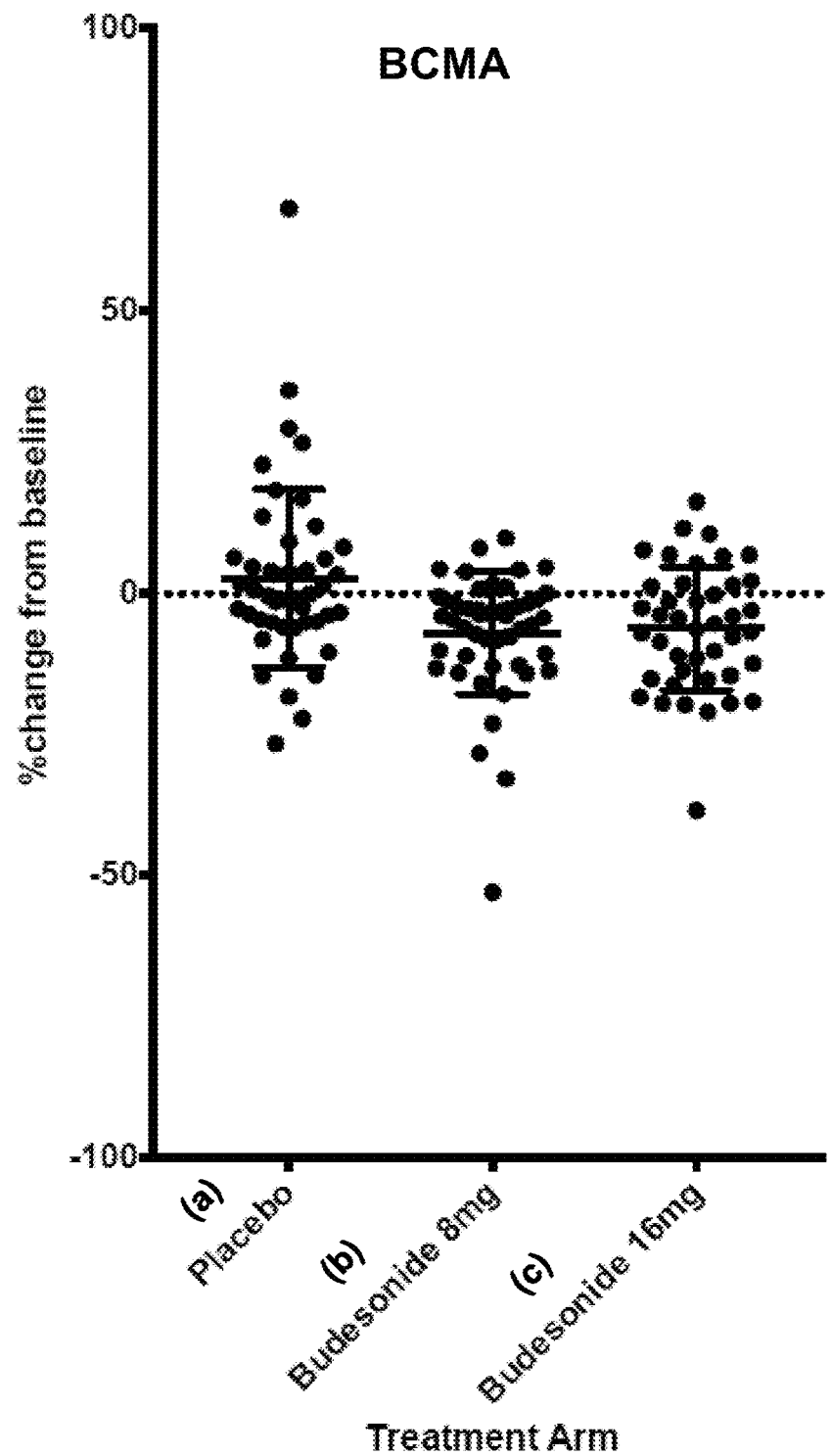
FIG. 11: Percentage change in BCMA level relative to baseline level following treatment. Percentage changes in BCMA levels relative to baseline levels were measured in patients following 9 months of treatment with: (a) placebo; (b) Nefecon-budesonide (8 mg/day); and (c) Nefecon-budesonide (16 mg/day). The dotted line indicates no percentage change following intervention with placebo or Nefecon-budesonide.

As can be seen in FIG. 11 and Table 7, treatment of patients with budesonide capsules at 8 mg/day and 16 mg/day led to a statistically significant decrease in the serum level of BCMA compared with placebo treated patients in samples taken at the end of the 9-month treatment phase. In the placebo group, the level of BCMA was actually seen to increase very slightly relative to the baseline level.

TABLE 7

Percentage change in serum levels of BCMA from start to end of treatment.

| Biomarker measured | Placebo | Budesonide capsules (8 mg/day) | Budesonide capsules (16 mg/day) | Combined budesonide results |
|---|---|---|---|---|
| BCMA | +3% (+68% to −27%) | −7% (+8% to −53%) | −6% (+16% to −39%) | −7% (+16% to −53%) |

Mean values (Placebo, n = 50; budesonide capsules 8 mg/day n = 51; budesonide capsules 16 mg/day, n = 48; budesonide capsules 8 mg/day and 16 mg/day, n = 99) and range of values shown.

Example 12: Decrease in serum levels of BAFF following budesonide capsule treatment is associated with a reduction in serum levels of CD27

As the study was restricted to evaluating changes in the circulating, rather than tissue, levels of each biomarker, and were therefore uncertain of the actual site where modulation occurred, pathway analyses were undertaken to determine whether biomarkers that were significantly modulated by Nefecon budesonide, including those surrogate biomarkers of immune cell activation (including sCD27, and sCD30 (see Example 13)), were associated with any particular biologic processes and pathways.

Materials and Methods

The same materials and methods were used as described in Example 8 above.

Comparisons of differences in CD27 levels were conducted using a one-way Analysis of variance (ANOVA) statistical test with a p value<0.05.

Results

Figure 12:
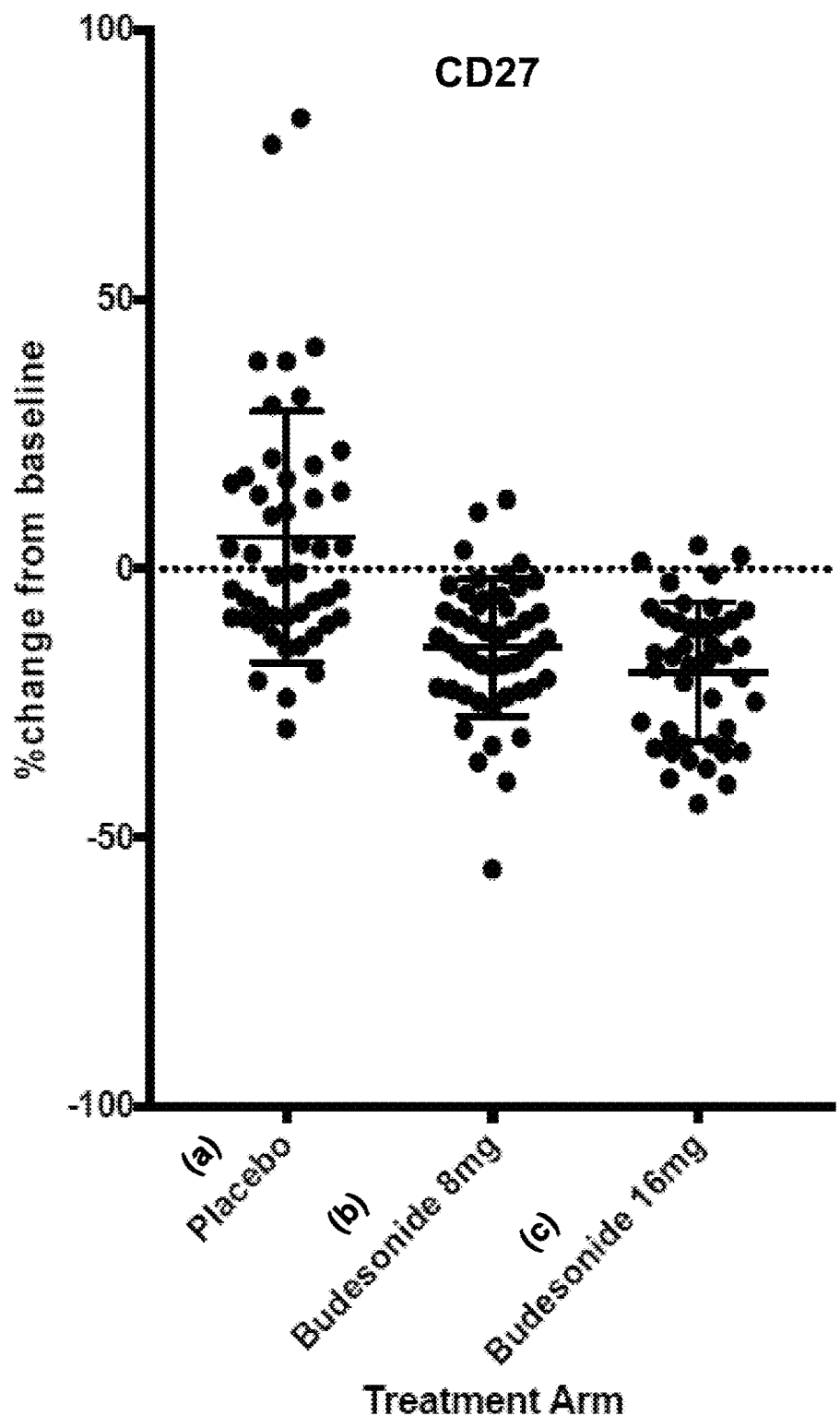
FIG. 12: Percentage change in CD27 level relative to baseline level following treatment. Percentage changes in CD27 levels relative to baseline levels were measured in patients following 9 months of treatment with: (a) placebo; (b) Nefecon-budesonide (8 mg/day); and (c) Nefecon-budesonide (16 mg/day). The dotted line indicates no percentage change following intervention with placebo or Nefecon-budesonide.

As can be seen in FIG. 12 and Table 8, treatment of patients with budesonide capsules at 8 mg/day and 16 mg/day led to a statistically significant decrease in the serum level of CD27 compared with placebo treated patients in samples taken at the end of the 9-month treatment phase. In the placebo group, the level of CD27 was actually seen to increase slightly relative to the baseline level.

TABLE 8

Percentage change in serum levels of CD27 from start to end of treatment.

| Biomarker measured | Placebo | Budesonide capsules (8 mg/day) | Budesonide capsules (16 mg/day) | Combined budesonide results |
|---|---|---|---|---|
| CD27 | +6% (+84% to −30%) | −15% (+10% to −56%) | −19% (+4% to −44%) | −17% (+10% to −56%) |

Mean values (Placebo, n = 50; budesonide capsules 8 mg/day n = 51; budesonide capsules 16 mg/day, n = 48; budesonide capsules 8 mg/day and 16 mg/day, n = 99) and range of values shown.

Figure 13:
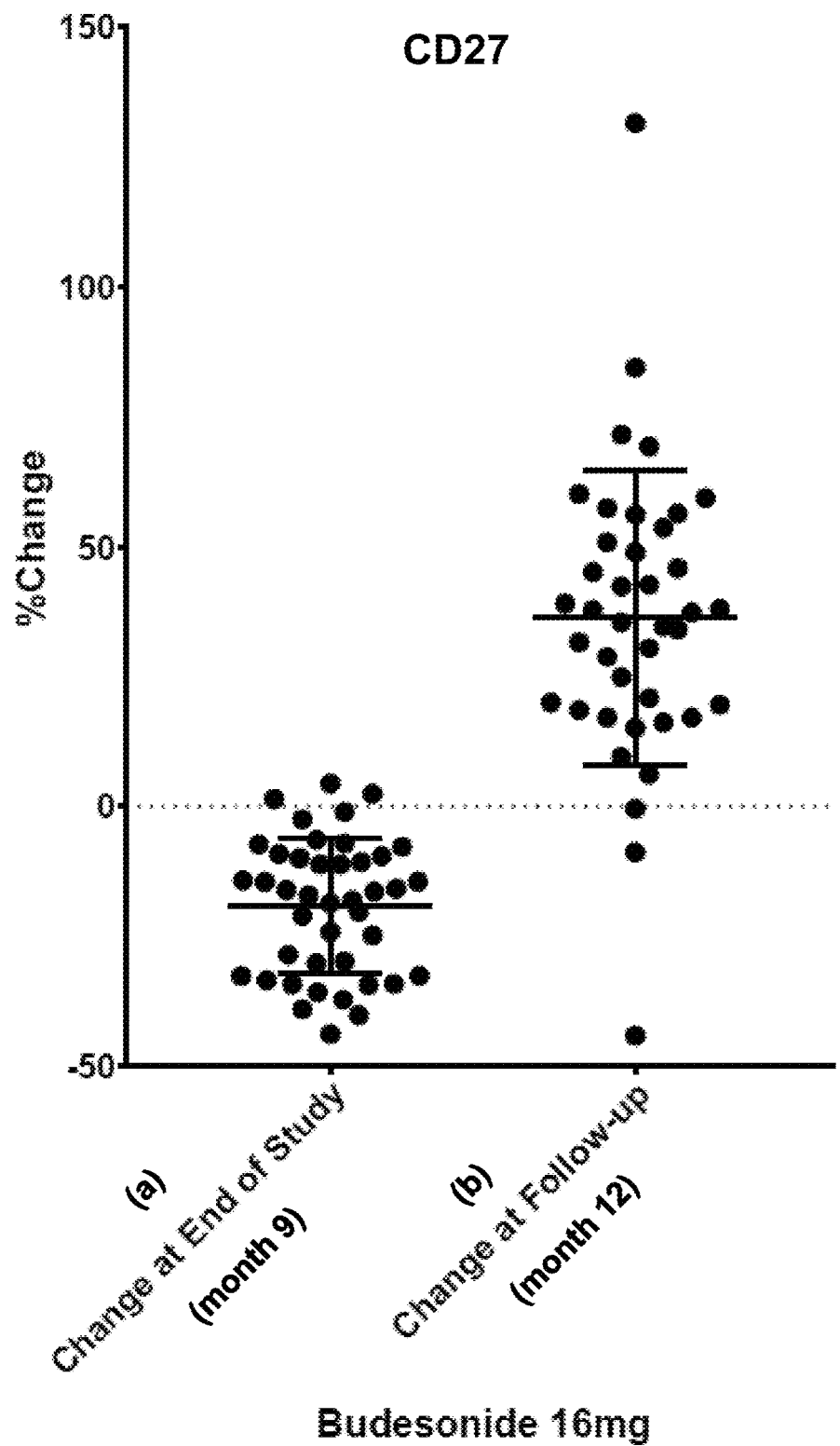
FIG. 13: Percentage change in CD27 level relative to end of treatment level after the follow-up phase. Percentage changes in CD27 were measured in patients given Nefecon-budesonide (16 mg/day) for 9 months at: (a) month 9 at the end of the treatment phase compared to baseline; and (b) at month 12 after the follow-up phase compared to end of treatment. The dotted line indicates no % change following intervention with placebo or Nefecon-budesonide.

Furthermore, FIG. 13 and Table 9 show that in samples taken after completion of the follow-on phase (i.e. 3 months after the end of the treatment phase), the serum level of CD27 in patients previously treated with 16 mg/day budesonide capsules increases again indicating that the observed reduction was dependent on exposure to the budesonide capsules.

TABLE 9

Percentage change in serum levels of CD27 from end of treatment to end of the follow-on phase.

| Biomarker measured | Placebo | Budesonide capsules (8 mg/day) | Budesonide capsules (16 mg/day) | Combined budesonide results |
|---|---|---|---|---|
| CD27 | +16% (−14% to +65%) | +20% (−2% to +183%) | +36% (0% to +132%) | +28% (−2% to +183%) |

Mean values (Placebo, n = 50; budesonide capsules 8 mg/day n = 51; budesonide capsules 16 mg/day, n = 48; budesonide capsules 8 mg/day and 16 mg/day, n = 99) and range of values shown.

Example 13: Decrease in Serum Levels of BAFF Following Budesonide Capsule Treatment is Associated with a Reduction in Serum Levels of CD30

Materials and Methods

The same materials and methods were used as described in Example 8 above.

Comparisons of differences in CD30 levels were conducted using a one-way Analysis of variance (ANOVA) statistical test with a p value<0.05.

Results

Figure 14:
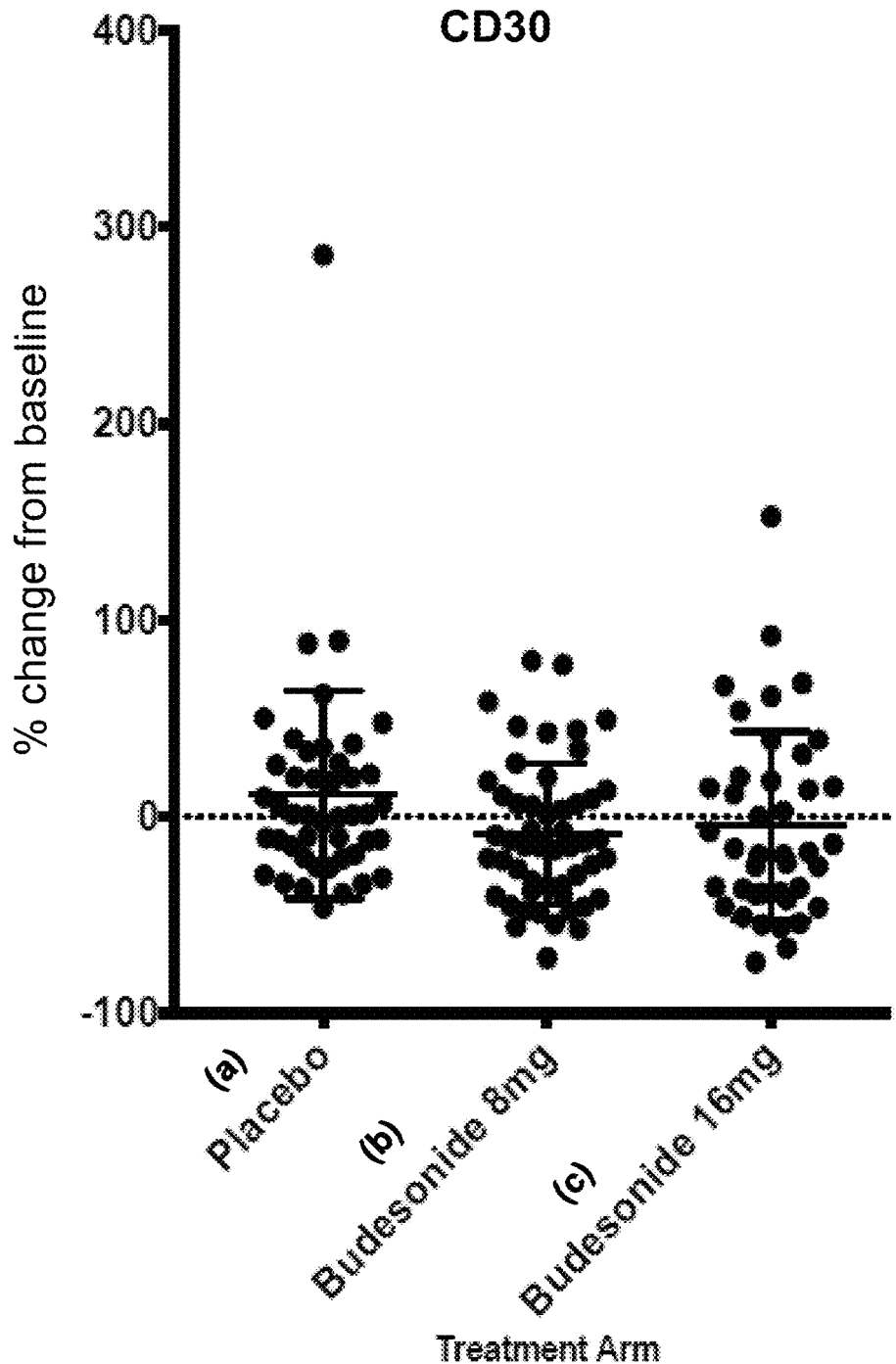
FIG. 14: Percentage change in CD30 level relative to baseline level following treatment. Percentage changes in CD30 levels relative to baseline levels were measured in patients following 9 months of treatment with: (a) placebo; (b) Nefecon-budesonide (8 mg/day); and (c) Nefecon-budesonide (16 mg/day). The dotted line indicates no percentage change following intervention with placebo or Nefecon-budesonide.

As can be seen in FIG. 14 and Table 10, treatment of patients with budesonide capsules at 8 mg/day and 16 mg/day led to a small but statistically significant decrease in the serum level of CD30 compared with placebo treated patients in samples taken at the end of the 9-month treatment phase. In the placebo group, the level of CD30 was actually seen to increase slightly relative to the baseline level.

TABLE 10

Percentage change in serum levels of CD30 from start to end of treatment.

| Biomarker measured | Placebo | Budesonide capsules (8 mg/day) | Budesonide capsules (16 mg/day) | Combined budesonide results |
|---|---|---|---|---|
| CD30 | +11% (+88% to −46%) | −8% (+80% to −72%) | −5% (+92% to −67%) | −6% (+92% to −72%) |

Mean values (Placebo, n = 50; budesonide capsules 8 mg/day n = 51; budesonide capsules 16 mg/day, n = 48; budesonide capsules 8 mg/day and 16 mg/day, n = 99) and range of values shown.

Consistent with the large meta-analysis of genome-wide association (GWA) studies (Gesualdo L, Di Leo V, Coppo R. The mucosal immune system and IgA nephropathy. Semin Immunopathol. 2021; 43:657-668; Coppo R. The gut-renal connection in IgA nephropathy. Semin Nephrol. 2018; 38:504-512.), this study identified the intestinal immune network for IgA production as one of the most enriched Kyoto Encyclopaedia of Genes and Genomes (KEGG) pathways, indicating that the mechanism of action of Nefecon budesonide is, at least in part, driven by an effect within the ileal gut-associated lymphoid tissue (GALT).

Example 14: Analysis of Secretory IgA Levels Following Budesonide Capsule Treatment Materials and Methods Monoclonal mouse anti-human secretory component (Sigma) diluted 1:10,000 in coating buffer was applied to the wells of an immunoplate and incubated at 4° C. overnight. The plate was then washed and blocked with 2% BSA for 1 hour at room temperature. Serum samples and standards (high, medium, and low) were diluted 1:10 in PBS and applied to the plate, following washing, and incubated at 4° C. overnight. Following this, the plate was washed and polyclonal rabbit anti-human IgA HRP (Sigma, 1:2000) was added to each well, and the plate was incubated at room temperature for 90 minutes. The plate was then washed again, and levels of secretory IgA were visualized with o-phenylenediamine dihydrochloride substrate. OD492 of the high, medium, and low standards on each plate was used to normalize the values of the plates to a standard plate.

Results

Figure 15:
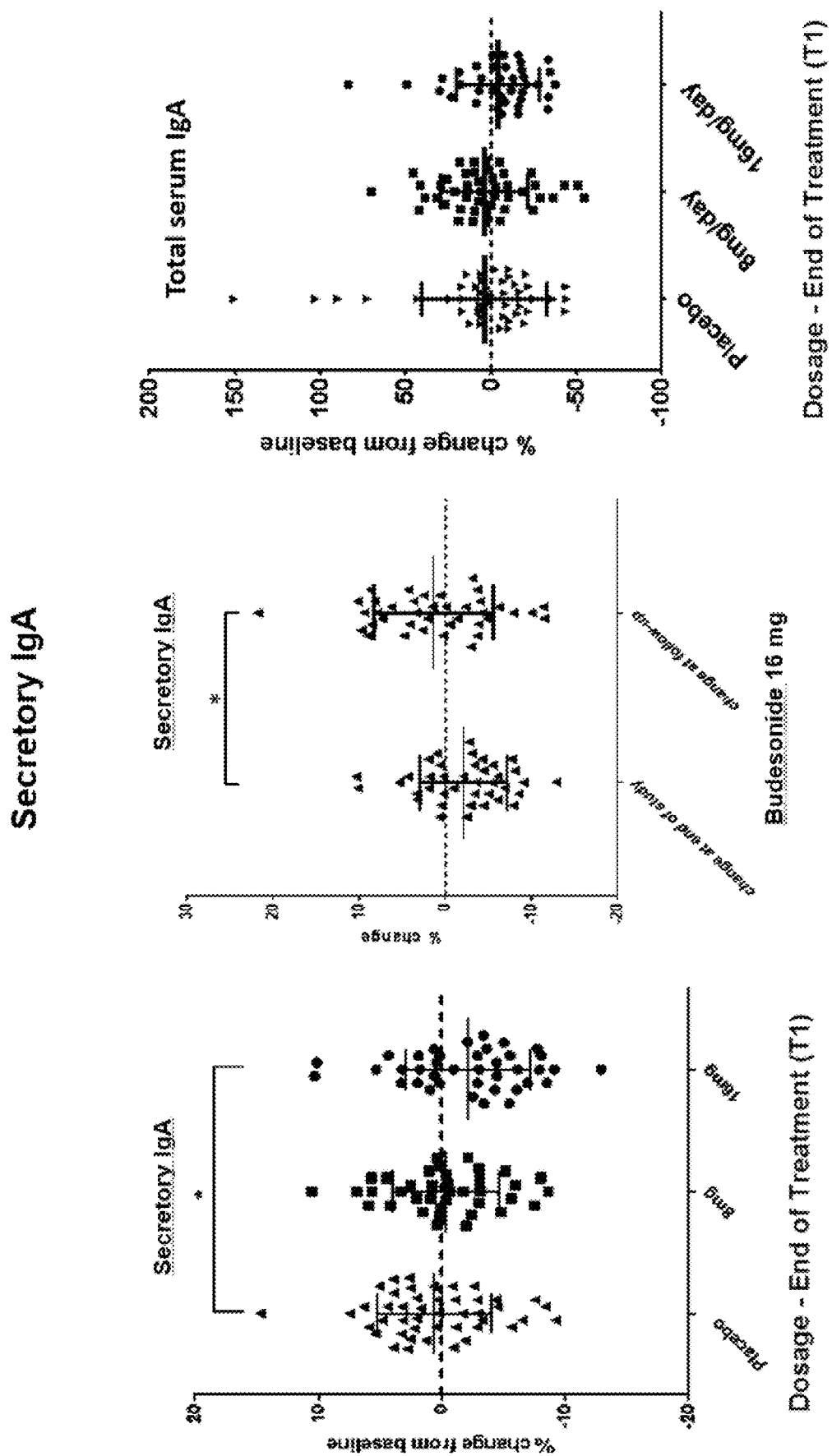
FIG. 15: shows that there were significant ($p<0.05$) budesonide capsule-dependent decreases in the serum levels of secretory IgA. Whereas serum levels of IgA did not change.

There were significant (p<0.05) budesonide capsule-dependent decreases in the serum levels of secretory IgA. Serum levels of secretory IgA did not change (FIG. 15). This is indicative of local release and local gut action of the targeted release of the budesonide capsules, rather than systemic exposure of budesonide

Example 15: Analysis of IgA-IgG Immune Complex and Poorly O-Galactosylated IgA1 Levels Following Budesonide Capsule Treatment Materials and Methods IgA-IgG immune complexes: Wells from a 96-well immunoplate were coated with AffiniPure F(ab')2 fragment goat anti-human serum IgA (a chain specific) (Jackson Immunology) diluted to 5 µg/mL in coating buffer. Following overnight incubation at 4° C., the plate was washed and non-specific protein binding was blocked with 2% BSA in PBS for 1 hour at room temperature. The test serum samples and standards (high, medium, and low) were diluted 1:500 in PBS, added to duplicate wells, and incubated at 4° C. overnight. The plate was then washed and incubated for 90 minutes with polyclonal rabbit anti-human IgG-HRP (Dako) diluted 1:2000 in PBS. The plate was washed again for 4 cycles, and levels of IgA/IgG ICs in the serum samples were visualized using o-phenylenediamine dihydrochloride substrate. OD492 of the high, medium, and low standards on each plate was used to normalize the values of the plates to a standard plate.

Undergalactosylated IgA: Levels of poorly O-galactosylated IgA1 were measured using a commercially available KM55 ELISA (cat no 27600, Immuno-Biological Laboratories, Inc. Minneapolis, MN 55432, USA)

Results

Figure 16:
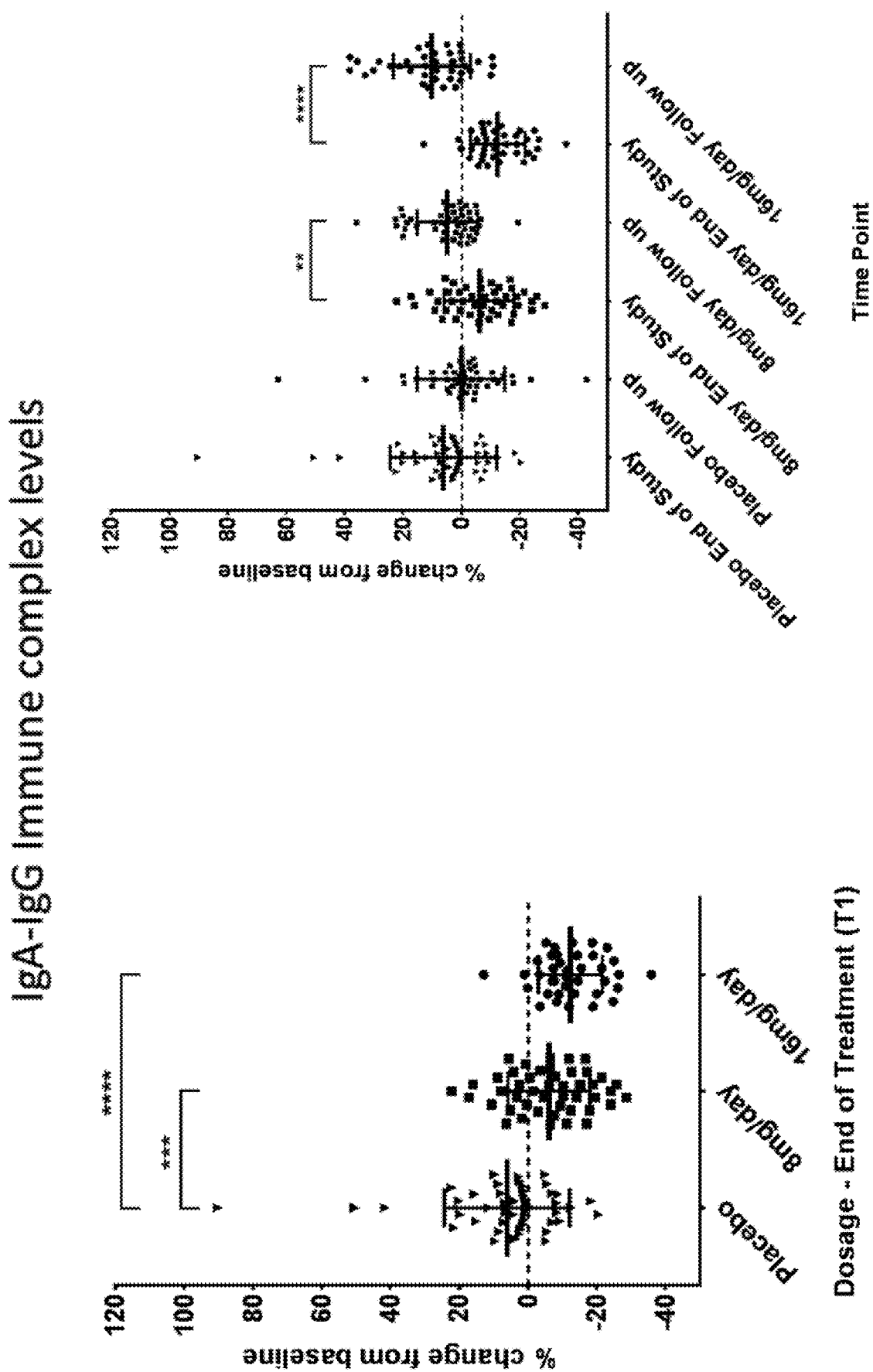
FIG. 16: shows that there was a significant ($p<0.05$) budesonide capsule dose-dependent decrease in the serum levels of IgA-IgG immune complexes.
Figure 17:
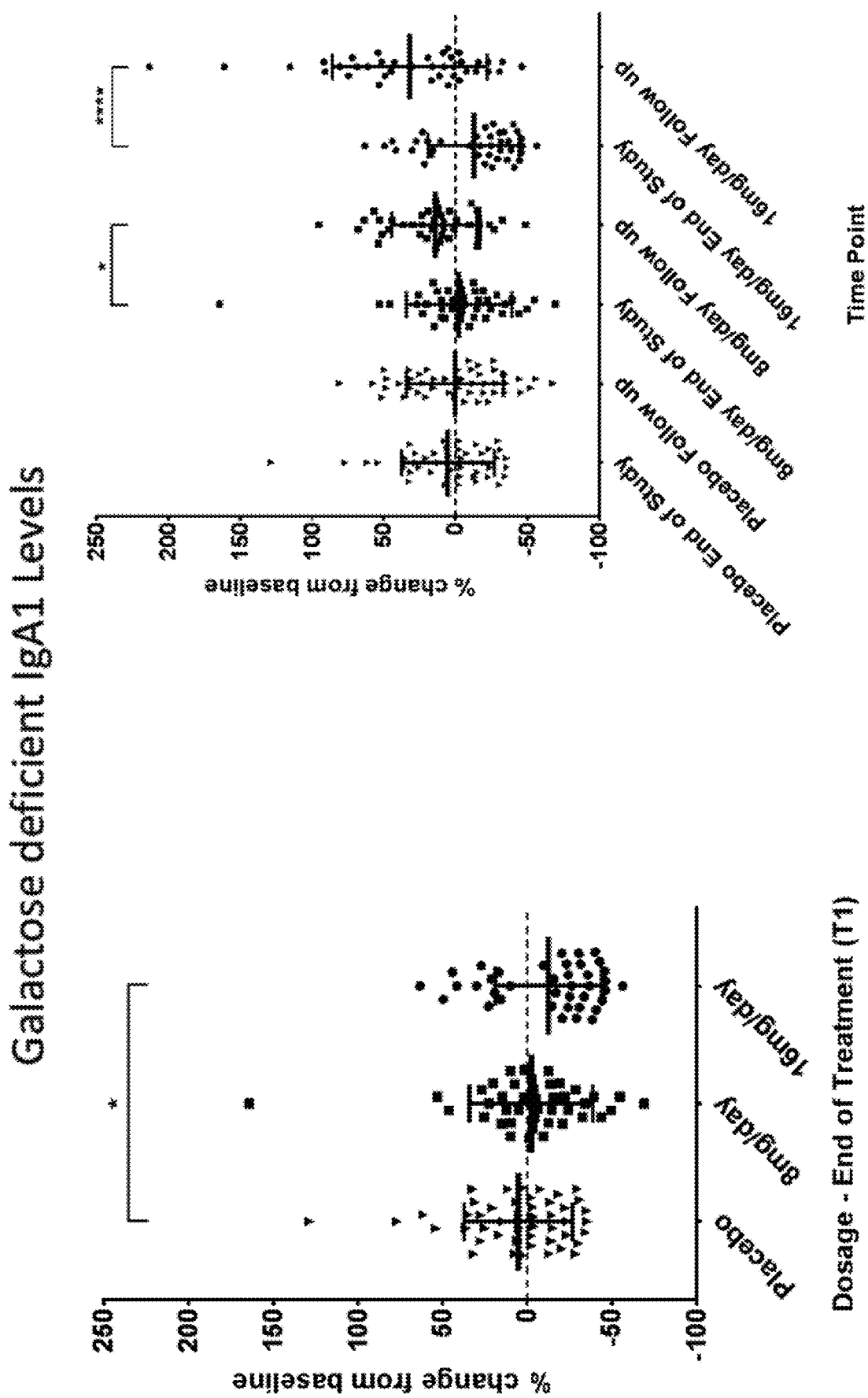
FIG. 17: shows that there was a significant ($p<0.05$) budesonide capsule dose-dependent decrease in the levels of poorly O-galactosylated IgA1.

At the end of the treatment there was a significant (p<0.05) budesonide capsule dose-dependent decrease in the serum levels of IgA-IgG immune complexes. IgA-IgG immune complex levels returned to baseline levels over the 3 months following cessation of budesonide capsule treatment (FIG. 16). There was a similar, although less pronounced, change in the levels of poorly O-galactosylated IgA1 (FIG. 17).

Figure 18:
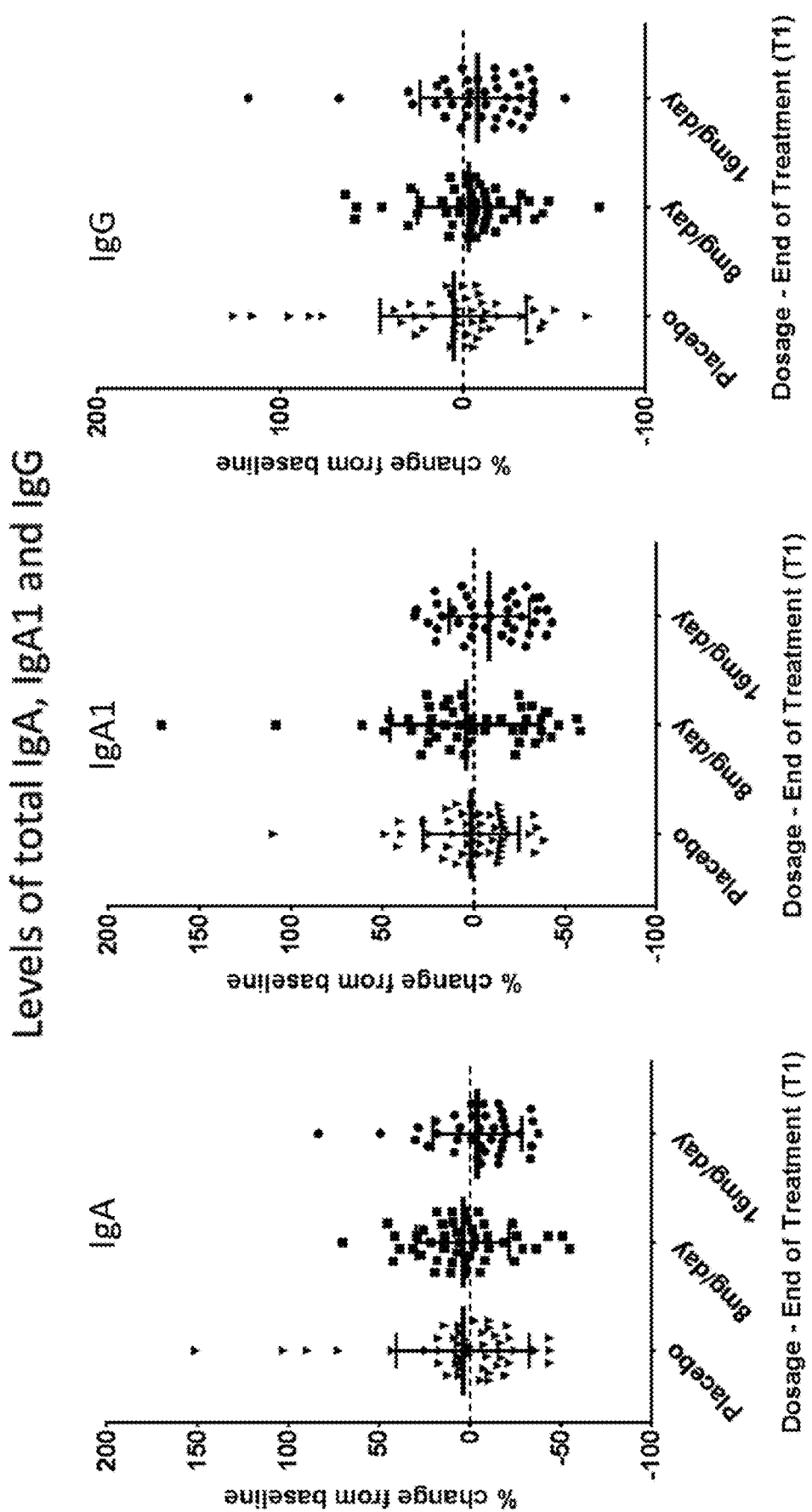
FIG. 18: shows that there were no differences observed in levels of total IgA, IgA1 and IgG with budesonide capsule treatment.

What is particularly interesting is that it has been shown that treatment of IgAN with systemic glucocorticoids lowers both total serum IgA and O-galactosylated IgA1 (Kosztyu P et al.: Glucocorticoids Reduce Aberrant O-Glycosylation of IgA1 in IgA Nephropathy Patients. Kidney Blood Press Res 2018; 43:350-359. However, with the present treatment there were no differences observed in levels of total IgA, IgA1 and IgG with budesonide capsule treatment (FIG. 18), which led us to conclude that the effect of local ileal treatment with budesonide capsules was selective for the pathogenic antibodies but not effective on the general pool of IgA, IgA1 and IgG.

These results show that treatment with Nefecon budesonide is supportive of a direct effect of Nefecon budesonide on the underlying pathogenic pathways in IgAN and that the budesonide payload has a predominantly topical effect rather than a systemic effect, leading to reduced side effects for patients when treated with Nefecon budesonide.

Example 16: Comparison of Lag Times for Onset of Plasma Profiles Between the Budesonide Capsules and Reference Commercial Product A test product of the budesonide capsules (obtained according to Example 1 above) and a reference commercial product (Entocort® EC; AstraZeneca) containing the same active ingredient were administered to 24 subjects in the fasted state in a randomized, crossover clinical study.

The lag times in hours for the onset of blood levels for each subject after administration of the test formulation on two separate occasions, and for the administration of the Reference (REF) product (with suitable wash-out period of 7 to 14 days), are shown in Table 11 below.

TABLE 11

| | Lag times for onset of plasma profiles | | |
|---|---|---|---|
| Subject No. | Test Formulation Administration 1 (F1) | Test Formulation Administration 2 (F2) | REF product |
| 14 | 8 | 4 | 0.67 |
| 38 | 3.5 | 3 | 0.67 |
| 40 | 4 | 4.5 | 1 |
| 41 | 4.5 | 4 | 0.67 |
| 19 | 1 | 2.5 | 0.67 |
| 28 | 2.5 | 6 | 0.67 |
| 29 | 4 | 4 | 0.67 |
| 36 | 3 | 3.5 | 1.5 |
| 01 | 4.5 | 6 | 1.5 |
| 03 | 4 | 4.5 | 1 |
| 15 | 3.5 | 3.5 | 1 |
| 20 | 4 | 4 | 0.67 |
| 04 | 4.5 | 3.5 | 1 |
| 08 | 2.5 | 3 | 0.67 |
| 10 | 4 | 3.5 | 1 |
| 12 | 4.5 | 5 | 1 |
| 06 | 5.5 | / | / |
| 17 | 5 | 4 | 1 |
| 22 | 4 | 3.5 | 0.33 |
| 34 | 3.5 | 4 | 1 |

TABLE 11-continued

| | Lag times for onset of plasma profiles | | |
|---|---|---|---|
| Subject No. | Test Formulation Administration 1 (F1) | Test Formulation Administration 2 (F2) | REF product |
| 09 | 3 | 4 | 2 |
| 11 | 2.5 | 3.5 | 0.67 |
| 16 | 4 | 4.5 | 0.67 |
| 42 | 3 | 6 | 1.5 |

Statistical Analysis

Data were analysed with Sigmaplot for Windows, version 11.0.

Descriptive Statistics

Median values were calculated for the lag times to onset of plasma level for each arm of the study and are presented in Table 12 below. (Median values are reported rather than mean values because these are discrete data i.e., lag times can only correspond to the sampling times in the study).

TABLE 12

| | | Median lag time values | | |
|---|---|---|---|---|
| Group | N | Median | $25^{th}$ percentile | $75^{th}$ percentile |
| F1 | 24 | 4.000 | 3.000 | 4.500 |
| F2 | 24 | 4.000 | 3.500 | 4.500 |
| REF | 24 | 1.000 | 0.670 | 1.000 |

It was concluded that the Median value ($50^{th}$ percentile) of the lag time to onset of plasma levels was 4 hours for both administrations of test formulation and 1 hour for the reference commercial formulation.

To determine whether the lag times observed for the test formulation were statistically different to those for the Reference product, two Repeated Measures Analysis of Variance (ANOVA) tests were applied to the data—one assuming that the data are normally distributed, and one with no assumption about how the data are distributed.

The Repeated Measures Analysis of Variance assuming a normally distributed data set resulted in an F value of 51.815 and a P value of P<0.001, which is highly statistically significant. A post-hoc comparison using a Tukey test to determine which arms of the study were different to each other gave the results presented in Table 13 below:

TABLE 13

| | Post-hoc comparison between arms of study | | | |
|---|---|---|---|---|
| Comparison | Difference of Means | q-statistic | P Value | P <0.050 |
| F2 vs. REF | 3.151 | 18.005 | <0.001 | Yes |
| F2 vs. F1 | 0.261 | 1.517 | 0.820 | No |
| F1 vs. REF | 2.890 | 16.770 | <0.001 | Yes |

This showed that, whereas there is no difference in the lag time to onset of plasma levels whenever the test formulation was administered on separate occasions, the lag time to onset of plasma levels following administration of test formulation is highly statistically different (P<0.001) compared to when the commercial reference product is administered.

A Repeated Measures Analysis of Variance was also applied to rankings of the individual lag time values using the Friedman test (see e.g. Stanton. A Glanz, Primer of Biostatistics, 5th Edition, McGraw Hill 2002, ISBN 0-07-137946-0, pages 370-380).

Using this test, the Chi-square value was 52.950, resulting in a P value of <0.001, which is highly statistically significant. A post-hoc comparison using a Tukey test to determine which arms of the study were different to each other gave the results presented in Table 14 below:

TABLE 14

Post-hoc comparison between arms of study

| Comparison | Difference of Ranks | q-statistic | P <0.05 |
|---|---|---|---|
| F2 vs REF | 68.500 | 9.237 | Yes |
| F2 vs F1 | 9.500 | 1.281 | No |
| F1 vs REF | 59.000 | 7.956 | Yes |

This test shows (again) that, whereas there is no difference in the lag time to onset of plasma levels when test formulation is administered on separate occasions, the lag time to onset of plasma levels when test formulation is administered is statistically different (P<0.05) to when the commercial reference formulation is administered.

In conclusion, the test formulation has a significantly different lag time to onset of plasma levels compared to the commercial reference formulation, Entocort® EC, irrespective of the type of statistical analysis that is applied. The median lag time to onset of plasma levels was 4 hours in each of the arms of the study in which Nefecon F was administered, while the median lag time for Entocort® EC was 1 hour.

This analysis clearly demonstrates that, unlike the Reference product, the test formulation as described and claimed herein does not release the bulk of its active ingredient until the distal part of the small intestine (e.g., the ileum, such as the distal ileum) is reached.

Example 17: General Process for Standard In Vitro Dissolution Test According to USP<711>/pH.Eur. 2.9.3 in the Presence of Added Surfactant Tween 80

The in vitro dissolution of the encapsulated budesonide core-shell beads of Example 1 were analysed as described in Ph.Eur. 2.9.3 Dissolution test for solid dosage forms (using Apparatus 2) and as described in USP <711> Dissolution (using Apparatus 2). The measurement was carried out as described below.

Three marketed budesonide-containing formulations were also analysed in this test. The three formulations being Entocort® (Tillotts Pharma), Budenofalk® (Dr Falk Pharma GmbH) and Cortiment® (Ferring Pharmaceuticals, CH).

| Dissolution Apparatus Setup | |
|---|---|
| Dissolution Apparatus: | USP <711>/Ph. Eur. 2.9.3 Apparatus 2 |
| Vessel Size/Type: | 1000 mL/clear glass, round-bottom |
| Rotation Speed: | 100 rpm |
| Media Volume: | 900 mL - Acid Resistance |
| | 900 mL - Buffer Dissolution Profile |
| Test Temperature: | 37.0 ± 0.5° C. |
| Pull Volume: | 15 mL |
| Replacement: | No |
| Sampling Time Point: | Acid Resistance Stage: |
| | 2 hours |

-continued

| Dissolution Apparatus Setup | |
|---|---|
| pH check | Buffer Stage: 15, 30, 45, 60, 90, 120, 180 minutes Check the pH of the dissolution medium before and in each vessel after each test and record the result (Buffer Dissolution Medium only) |

Budesonide release was measured using Ultra Performance Liquid Chromatography (UPLC).

Reagents and Standards

Standards and Reference Materials:

Budesonide, Ph. Eur. CSR or suitable secondary standard.

Other Reagents:

Tween 80, (Polysorbate (80)), Fisher Scientific or equivalent.

Dissolution Media and Diluents

Acid Resistance Media 0.1 N HCl Solution. To prepare 6 L of acid resistance media, 50 mL of concentrated HCl was combined with 6000 mL of water and the resulting solution was mixed well.

Buffer Dissolution Media

FaSSIF Buffer Concentrate (from Biorelevant.com, product code FASBUF01) was used to prepare the Buffer solution.

A 0.05 w/v % (0.5 mg/mL) Tween 80 to the Buffer Solution: for example, To make 6 L of the Buffer Dissolution Medium, 3 g of Tween 80 was added to 6 L of the Buffer solution, to arrive at a Tween 80 concentration of 0.05 w/v %.

The resulting solution was mixed well and the pH was checked. If necessary, the pH was adjusted to 6.5±0.05 using either Hydrochloric Acid or Sodium Hydroxide.

Budesonide release was assessed based on the acceptance criteria in USP<711>/Ph.Eur. 2.9.3.

Example 18: Dissolution Profile Analysis of Budesonide Capsules According to In Vitro USP<711>/Pharmacopeia Test No. 2.9.3 in the Presence of Added Surfactant Tween 80

The enteric coated capsules filled with cured beads ("budesonide capsules") prepared as described in Example 1 above were tested under the dissolution conditions outlined in Example 17.

Figure 19:
FIG. 19: shows the in vitro dissolution profile of budesonide modified release capsules in the presence of added surfactant in the Level 1 fasted state 35 simulated intestinal fluid at a pH of about 6.5.

The overall average dissolution profile for three samples in the buffer stage can be seen in FIG. 19. No budesonide release was observed in the acid resistance stage at the 2 hour sampling time point.

The quantitative results of the dissolution of budesonide in the various media at time points 2 hours at pH 1.2, and 15, 30, 45, 60, 90, 120, and 180 minutes in the buffer stage at pH 6.5 are provided in the table below.

| | Acid Budesonide Release (%) | Buffer Stage Budesonide Release (%) | | | | | | |
|---|---|---|---|---|---|---|---|---|
| | | Time (min) | | | | | | |
| | 120 | 15 | 30 | 45 | 60 | 90 | 120 | 180 |
| Vessel 1 | 0 | 0 | 0 | 0 | 0 | 56.9 | 85.0 | 97.6 |
| Vessel 2 | 0 | 0 | 0 | 0 | 0 | 50.0 | 83.7 | 97.5 |
| Vessel 3 | 0 | 0 | 0 | 0 | 0 | 45.8 | 85.0 | 101.4 |

| Acid Budesonide Release (%) | Buffer Stage Budesonide Release (%) | | | | | | |
|---|---|---|---|---|---|---|---|
| | Time (min) | | | | | | |
| 120 | 15 | 30 | 45 | 60 | 90 | 120 | 180 |
| Mean 0 | 0 | 0 | 0 | 0 | 50.9 | 84.6 | 98.8 |
| Range 0-0 | 0-0 | 0-0 | 0-0 | 0-0 | 46-57 | 84-85 | 97-101 |
| SD 0 | 0 | 0 | 0 | 0 | 5.6 | 0.8 | 2.3 |

*SD—standard deviation

The budesonide release was assessed based on the acceptance criteria in USP<711>/Ph.Eur. 2.9.3.

For comparison, the dissolution profiles of budesonide capsules and three other budesonide-containing formulations were obtained according to the protocol outlined below. The three other budesonide-containing formulations being Entocort® (Tillots Pharma), Budenofalk® (Dr Falk Pharma GmbH) and Cortiment® (Ferring Pharmaceuticals, CH).

| Method for capsules | |
|---|---|
| Dissolution Apparatus Apparatus: | USP <711>/Ph. Eur. 2.9.3 Apparatus 2 |
| Vessel Size/Type: | 1000 mL/clear glass, round-bottom |
| Rotation Speed: | 100 rpm |
| Media Volume: | 900 mL - Acid Resistance 900 mL - Buffer Dissolution Profile |
| Test Temperature: | 37.0 ± 0.5° C. |
| Pull Volume: | 10 mL |
| Replacement: | No |
| Sampling Time Points | Acid Resistance Stage: 2 hours Buffer Stage: 15, 30, 45, 60, 90, 120, 180 minutes |
| pH check | Check the pH of the dissolution medium after preparation, and again in each vessel after each test and record the result (Buffer Dissolution Medium only). |

Standards and Reference Materials
  Budesonide, Ph. Eur. CSR.
  Other Reagents:
  Tween 80, (Polysorbate (80)), Fisher Scientific or equivalent.
Dissolution Media, Mobile Phase and Diluents
  Acid Resistance Media
  0.1N HCl Solution. For example, to prepare 10 L, 82 mL of concentrated HCl was combined with 10000 mL of water, and mixed well.
  Buffer Dissolution Media
  FaSSIF Buffer Concentrate from Biorelevant.com was used to prepare the Buffer solution according to the instructions provided. The resulting solution was mixed well. The pH of the buffer solution was checked after preparation. If necessary, the pH was adjusted to 6.5±0.05 using either Hydrochloric Acid or Sodium Hydroxide.
  After Acid Resistance samples were pulled, the capsules were taken out of the solution with pincers and placed aside while the vessels are emptied, cleaned and filled with preheated buffer medium. 0.05 w/v % Tween 80 (or equivalent) was added to each dissolution vessel; for example 450 mg of Tween 80 was added to the dissolution vessels after they have been filled with 900 mL of pre-heated buffer, to arrive at a surfactant concentration of 0.05%.

Figure 20:
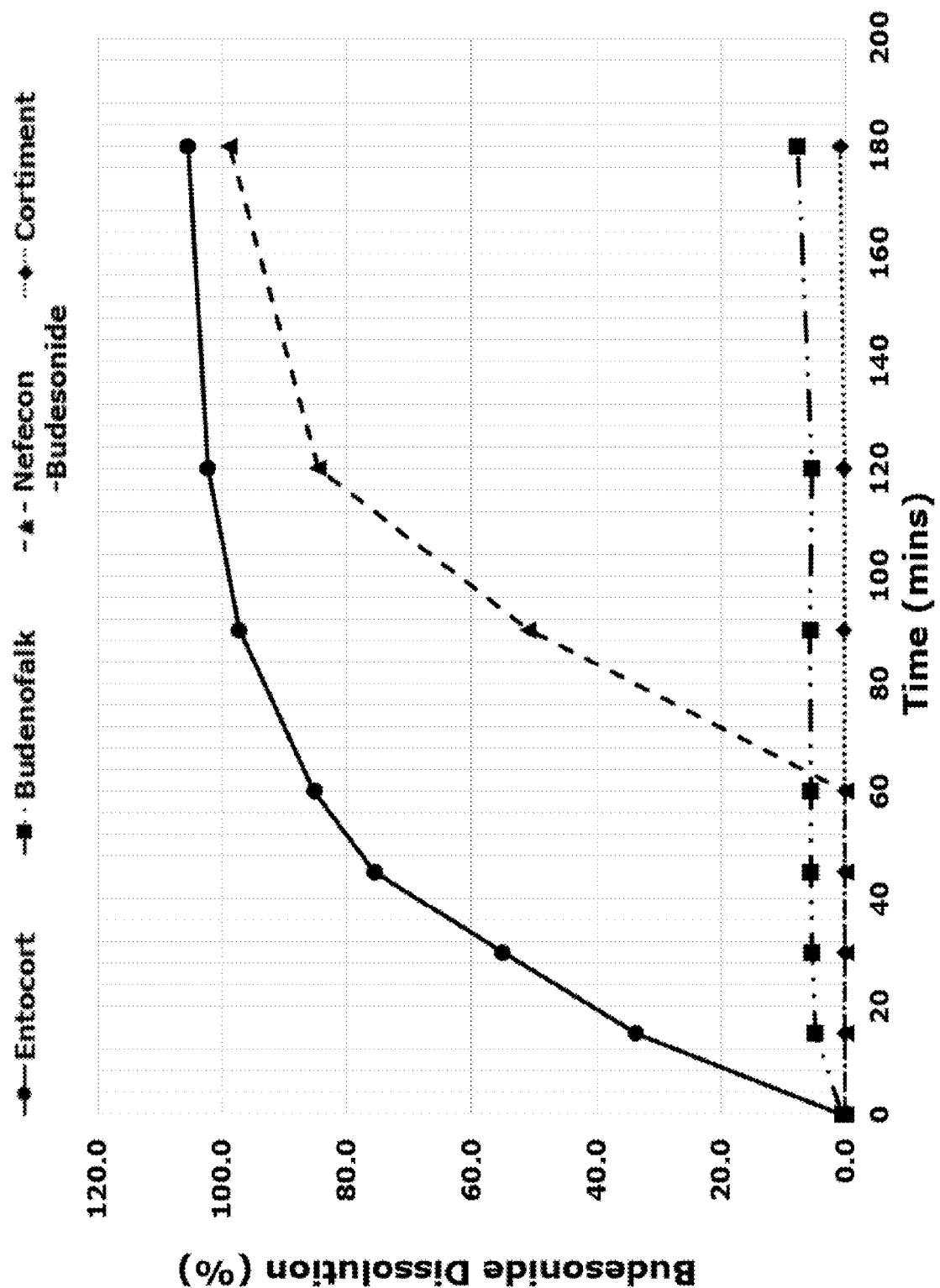
FIG. 20: shows the in vitro dissolution profile of budesonide modified release capsules in FaSSIF in the presence of added surfactant in the Level 1 fasted state simulated intestinal fluid at a pH of about 6.5 as compared with three other marketed budesonide-containing formulations.

After all vessels reached the target temperature, the experiment was started by adding a capsule to each vessel.
Modification of Procedure for Budenofalk
  A different procedure was used when the capsule broke during the acid stage. Most of the acid phase was carefully decanted and then the remaining acid carefully removed with a pipette in order to remove as few pellets from the vessel as possible. The buffer stage was started by adding 900 mL of pre-heated buffer medium, followed by addition of Tween.
Sampling for Both Stages
  10 mL aspirated, 8 mL discarded (through Whatman filter), 1 mL sampled into HPLC vial.
  For the avoidance of doubt, the variations in this test compared to Example 2 do not have an effect on the overall dissolution profiles of the products tested.
  FIG. 20 shows the dissolution profile of the budesonide capsules as compared to the three other budesonide-containing formulations. From this figure it can be clearly seen that within the FaSSIF medium that mimics the environment in the small intestine, the budesonide capsules have a release profile that is distinguished from all other marketed budesonide-containing formulations.

Example 19: Dissolution Profile Analysis of Core-Shell Beads in the Absence of Enteric Coated Capsules According to In Vitro USP<711>/Pharmacopeia Test No. 2.9.3

The cured core-shell beads as prepared in Example 1 in the absence of an enteric coated capsule were also tested under the buffer stage dissolution conditions (only) as outlined in Example 17.

Figure 21:
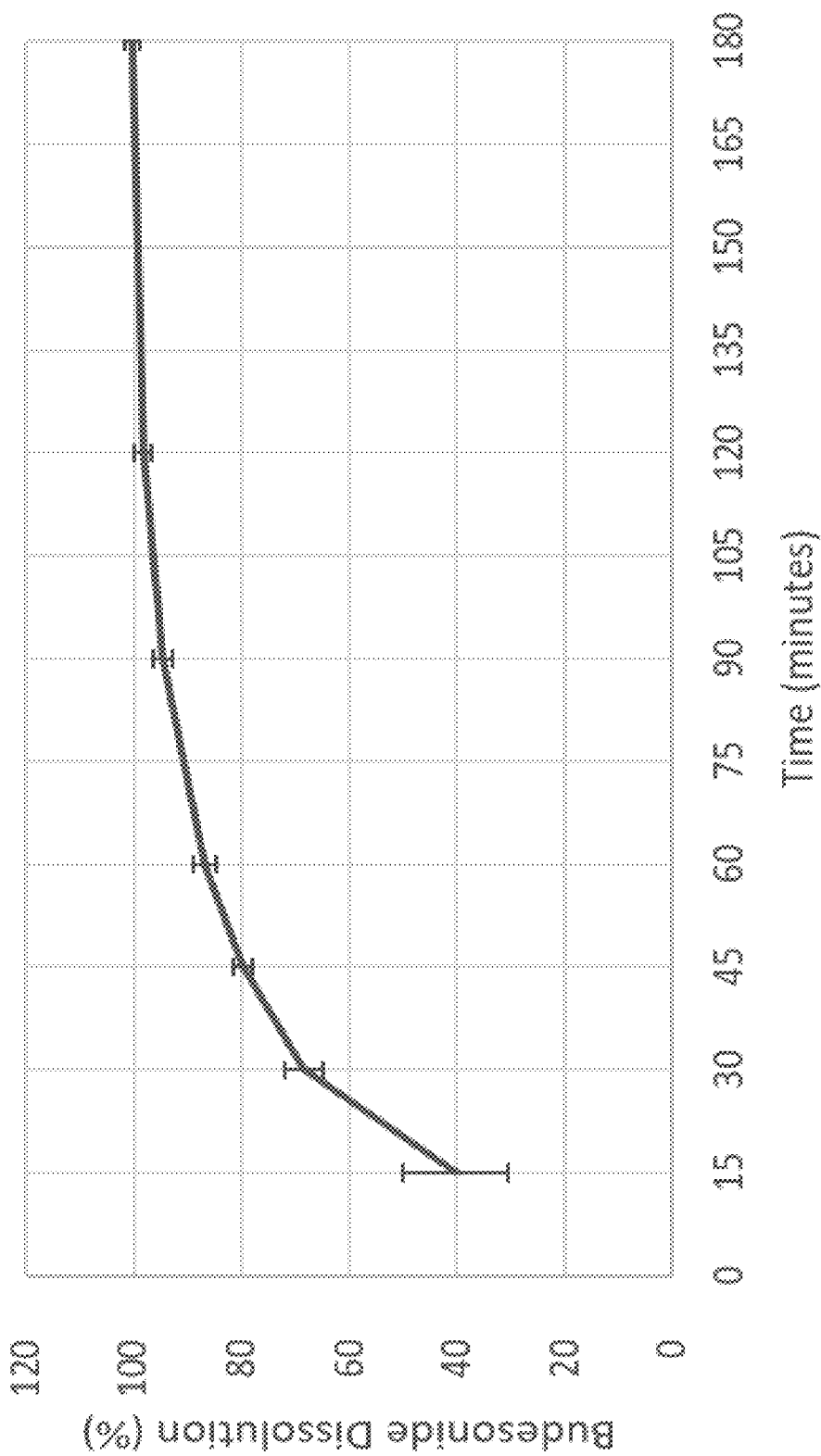
FIG. 21: shows the in vitro dissolution profiles of core-shell bead formulations comprising budesonide in the absence of an enteric coated capsule.

The overall average dissolution profile for three samples in the buffer stage can be seen in FIG. 21.

The quantitative results of the dissolution of budesonide from the core-shell beads in the buffer stage at pH 6.5 at time points 15, 30, 45, 60, 90, 120, and 180 minutes are provided in the table below.

| | Buffer Stage Budesonide Release (%) Time (min) | | | | | | |
|---|---|---|---|---|---|---|---|
| | 15 | 30 | 45 | 60 | 90 | 120 | 180 |
| Vessel 1 | 43.7 | 72.0 | 81.5 | 88.9 | 96.6 | 99.9 | 101.6 |
| Vessel 2 | 29.3 | 64.9 | 78.0 | 84.9 | 93.1 | 96.8 | 99.1 |
| Vessel 3 | 47.6 | 68.2 | 79.6 | 86.4 | 93.9 | 97.7 | 99.9 |
| Mean | 40.2 | 68.3 | 79.7 | 86.7 | 94.5 | 98.1 | 100.2 |
| Range | 29-48 | 65-72 | 78-82 | 85-89 | 93-97 | 97-100 | 99-102 |
| SD | 9.7 | 3.6 | 1.8 | 2.0 | 1.8 | 1.6 | 1.3 |

*SD—standard deviation

The release profile of the core-shell beads in the absence of enteric coated capsules in the FaSSIF Buffer Concentrate further confirms that the bulk of the budesonide will be released in vivo to the ileum. That is to say, the majority of the release from the beads occurs over a 90 minute window and combined with the delay in release from the enteric coating to arrive at the desired dissolution profile of the entire formulation, the bulk of the budesonide will be released in vivo to the ileum as confirmed by the biomarker data obtained and the modelling results provided below in Example 25.

Example 20: General Process for Standard In Vitro Dissolution Test According to USP<711>/pH.Eur. 2.9.3 in the Absence of Added Surfactant Tween 80

The in vitro dissolution of the encapsulated budesonide core-shell beads of Example 1 were analysed as described in Ph.Eur. 2.9.3 Dissolution test for solid dosage forms (using Apparatus 2) and as described in USP <711> Dissolution (using Apparatus 2). The measurement was carried out as described below.

The three marketed budesonide-containing formulations were also analysed in this test. The three formulations being Entocort® (Tillotts Pharma), Budenofalk® (Dr Falk Pharma GmbH) and Cortiment® (Ferring Pharmaceuticals, CH).

| Dissolution Apparatus Setup | |
|---|---|
| Dissolution Apparatus: | USP <711>/Ph. Eur. 2.9.3 Apparatus 2 |
| Vessel Size/Type: | 1000 mL/clear glass, round-bottom |
| Rotation Speed: | 100 rpm |
| Media Volume: | 900 mL - Acid Resistance |
|  | 900 mL - Buffer Dissolution Profile |
| Test Temperature: | 37.0 ± 0.5° C. |
| Pull Volume: | 10 mL |
| Replacement: | No |
| Sampling Time Point: | Acid Resistance Stage: |
|  | 2 hours |
|  | Buffer Stage: |
|  | 15, 30, 45, 60, 90, 120, 180 minutes |
| pH check | Check the pH of the dissolution medium after preparation, and again in each vessel after each test and record the result (Buffer Dissolution Medium only) |

Budesonide release was measured using Ultra Performance Liquid Chromatography (UPLC).
Reagents and Standards
Standards and Reference Materials:
Budesonide, Ph. Eur. CSR or suitable secondary standard.
Dissolution Media and Diluents
Acid Resistance Media
0.1 N HCl Solution. To prepare 10 L of acid resistance media, 82 mL of concentrated HCl was combined with 10000 mL of water and the resulting solution was mixed well.
Buffer Dissolution Media
FaSSIF Buffer Concentrate from Biorelevant.com was used to prepare the Buffer solution according to the instructions provided. The resulting solution was mixed well. The pH of the buffer solution was checked after preparation. If necessary, the pH was adjusted to 6.5±0.05 using either Hydrochloric Acid or Sodium Hydroxide.

After Acid Resistance samples were pulled, the capsules were taken out of the solution with pincers and placed aside while the vessels were emptied, cleaned and filled with 900 mL of pre-heated buffer medium.

After all vessels reached the target temperature, the experiment was started by adding a capsule to each vessel.
Modification of Procedure for Budenofalk
A different procedure was used when the capsule broke during the acid stage. Most of the acid phase was carefully decanted and then the remaining acid carefully removed with a pipette in order to remove as few pellets from the vessel as possible. The buffer stage was started by adding 900 mL of pre-heated buffer medium.
Sampling for Both Stages
10 mL aspirated, 8 mL discarded (through Whatman filter), 1 mL sampled into HPLC vial.
Budesonide release was assessed based on the acceptance criteria in USP<711>/Ph.Eur. 2.9.3.

Example 21: Dissolution Profile Analysis of Budesonide Capsules According to In Vitro USP<711>/Pharmacopeia Test No. 2.9.3 in the Absence of Added Surfactant Tween 80

The enteric coated capsules filled with cured beads ("budesonide capsules") prepared as described in Example 1 above were tested under the dissolution conditions outlined in Example 20.

Figure 22:
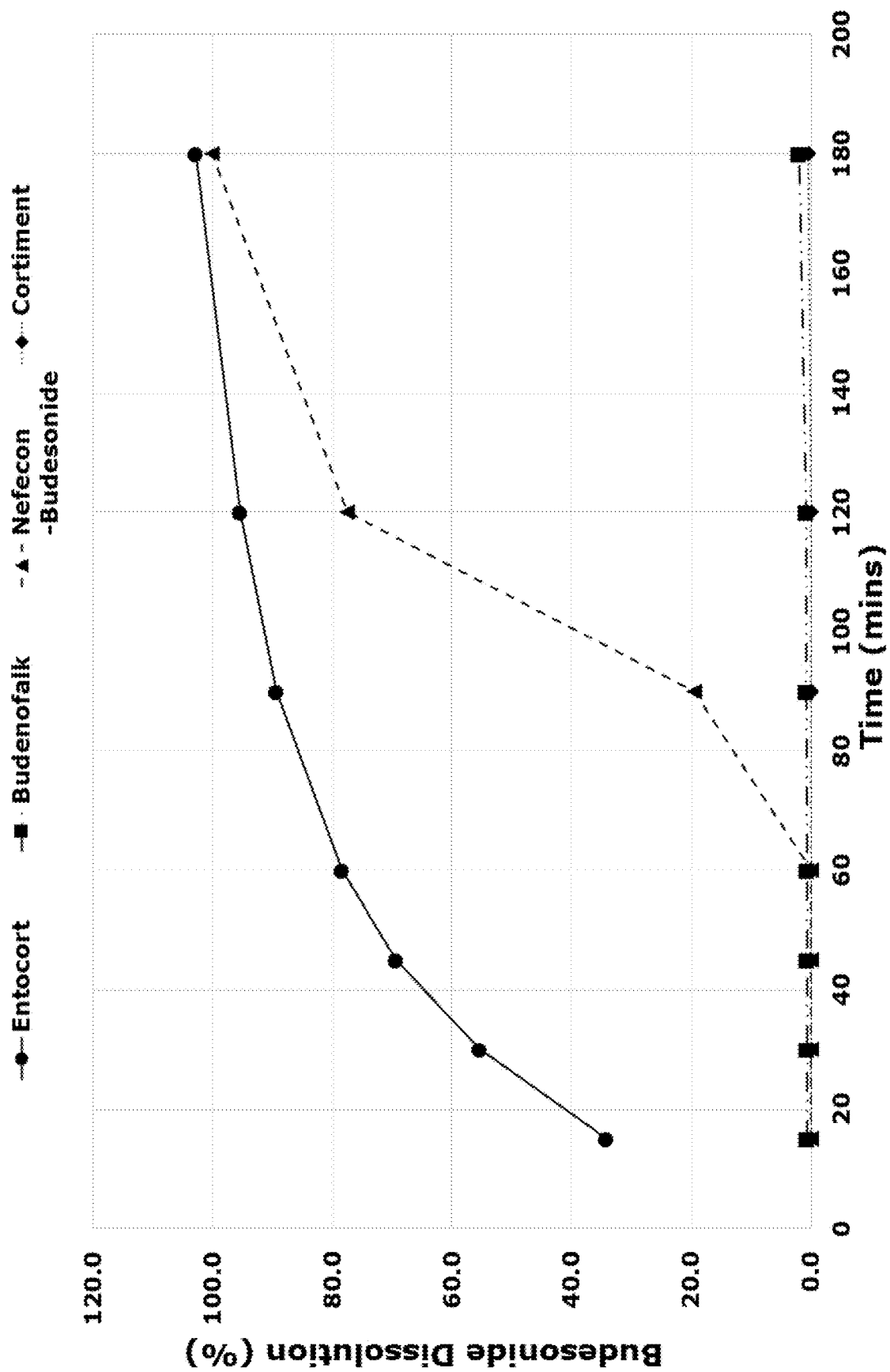
FIG. 22: shows the in vitro dissolution profile of budesonide modified release capsules in FaSSIF in the absence of added surfactant in the Level 1 fasted state simulated intestinal fluid at a pH of about 6.5 as compared with three other marketed budesonide-containing formulations.

The overall average dissolution profile for the budesonide capsules can be seen in FIG. 22. FIG. 22 also contains the dissolution profiles of three other budesonide-containing formulations under the same test as a comparative. From this figure it can be clearly seen that within the FaSSIF medium that mimics the environment in the small intestine, the budesonide capsules have a release profile that is distinguished from all other marketed budesonide-containing formulations.

For the budesonide capsules and Cortiment, no budesonide release was observed in the acid resistance stage at the 2 hour sampling time point. For Entocort budesonide release amounting to 0.8% was observed, and for Budenofalk budesonide release amounting to 0.6% was observed in the acid resistance stage at the 2 hour sampling time point.

The quantitative results of the dissolution of budesonide in the various media at time points 2 hours at pH 1.2, and 15, 30, 45, 60, 90, 120, and 180 minutes in the buffer stage at pH 6.5 are provided in the table below for both the budesonide capsules and the three comparative formulations.

| | Acid Budesonide Release (%) | Buffer Stage Budesonide Release (%) | | | | | | |
|---|---|---|---|---|---|---|---|---|
| | | Time (min) | | | | | | |
| | 120 | 15 | 30 | 45 | 60 | 90 | 120 | 180 |
| | | Budesonide Capsules | | | | | | |
| Mean | 0.0 | 0.0 | 0.0 | 0.0 | 0.0 | 19.4 | 77.7 | 100.1 |
| Range | 0-0 | 0-0 | 0-0 | 0-0 | 0-0 | 1-44 | 72-87 | 98-103 |
| SD | 0.0 | 0.0 | 0.0 | 0.0 | 0.0 | 14.9 | 5.5 | 1.8 |
| | | Entocort | | | | | | |
| Mean | 0.8 | 34.2 | 55.4 | 69.4 | 78.4 | 89.3 | 95.5 | 102.8 |
| Range | 1-1 | 32-37 | 53-57 | 66-71 | 75-82 | 85-92 | 91-98 | 96-109 |
| SD | 0.3 | 1.5 | 1.7 | 2.0 | 2.1 | 2.5 | 2.7 | 4.1 |

-continued

| | Acid Budesonide Release (%) | Buffer Stage Budesonide Release (%) | | | | | | |
|---|---|---|---|---|---|---|---|---|
| | | Time (min) | | | | | | |
| | 120 | 15 | 30 | 45 | 60 | 90 | 120 | 180 |
| | | Budenofalk | | | | | | |
| Mean | 0.6 | 0.6 | 0.6 | 0.6 | 0.6 | 0.8 | 0.8 | 1.9 |
| Range | 0-1 | 0-1 | 0-1 | 0-1 | 0-1 | 1-1 | 1-1 | 2-3 |
| SD | 0.1 | 0.1 | 0.1 | 0.1 | 0.1 | 0.1 | 0.1 | 0.4 |
| | | Cortiment | | | | | | |
| Mean | 0.0 | 0.0 | 0.0 | 0.0 | 0.0 | 0.0 | 0.0 | 0.5 |
| Range | 0-0 | 0-0 | 0-0 | 0-0 | 0-0 | 0-0 | 0-0 | 0-1 |
| SD | 0.0 | 0.0 | 0.0 | 0.0 | 0.0 | 0.0 | 0.0 | 0.2 |

*SD—standard deviation

The budesonide release was assessed based on the acceptance criteria in USP<711>/Ph.Eur. 2.9.3.

The table below shows the f2 values for comparison of the budesonide capsules according to the invention tested under this method with each of the other commercially available products. An f2 value of 50 or greater is required to demonstrate similarity of the profiles (FDA SUPAC Guidances 1995, 1997).

| Nefecon | Entocort EC | Budenofalk | Cortiment |
|---|---|---|---|
| F2 value (biorelevant) | 11.7 | 16.1 | 15.8 |

It is clear that the release profiles of budesonide differ widely among the four commercial products. None of the f2 comparisons between Nefecon and the other products demonstrated similarity, which would require an f2 value of 50 or greater. In fact, based on the f2 evaluation as well as visual inspection of the graphical profiles, their release profiles must be considered strongly dissimilar.

Example 22: First Tablet Formulation

Tablets are manufactured via the following process steps:
1. Wet granulation. Budesonide, mannitol, hydroxyethyl cellulose, hydroxypropyl cellulose and sodium starch glycolate are blended. An ethanol-water mixture is thereafter sprayed on the powder during blending. The resulting granules are thereafter dried.
2. Final blending. The dried granules are blended with sodium stearyl fumarate.
3. Tableting. Tablets are compressed using a tableting machine.
4. Enteric coating. Methacrylic acid and methyl methacrylate copolymers, talc and dibutyl sebacate are dispersed in an isopropyl alcohol-water mixture, during mixing. The coating dispersion is thereafter sprayed onto the tablets using a fluid bed apparatus.

An example of a tablet composition according to the present invention is shown in the table below.

| Tablet composition. | | |
|---|---|---|
| Component | Amount (mg) | Function |
| Budesonide | 4.00 | API (intragranular) |
| Mannitol | 81.50 | Filler (intragranular) |
| Hydroxyethyl cellulose | 5.00 | Binder (intragranular) |
| Hydroxypropyl cellulose | 5.00 | Binder (intragranular) |
| Sodium starch glycolate | 4.00 | Disintegrant (intragranular) |
| Purified water | | Wet granulation solvent |
| Ethanol | * | Wet granulation solvent |
| Sodium stearyl fumarate | 0.50 | Lubricant (extragranular) |
| Total (uncoated tablet) | 100.00 mg | |
| Methacrylic acid and methyl methacrylate copolymer (1:1) | 9.85 | Enteric coating polymer |
| Methacrylic acid and methyl methacrylate copolymer (1:2) | 3.31 | Enteric coating polymer |
| Talc | 3.31 | Glidant, coating uniformity |
| Dibutyl sebacate | 2.55 | Plasticizer |
| Isopropyl alcohol | * | Coating solvent |
| Purified water | * | Coating solvent |
| Total (coated tablet) | 119.02 mg | |

*Removed during process.

Example 23: Second Tablet Formulation

Tablets are manufactured via the following process steps:
1. Wet granulation. Budesonide is initially blended with colloidal silica. Microcrystalline cellulose and dibasic calcium phosphate are thereafter added followed by additional blending. A solution of hydroxypropyl cellulose in an ethanol-water mixture is thereafter sprayed onto the powder during blending. The resulting granules are thereafter dried.
2. Blending. The dried granules are blended with microcrystalline cellulose, sodium starch glycolate and Copovidone. As a final blending step, magnesium stearate is added to the blend, followed by final blending.
3. Tableting. Tablets are compressed using a tableting machine.
4. Enteric coating. Methacrylic acid and methyl methacrylate copolymers, talc and dibutyl sebacate are dispersed in an isopropyl alcohol-water mixture, during mixing. The coating dispersion is thereafter sprayed onto the tablets using a pan coater.

An example of a tablet composition according to the present invention is shown in the table below.

Tablet composition.

| Component | Amount (mg) | Function |
| --- | --- | --- |
| Budesonide, micronized | 4.00 | API (intragranular) |
| Colloidal silica | 0.50 | Glidant (intragranular) |
| Dibasic calcium phosphate | 16.00 | Filler (intragranular) |
| Microcrystalline cellulose | 15.50 | Filler (intragranular) |
| Hydroxypropyl cellulose | 4.00 | Binder (intragranular) |
| Ethanol | * | Wet granulation solvent |
| Purified water | * | Wet granulation solvent |
| Microcrystalline cellulose | 53.50 | Filler (extragranular) |
| Copovidone | 5.00 | Binder (extragranular) |
| Sodium starch glycolate | 1.00 | Disintegrant (extragranular) |
| Magnesium stearate | 0.50 | Lubricant (extragranular) |
| Total (uncoated tablet) | 100.00 mg | |
| Methacrylic acid and methyl methacrylate copolymer (1:1) | 9.85 | Enteric coating polymer |
| Methacrylic acid and methyl methacrylate copolymer (1:2) | 3.31 | Enteric coating polymer |
| Talc | 3.31 | Glidant, coating uniformity |
| Dibutyl sebacate | 2.55 | Plasticizer |
| Isopropyl alcohol | * | Coating solvent |
| Purified water | * | Coating solvent |
| Total (coated tablet) | 119.02 mg | |

*Removed during process.

Example 24: Third Tablet Formulation

Tablet components:

| Component | Amount (mg) | Function |
| --- | --- | --- |
| Budesonide, micronized | 4 | Active Pharmaceutical Ingredient (API) |
| Microcrystalline cellulose | 61.5 | Filler |
| Calcium hydrogen phosphate dihydrate | 10 | Filler |
| Hypromellose, 100 mPas | 10 | Filler/gelling agent |
| Hypromellose, 4000 mPas | 10 | Filler/gelling agent |
| Crospovidone | 4 | Disintegrant |
| Purified water | * | Wet granulation solvent |
| Sodium stearyl fumarate | 0.5 | Lubricant |
| Total, uncoated tablet | 100 | |
| Methacrylic acid-methyl methacrylate copolymer (1:1) | 8.7 | Enteric coating polymer |
| Methacrylic acid-methyl methacrylate copolymer (1:2) | 2.9 | Enteric coating polymer |
| Talc | 2.9 | Glidant, coating uniformity |
| Dibutyl sebacate | 2.2 | Plasticizer |
| Isopropyl alcohol | * | Coating solvent |
| Purified water | * | Coating solvent |
| Total, coated tablet | 117 | |

*Removed during manufacturing.

Manufacturing of Uncoated Tablets (200 g Batch Size)
1. Budesonide and all excipients except Sodium stearyl fumarate were blended with a Turbula mixer (blending at 46 rpm for 75 min).
2. The powder blend was granulated by spraying water on the powder during blending. The amount of water sprayed was 15% of the weight of the dry powder.
3. The granules were dried over night at 50° C.
4. The dried granules were mixed with sodium stearyl fumarate (lubricant) for 10 min at 46 rpm, using a Turbula mixer.
5. Tablets were compressed, to an uncoated tablet weight of 100 mg.

Preparation of Coating Dispersion

A coating dispersion was prepared with the composition shown in the table below. The dispersion was prepared according to the following steps:
1. A diluent mixture was prepared by blending isopropyl alcohol, water and dibutyl sebacate in a vessel (Vessel A).
2. A Eudragit suspension was prepared by transferring approximately half of the diluent mixture (in Vessel A) to another vessel (Vessel B). Eudragit L100 and Eudragit S100 were thereafter added slowly to Vessel B during mixing. The Eudragit suspension in Vessel B was thereafter mixed for another 30-60 min.
3. Talc was added slowly to the remaining diluent mixture in Vessel A, during mixing with a high shear mixer. The talc suspension was thereafter mixed for an additional 10 min with high shear mixer.
4. The talc suspension in Vessel A was thereafter slowly poured into the Eudragit suspension (Vessel B) during mixing.
5. The mixture in Vessel B was thereafter stirred for 24 h at room temperature.
6. The mixture was passed through a 0.5 mm sieve.
7. The final coating dispersion was thereafter stored at room temperature under continuous stirring until and during coating.

| Commodity name | Amount (g) | Supplier |
| --- | --- | --- |
| Eudragit L100 (Methacrylic acid copolymer type A) | 39.4 | Evonik |
| Eudragit S100 (Methacrylic acid copolymer type B) | 13.22 | Evonik |
| Talc, Pharma M grade | 13.22 | Imerys |
| Dibutyl sebacate USP/NF | 10.18 | Merck |
| Isopropyl alcohol | 594.36 | — |
| Water purified | 20.44 | — |
| Total | 690.82 | |

Coating of Tablets (50 g Batch Size)

Tablets were coated using a stainless-steel pan coater with 12 cm diameter, and a standard spray nozzle. Coating weight gain was determined by weighing tablet samples after different coating durations. The following spraying parameters were used:

Rotation speed of coating pan: 20-30 rpm
Product temperature: 24-27° C.
Pump flow: 250-260 µl/min
Spray nozzle air pressure: 0.25 bar In Vitro Dissolution of Tablets The in vitro dissolution profiles of the tablets were analysed according to the protocol outlined in Example 6 above (Comparative test according to USP<711>/Ph.Eur. 2.9.3 in the absence of surfactant in the phosphate buffer stage and at a paddle rotation speed of 100 rpm) and the protocol outlined in Example 20 above (General Process For Standard in vitro dissolution test according to USP<711>/Ph.Eur. 2.9.3 in FaSSIF buffer in the absence of added surfactant Tween 80 at 100 rpm). The dissolution values at certain time points can be seen below.

|  |  | Dissolution (%) | | | | |
| --- | --- | --- | --- | --- | --- | --- |
|  |  | HCl 2 h | buffer 15 min | buffer 30 min | buffer 60 min | buffer 120 min |
| Phosphate buffer, pH 6.8 | Tablet 1 | 0 | 0 | 0 | 14.3 | 75.8 |
|  | Tablet 2 | 0 | 0 | 0 | 44.9 | 87.0 |
|  | Average | 0 | 0 | 0 | 29.6 | 81.4 |
| FaSSIF | Tablet 1 | 0 | 0 | 0 | 36.1 | 75.7 |
|  | Tablet 2 | 0 | 0 | 0 | 30.3 | 72.2 |
|  | Average | 0 | 0 | 0 | 33.2 | 73.9 |

The budesonide release from these tablets matches the dissolution profile required to achieve the majority of release to the ileum. What is particularly surprising that the combination of a gelling agent (hypromellose) with a disintegrant (crospovidone) allowed the achievement of the correct in vitro dissolution profile. Although it is expected that other tablet formulations are possible to achieve the desired release profile.

Example 25: In Silico Modelling of Site of Release of Budesonide Capsules

A physiologically based pharmacokinetic (PBPK) model of the capsules prepared in Example 1 ("budesonide capsules" or "nefecon budesonide") was run using GastroPlus® software (Simulations Plus, CA; version 9.8.3002).

The in vitro release of the budesonide capsules with an acid stage (first 2 hours) followed by a buffer stage according to the protocol outlined in Example 2 was uploaded in the PBPK software. The IVIVC (in vitro in vivo correlation) was obtained to correlate the PBPK model prediction with measured pharmacokinetic results. The predicted Cmax was faster and higher than observed. However, Budesonide is known to undergo gut wall metabolism in the small intestine (Seidegård J et. al., *Presystemic elimination of budesonide in man when administered locally at different levels in the gut, with and without local inhibition by ketoconazole*. Eur J Pharm Sci. 2008 Nov. 15; 35(4):264-70; Raje et al. *Evaluation of separate role of intestine and liver in first pass metabolism of budesonide in rat* Xenobiotica. 2018 December; 48(12):1206-1214). After introducing gut wall metabolism to the PBPK model a good fit of the data was achieved.

Figure 23A:
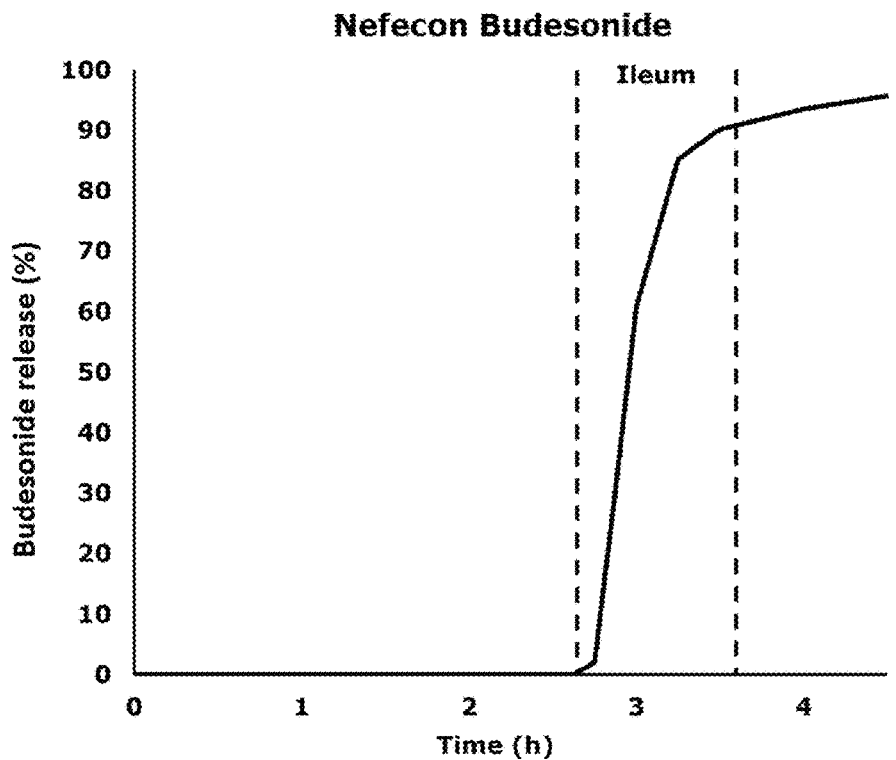
FIGS. 23A-B: 23A shows the results of a PBPK model based on the dissolution of the modified release capsules; and 23B shows the results of a PBPK model based on the dissolution of comparative product Entocort®.
Figure 23B:
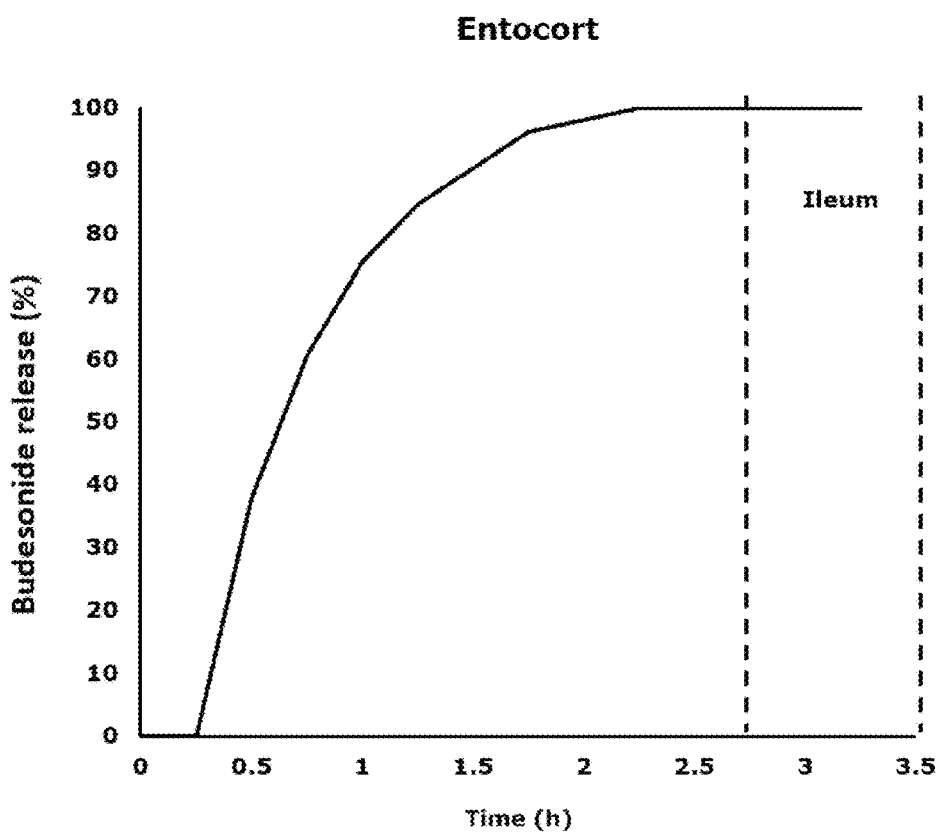

As can be seen in FIG. 23(*a*), the IVIVC PBPK model confirmed that the budesonide capsules began releasing budesonide only once the ileum was reached and at least about 90% of the budesonide was released throughout the entire ileum, with the small remainder being released in the section of the intestines following the ileum (i.e. the caecum). Therefore, this model confirms that a composition having an in vitro release profile as defined by the invention achieves release of the budesonide payload to the site of highest concentration of Peyer's patches in the intestinal tract, being the ileum and, therefore, any composition fitting this release profile will be effective in treating IgA nephropathy.

Release of budesonide from Entocort® (Tillotts Pharma) was also modelled using the GastroPlus® software and the results showed that all budesonide was released prior to the formulation entering the ileum section of the small intestines (see FIG. 23(*b*)).

Example 26: Study on In Vivo Release of Capsule Contents

A study was conducted to evaluate where and when capsules coated with the same enteric coating as the capsules described in Example 1 release their contents in the gastrointestinal tract.

In this study, VCaps plus size 1 HPMC capsules were filled with 75 mg of caffeine, 10 mg black iron oxide, and 87.5 mg manganese gluconate dehydrate. 140.9 mg of sugar beads (also called pellets) were added to replicate the total weight of the cores in the capsules described in Example 1. The capsules were then coated with the same enteric coating, using the same coating process and the same equipment and facilities, as the capsules described in Example 1.

The caffeine was placed inside the capsules to use as a marker to determine when the contents of the capsule were released, by measuring appearance of caffeine in the saliva at various time points. Caffeine is rapidly absorbed after release in the intestinal tract, and as such, the appearance of caffeine in saliva provides a sensitive marker of capsule opening (Sager et al. Low dose caffeine as a salivary tracer for the determination of gastric water emptying in fed and fasted state: A MRI validation study. Eur J Pharm Biopharm 127:443-452 (2018)). The iron oxide was placed inside the capsule so that magnetic resonance imaging (MRI) could be used to locate the position of the capsule as it moves through the gastrointestinal tract by visualizing the iron oxide.

The study was performed at the University Clinic in Greifswald, Germany, as an open-label, single-center study in 12 healthy young human subjects. The subjects stopped ingesting caffeine-containing foods and drinks for three days prior to their participation in the study and fasted overnight prior to the study for at least 10 hours.

An MRI scan was performed, and a saliva sample obtained, prior to each participant's ingestion of the enteric coated capsule with a glass of water. Subsequently, MRI scans were performed every 15 minutes for the first four hours and thereafter every 30 minutes until the study was completed. Saliva samples were obtained one minute after each MRI scan. MRI imaging was conducted with a Siemens MAGNETOM Avanto MR-scanner (Siemens Healthcare, Erlangen, Germany) with a field strength of 1.5 Tesla and imaging data were analyzed using Horos 2.2.0 (The Horos Project). All measurements were performed with the subject in the supine position (lying on their back, head up). Saliva samples were analyzed using a LCMS 8060 system (Shimadzu Corporation, Kyoto, Japan) and appropriately prepared for this purpose.

Figure 24:
FIG. 24: Coronal MRI images of T2*/T1 weighted TRUFI with detection of iron oxide loaded capsules at 15 and 90 minutes, as well as dispersion of iron oxide in the ileum at 270 minutes.

FIG. 24 shows MRI images for different locations within the gastrointestinal tract. At 15 and 90 minutes the capsule is intact and located in the stomach and jejunum, respectively, while at 270 minutes the capsule has released its contents and the iron oxide has dispersed in the ileum.

The average gastric emptying time of the capsules (time at which the capsule moved out of the stomach) was 58±30 min (highest observed gastric emptying time was 112.5 min). These values are consistent with the usual gastric emptying times for large, non-disintegrating dosage forms (Wilson et al. Chapter 3. Gastrointestinal Transit and Drug Absorption (pages 41 to 65) In "Oral Drug Absorption: Prediction and Assessment" Edited by J. Dressman and C. Reppas—2nd. Edition Drug and the Pharmaceutical Sciences Vol. 193 Marcel Dekker, NY, NY ISBN-13: 978-1-4200-7733-9 (2010)). None of the capsules showed disintegration in the stomach.

The first time point with a measured concentration ≥10 ng/ml of caffeine in undiluted saliva was considered as the "salivary caffeine appearance". As shown in the table below, the average time to the first appearance of caffeine in saliva was 238 minutes after capsule ingestion, with a standard deviation of 47 minutes and a range of 158-345 minutes. After subtracting the individual's gastric emptying time from the time at which caffeine first appeared in their saliva, the time for release of caffeine after entering the small intestine was calculated as averaging 181±31 minutes (range 120-233 minutes). These values indicate that opening of the enteric coated capsule and release of caffeine fell well within the usual range of small intestinal transit times (3.5 to 4.5 hours (210 to 270 minutes)) (Wilson et al. Chapter 3. Gastrointestinal Transit and Drug Absorption (pages 41 to 65) In "Oral Drug Absorption: Prediction and Assessment" Edited by J. Dressman and C. Reppas—2nd. Edition Drug and the Pharmaceutical Sciences Vol. 193 Marcel Dekker, NY, NY ISBN-13: 978-1-4200-7733-9 (2010)).

The table below shows the individual and average results of gastric emptying time (as determined by MRI), time of salivary caffeine appearance and time of salivary caffeine appearance after gastric emptying.

| Subject | Gastric Emptying Time (min) | Time to Salivary Caffeine Appearance after ingestion (min) | Time to Salivary Caffeine Appearance after gastric emptying (min) |
|---|---|---|---|
| 001 | 53 | 203 | 150 |
| 002 | 83 | 255 | 173 |
| 003 | 68 | 255 | 188 |
| 004 | 23 | 218 | 195 |
| 005 | 38 | 218 | 180 |
| 006 | 113 | 345 | 233 |
| 007 | 8 | 218 | 210 |
| 008 | 53 | 218 | 165 |
| 009 | 68 | 285 | 218 |
| 010 | 53 | 233 | 180 |
| 011 | 98 | 255 | 158 |
| 012 | 38 | 158 | 120 |
| mean | 58 | 238 | 181 |
| SD | 30 | 47 | 31 |

Based on the first time of appearance of caffeine in the saliva and the location of the iron oxide in the corresponding MRI image, the enteric coated capsules opened and released their contents in the ileum in 10 of the 12 subjects. The study thus confirms that the enteric coating and capsule described in Example 1 consistently results in release of the capsule's contents to the ileum. The beads contained in Example 1 would start releasing budesonide after the capsule opens, with the majority of release occurring within one hour. Comparing the average small intestinal transit time for beads of 3.5 to 4.5 hours (Wilson et al. Chapter 3. Gastrointestinal Transit and Drug Absorption (pages 41 to 65) In "Oral Drug Absorption: Prediction and Assessment" Edited by J. Dressman and C. Reppas—2nd. Edition Drug and the Pharmaceutical Sciences Vol. 193 Marcel Dekker, NY, NY ISBN-13: 978-1-4200-7733-9 (2010)) with the average time for the capsules to open once they reach the small intestine (181 minutes in this study), plus the time required for release of the majority of the budesonide from the beads (about one hour), it can be concluded that the majority of the budesonide would be released from the beads to the distal ileum and thus be targeted to the Peyer's Patches located there.

The invention claimed is:

1. A method of treating IgA nephropathy in a subject in need thereof, comprising administering to the subject a pharmaceutical composition comprising one or more cores comprising budesonide;
   wherein the one or more cores are coated with an extended release pharmaceutically-acceptable polymeric blend comprising ethylcellulose in an amount of about 51.8 wt. % of the extended release pharmaceutically-acceptable polymeric blend and hydroxypropylmethyl cellulose in an amount of about 27.3 wt. % of the extended release pharmaceutically-acceptable polymeric blend;
   wherein the extended release pharmaceutically-acceptable polymeric blend is present in an amount of from about 5 wt. % to about 18 wt. % of the total coated core weight;
   wherein the pharmaceutical composition is orally administered as a capsule that comprises an enteric coating in an amount of from about 34 mg to about 46 mg per capsule;
   wherein the pharmaceutical composition meets the following release profile in a standard in vitro USP<711> dissolution test using a dissolution apparatus according to Apparatus 2 (Paddle Apparatus) at a paddle rotation speed of 100 rpm:
   a) no more than about 10% of the budesonide is released into an aqueous dissolution medium with a pH of about 1.2 within about 120 minutes;
   b) no more than about 10% of the budesonide is released into a pharmaceutically-relevant dissolution medium within about 30 minutes, wherein the pharmaceutically-relevant dissolution medium is a Level 1 Fasted State Simulated Intestinal Fluid at a pH of about 6.5, or a phosphate buffer medium at a pH of about 6.8; and
   c) at least about 70% of the budesonide is released into the pharmaceutically-relevant dissolution medium within about 120 minutes; and
   wherein the subject is administered a daily dose of about 16 mg of budesonide.

2. The method of claim 1, wherein the budesonide is substantially released to the ileum region of the small intestine in the subject.

3. The method of claim 2, wherein at least about 60% of the initial content of budesonide is released to the ileum region of the small intestine in the subject.

4. The method of claim 2, wherein at least about 90% of the initial content of budesonide is released to the ileum region of the small intestine in the subject.

5. The method of claim 1, wherein the pharmaceutically-relevant dissolution medium is a Level 1 Fasted State Simulated Intestinal Fluid at a pH of about 6.5.

6. The method of claim 1, wherein the pharmaceutically-relevant dissolution medium is a phosphate buffer medium at a pH of about 6.8.

7. A method of treating IgA nephropathy in a subject in need thereof, comprising administering to the subject a pharmaceutical composition comprising one or more cores comprising budesonide;
   wherein the one or more cores are coated with an extended release pharmaceutically-acceptable polymeric blend comprising ethylcellulose in an amount of from about 47 wt. % to about 56 wt. % of the extended release pharmaceutically-acceptable polymeric blend and hydroxypropylmethyl cellulose in an amount of from about 32 wt. % to about 22 wt. % of the extended release pharmaceutically-acceptable polymeric blend;
   wherein the extended release pharmaceutically-acceptable polymeric blend is present in an amount of from about 5 wt. % to about 18 wt. % of the total coated core weight;
   wherein the pharmaceutical composition is orally administered as a capsule that comprises an enteric coating in an amount of from about 34 mg to about 46 mg per capsule;

wherein the pharmaceutical composition meets the following release profile in a standard in vitro USP<711> dissolution test using a dissolution apparatus according to Apparatus 2 (Paddle Apparatus) at a paddle rotation speed of 100 rpm:
  a) no more than about 10% of the budesonide is released into an aqueous dissolution medium with a pH of about 1.2 within about 120 minutes;
  b) no more than about 10% of the budesonide is released into a pharmaceutically-relevant dissolution medium within about 30 minutes, wherein the pharmaceutically-relevant dissolution medium is a Level 1 Fasted State Simulated Intestinal Fluid at a pH of about 6.5, or a phosphate buffer medium at a pH of about 6.8; and
  c) at least about 70% of the budesonide is released into the pharmaceutically-relevant dissolution medium within about 120 minutes; and
wherein the subject is administered a daily dose of about 16 mg of budesonide.

8. The method of claim 7, wherein the extended release pharmaceutically-acceptable polymeric blend is present in an amount of from about 6 wt. % to about 13 wt. % of the total coated core weight.

9. The method of claim 7, wherein the extended release pharmaceutically-acceptable polymeric blend is present in an amount of 9.1 wt. % (±2%) of the total coated core weight.

10. The method of claim 9, wherein the budesonide is substantially released to the ileum region of the small intestine in the subject.

11. The method of claim 10, wherein at least about 60% of the initial content of budesonide is released to the ileum region of the small intestine in the subject.

12. The method of claim 10, wherein at least about 90% of the initial content of budesonide is released to the ileum region of the small intestine in the subject.

13. The method of claim 7, wherein the pharmaceutically-relevant dissolution medium is a Level 1 Fasted State Simulated Intestinal Fluid at a pH of about 6.5.

14. The method of claim 7, wherein the pharmaceutically-relevant dissolution medium is a phosphate buffer medium at a pH of about 6.8.

15. The method of claim 5, wherein the Level 1 Fasted State Simulated Intestinal Fluid comprises an added surfactant.

16. The method of claim 15, wherein the added surfactant is present in an amount of about 0.5 mg/mL.

17. The method of claim 6, wherein the phosphate buffer medium comprises an added surfactant.

18. The method of claim 17, wherein the surfactant is present in an amount of about 0.5 mg/mL.

19. The method of claim 13, wherein the Level 1 Fasted State Simulated Intestinal Fluid comprises an added surfactant.

20. The method of claim 19, wherein the added surfactant is present in an amount of about 0.5 mg/mL.

21. The method of claim 14, wherein the phosphate buffer medium comprises an added surfactant.

22. The method of claim 21, wherein the surfactant is present in an amount of about 0.5 mg/mL.

23. The method of claim 1, wherein the capsule is a size 1 capsule.

24. The method of claim 7, wherein the capsule is a size 1 capsule.

25. The method of claim 1, wherein the extended release pharmaceutically-acceptable polymeric blend is present in an amount of from about 6 wt. % to about 13 wt. % of the total coated core weight.

26. The method of claim 1, wherein the ethylcellulose is present in an amount of 51.8 wt. % (±2%) of the extended release pharmaceutically-acceptable polymeric blend, the hydroxypropylmethyl cellulose is present in an amount of 27.3 wt. % (±2%) of the extended release pharmaceutically-acceptable polymeric blend, the extended release pharmaceutically-acceptable polymeric blend is present in an amount of 9.1 wt. % (±2%) of the total coated core weight, and the capsule is a size 1 capsule.

* * * * *

UNITED STATES PATENT AND TRADEMARK OFFICE
CERTIFICATE OF CORRECTION

PATENT NO. : 11,896,719 B2
APPLICATION NO. : 18/100396
DATED : February 13, 2024
INVENTOR(S) : Riesel et al.

It is certified that error appears in the above-identified patent and that said Letters Patent is hereby corrected as shown below:

In the Specification

In Column 6, Line 22, delete "35".

In Column 34, Line 51, delete "pH.Eur." and insert --Ph.Eur.--.

In Column 36, Line 61, delete "pH.Eur." and insert --Ph.Eur.--.

In Column 38, Line 29, delete "740/of" and insert --74% of--.

In Column 38, Line 49, delete "pH.Eur." and insert --Ph.Eur.--.

In Column 39, Line 60, delete "pH.Eur." and insert --Ph.Eur.--.

In Column 51, Line 41, delete "pH.Eur." and insert --Ph.Eur.--.

In Column 54, Line 63, delete "pH.Eur." and insert --Ph.Eur.--.

Signed and Sealed this
Twenty-sixth Day of March, 2024

Katherine Kelly Vidal
*Director of the United States Patent and Trademark Office*